(12) United States Patent
Guillou et al.

(10) Patent No.: US 8,703,808 B2
(45) Date of Patent: Apr. 22, 2014

(54) USE OF DERIVATIVES OF INDOLES FOR THE TREATMENT OF CANCER

(75) Inventors: Catherine Guillou, Gif-sur-Yvette (FR); Frank Kozielski, Hamburg (DE); Christophe Labriere, Brest (FR); Francoise Gueritte, Gif-sur-Yvette (FR); Sergey Tcherniuk, Fontaine (FR); Dimitrios Skoufias, Fontaine (FR); Claude Thal, Sceaux (FR); Henri-Philippe Husson, Chevreuse (FR)

(73) Assignees: Centre National de la Recherche Scientifique, Paris (FR); Commissariat a l'Energie Atomique et aux Energies Alternatives, Paris (FR)

( * ) Notice: Subject to any disclaimer, the term of this patent is extended or adjusted under 35 U.S.C. 154(b) by 0 days.

(21) Appl. No.: 13/588,600

(22) Filed: Aug. 17, 2012

(65) Prior Publication Data

US 2013/0131084 A1 May 23, 2013

Related U.S. Application Data

(63) Continuation of application No. 13/379,469, filed as application No. PCT/IB2010/052866 on Jun. 23, 2010, now abandoned.

(30) Foreign Application Priority Data

Jun. 23, 2009 (EP) .................................. 09163523

(51) Int. Cl.
*A01N 43/38* (2006.01)
*A61K 31/405* (2006.01)
*C07D 209/04* (2006.01)

(52) U.S. Cl.
USPC .......................................... 514/415; 548/469

(58) Field of Classification Search
None
See application file for complete search history.

(56) References Cited

U.S. PATENT DOCUMENTS

| | | |
|---|---|---|
| 6,335,342 B1 | 1/2002 | Longo et al. |
| 6,489,134 B1 | 12/2002 | Goldstein et al. |
| 6,890,933 B1 | 5/2005 | Feng et al. |
| 2003/0004350 A1 | 1/2003 | Longo et al. |
| 2006/0030583 A1 | 2/2006 | Arnold et al. |
| 2006/0074075 A1 | 4/2006 | Hadida-Ruah et al. |
| 2007/0049615 A1 | 3/2007 | Ibrahim et al. |
| 2007/0066641 A1 | 3/2007 | Ibrahim et al. |
| 2008/0071095 A1 | 3/2008 | Hadida-Ruah et al. |
| 2008/0221119 A1 | 9/2008 | Arnold et al. |
| 2009/0005378 A1 | 1/2009 | Arnold et al. |
| 2009/0227797 A1 | 9/2009 | Hadida Ruah et al. |
| 2009/0298876 A1 | 12/2009 | Hadida Ruah et al. |
| 2009/0306056 A1 | 12/2009 | Arnold et al. |
| 2010/0048568 A1 | 2/2010 | Aldous et al. |
| 2010/0324065 A1 | 12/2010 | Ibrahim et al. |

FOREIGN PATENT DOCUMENTS

| | | |
|---|---|---|
| WO | 94 26260 | 11/1994 |
| WO | 01 98299 | 12/2001 |
| WO | 2005 062795 | 7/2005 |
| WO | 2008 121670 | 10/2008 |
| WO | 2010 008427 | 1/2010 |

OTHER PUBLICATIONS

Castle et al. J. Org. Chem 1959 (24) 1189-92.*
Madge et al. Bioorganic & Medicinal Chemistry Letters 1996 (6) 857-60.*
Fortuna, C. G., et al., "Synthesis and applications of new *trans* 1-indolyl-2-(1-methyl pyridinium and quinolinium-2-yl)ethylenes," ARKIVOC: Free Online Journal of Organic Chemistry, vol. 8, pp. 222-229, (Jan. 1, 2009) XP008135850.
Liu, J., et al., "Synthesis and antitumor activity of 3-[(substituted phenyl)vinyl]indole derivatives," CODEN: YHHPAL, vol. 34, No. 12, pp. 908-912, (Dec. 1, 1999) XP002319004.
Low, K. H., et al., "Phosphine-Mediated Coupling of Gramines with Aldehydes: A Remarkably Simple Synthesis of 3-Vinylindoles," Organic Letters, vol. 7, No. 10, pp. 2003-2005, (2005) XP002634703.
Singh, A. K., et al., "A fluorescence study of differently substituted 3-styrylindoles and their interaction with bovine serum albumin," Luminescence, vol. 24, No. 2, pp. 123-130, (Feb. 27, 2009) XP002634704.

(Continued)

*Primary Examiner* — Jeffrey S. Lundgren
*Assistant Examiner* — Michael Schmitt
(74) *Attorney, Agent, or Firm* — Oblon, Spivak, McClelland, Maier & Neustadt, L.L.P.

(57) ABSTRACT

The present invention relates to the use of derivatives of indoles having a general formula (I) as follow:

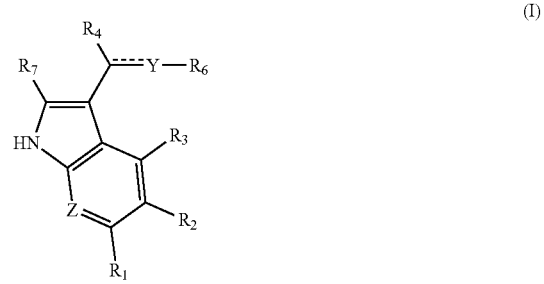

for the manufacture of a pharmaceutical composition intended for the treatment of cancer.

6 Claims, No Drawings

(56) References Cited

OTHER PUBLICATIONS

Sonar, V. N., et al., "(z)-3-(1H-Indol-3-yl)-2-(3-thienyl) acrylonitrile and (z)-3-[1-(4-tert-butylbenzyl)-1H-indol-3-yl]-2-(3-thienyl) acrylonitrile," Acta Crystallographica, Section C: Crystal Structure Communications, vol. c61, No. 2, (2005) XP002634705 English abstract only.

Naruto, S., et al., "Synthesis and Spasmolytic Activity of 2-Substituted-3-(.omega.-dialkylamino-alkoxyphenyl)acrylonitriles and Related Compounds," Chemical & Pharmaceutical Bulletin, vol. 31, No. 6, pp. 2023-2032, (1983) XP008113347.

Efremova, T. M., et al., "Carbolines. VII. 1-Methyl-4-hetarylmethyl-.beta.-carbolines," Khimiya Geterotsiklicheskikh Soedinenii, No. 10, pp. 1382-1387, (Oct. 1974) XP008113349.

De Silva, S. O., et al., "The Wittig Synthesis and Photocyclodehydrogenation of 3-(2-Aryl)vinylindole Derivatives," Canadian Journal of Chemistry, vol. 52, No. 8, Pt. 1, pp. 1294-1306, (1974) XP008113342.

Jin, Q-X., et al., "Synthesis of trans-5-methyloxy-3-styrenylindole," CODEN: HUSHDR, vol. 28, No. 6, (2006) XP002634706 English abstract only.

Minot, C., et al., "Photocyclization of stilbenes and of related indolic compounds: contribution of the use of reactivity indexes," Tetrahedron, vol. 36, No. 9, pp. 1209-1214, (1980) XP003006763.

Moriya, T., et al., "Preparation and Reactions of 3-(Aminomethylene)-3H-indoles," Chemical & Pharmaceutical Bulletin, vol. 28, No. 6, pp. 1711-1721, (1980) XP008113344.

Dieng, C., et al., "Carbolines. VII. 1-Metyl-4-hetarylmethyl-beta-carbolines," Journal of Heterocyclic Chemistry, vol. 12, No. 3, pp. 455-460, (Jun. 1, 1975) XP003006766.

Levitzki, A., "Tyrosine kinases as targets for cancer therapy," European Journal of Cancer, vol. 38, Suppl. 5, pp. S11-S18, (Sep. 2002) XP002550687.

Anafi, M., et al., "Tyrphostin-Induced Inhibition of $p210^{bcr-abl}$ Tyrosine Kinase Activity Induces K562 to Differentiate," Blood, vol. 82, No. 12, pp. 3524-3529, (Dec. 15, 1993) XP002550688.

Tcherniuk, S., et al., "Relocation of Aurora B and Survivin from Centromeres to the Central Spindle Impaired by a Kinesin-Specific MKLP-2 Inhibitor," Angewandte Chemie. International Edition, vol. 49, No. 44, pp. 8228-8231, (Jan. 1, 2010) XP008135676.

International Search Report Issued Jul. 1, 2011 in PCT/IB10/052866 Filed Jun. 23, 2010.

European Search Report Issued Oct. 16, 2009 in European Patent Application No. 09163523.5 Filed Jun. 23, 2009.

* cited by examiner

USE OF DERIVATIVES OF INDOLES FOR THE TREATMENT OF CANCER

CROSS REFERENCE TO RELATED APPLICATIONS

This application is a continuation application of prior U.S. patent application Ser. No. 13/379,469, filed on Dec. 20, 2011, the disclosure of which is incorporated herein by reference in its entirety. The parent application is the National Stage of PCT/IB10/052,866, filed Jun. 23, 2010, and claims priority to European Application No. 09163523.5, the disclosures of both being incorporated herein by reference in their entireties.

The present invention relates to derivatives of indoles and to their application in therapeutics, and in particular to treat the cancer.

Cell division is a highly dynamic process, which depends on the proper interaction of mitotic spindle microtubules (MTs) with chromosomes during mitosis. Because of the dynamic nature of mitosis, proteins involved in the process are prime targets for the development of inhibitors that can be used as antimitotic agents with a potential chemotherapeutic value.

Currently, the anti-cancer drugs used in cancer chemotherapy are antimitotic agents, such as taxanes (Paclitaxel, Docetaxel) which target tubulin, the basic component for the polymerization of mitotic microtubules.

Other anti-cancer drugs are vinca-alkaloids, such as vinorelbine or vinblastine, alkylating agents, such as cisplatine, DNA intercaling agents, such as doxorubicin, Topoisomerase I or II inhibitors, such as respectively camptothecin and etoposide, and RNA/DNA antimetabolites, such as 5-fluorouracil.

However, it is observed that such agents present side effects, notably a phenomenon of resistance and the development of peripheral neuropathies. The development of new compounds with or without less side effects presents a considerable interest and improvement over existing drugs.

In addition to inhibitors aiming at MT assembly/dynamics and inhibitors targeting mitotic kinases, a new class of targets has emerged, that of kinesin based motor proteins.

Kinesins are proteins which use the free energy of ATP hydrolysis to drive intracellular movement and influence cytoskeleton organization (R. D. Vale and R. J. Fletterick, Annu. Rev. Cell. Dev. Biol. 13, 745-777 (1997)). More than 90 members of this family are known. In particular, a recent RNAi screen in human cells has identified at least 12 different members of such kinesin superfamily as being actively involved in cell division.

Several members of the kinesin superfamily play thus key roles in mitosis and some of them, such as MKLP-2, are essential for cytokinesis and more particularly for the implementation of the cleavage furrow and spindle midzone formation. Cytokinesis marks the final step of mitosis and the cell cycle, leading to the production of two daughter cells endowed with a complete set of chromosomes and cytoplasmic organelles.

Many steps of cytokinesis, from cleavage furrow and spindle midzone formation, to transport of proteins to the cell division plane as well as furrow ingression are thought to be dependent on the function of different members of the kinesin superfamily, including Mitotic-Kinesin-Like-Protein-1 (MKLP-1) and -2 (MKLP-2), M-Phase-Phosphoprotein-1 (MPP1), human KIF4A (and its with 99% identity very close homologue Kif4B, both kinesin-4 family) and KIF14. Another protein is Eg5 which would drive the movement of microtubules in vitro.

Inhibitors of kinesin has been already reported (R. Sakowicz et al., Science 280, 292-295 (1998)) or disclosed, notably in U.S. Pat. No. 6,489,134 and U.S. Pat. No. 6,890,933, but such inhibitors seems not to be selective for different kinesin. However, they do not show a potential efficiency against MKLP-2.

MKLP-2, also called RabK6, RB6K, Rab6KIFL, Rabkinesin6 and KIF20A, has been shown to be essential for normal cleavage furrow ingression and cytokinesis. Overexpression of exogenously expressed MKLP-2 leads to cell division defects and subsequent cell death. Depletion of MKLP-2 by siRNA leads to binucleated cells. Accordingly, it can thus constitute new target for the development of novel therapeutic strategies against cancers or diseases linked to uncontrolled and/or abnormal growth of cells.

Thus currently there is a lack of inhibitors being competent for this specific member of the kinesin family in order to be used as a selective anti-mitotic agent and thus as an anticancer and anti-tumorigenic compound and being furthermore without side effects.

The inventors have herein demonstrated that some derivatives of indole are effective inhibitors for MKLP-2. As shown hereafter, they suppress the basal ATPase activity of MKLP-2 in a specific manner. Accordingly, such compounds may serve as lead compound of a new generation of inhibitors of cytokinesis.

The present invention relates to the use of a compound of formula (I):

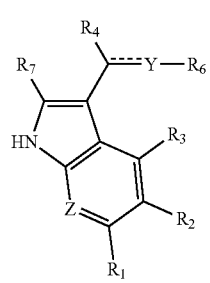

for the manufacture of a pharmaceutical composition intended for the treatment of cancer.

Some of the compounds of formula (I) are already known, namely various compounds of formula (I) have already disclosed in Dieng C. et al., P. J. Heterocycl. Chem. (1975) 12, 455-460, Efremova T. et al., Khim. Geterotsikl. Soedin (1974), 1382-7, Chevolot L. et al., Bull. Soc. Chim. Fr. (1976), 1222-6, Mallory F. B. et al., Org. React. (Hoboken, N.J., U.S.) (1984), 30, or commercially available from Ambinter, Aurora Fine Chemicals LLC, Interchim or Maybridge Ryan Scientific, Inc.

However, to the knowledge of the inventors, these compounds have never been proposed as inhibitor of kinesin, in particular of MKLP-2.

Unexpectedly, the inventors identified that compounds according to formula (I) possess a powerful anti-mitotic activity and inhibit specifically the kinesin MKLP-2 without side effects. Such compounds have an effective anticancer power with, at the same time, low toxicity.

Accordingly, the present invention relates to the use of a compound of formula (I):

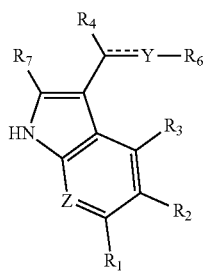

(I)

wherein:
  the dashed line --- represents a saturated or an insaturated bond;
  Z represents a CH unit or a nitrogen atom;
  Y represents a $C(R_5)_x$ unit or a nitrogen atom, with when Y represents a nitrogen atom, then the dashed line represents an unsaturated bond;
  $R_5$ represents a hydrogen atom, a $(C_1-C_5)$alkyl, a nitrile, a carboxamide or Ar group, with x being 1 or 2;
  $R_6$ represents a hydrogen atom, a $(C_1-C_5)$alkyl or an Ar group;
  $R_4$ represents a hydrogen atom, a nitrile, an ethyne, a $(C_1-C_5)$alkyl or a carboxamide group;
provided that:
  when $R_4$ represents a hydrogen atom and Y represents a $C(R_5)$ unit, then $R_5$ represents a nitrile group or a hydrogen atom and $R_6$ represents an Ar group, and
  when $R_4$ is different from an hydrogen atom and Y represents a $C(R_5)$ unit, then one of $R_5$ and $R_6$, different the one of the other, is an Ar group;
  $R_7$ represents a hydrogen atom or a $(C_1-C_5)$alkyl group;
  $R_1$, $R_2$ and $R_3$, independently the ones of the others, represent a hydrogen atom, a halogen, a hydroxyl, an amine or a radical $(C_1-C_{10})$alkoxy, phenyl, benzyloxy, acetate, methylcarbamate, $(C_1-C_{10})$alkoxyacetate, said radical being optionally substituted by at least one halogen or a $(C_1-C_{10})$alkoxy group;
  $R_2$ and $R_3$ may form with the phenyl cycle a condensed heterocycle, like for example a benzoxazole, optionally substituted by a $(C_1-C_5)$alkyl group;
  Ar represents an aromatic radical selected among:

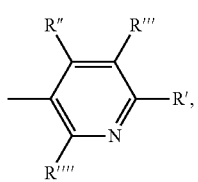

(A)

with R' represents a hydrogen atom, a halogen, a cyano, a $(C_1-C_5)$alkyl or a $(C_1-C_{10})$alkoxy group,
R" and R"", independently the one of the other, represent a hydrogen atom, a halogen or a $(C_1-C_5)$alkyl group, and
R"' represents a hydrogen atom or a $(C_1-C_{10})$alkoxy group;

(B)

provided that when Ar is (B), Y represents a $C(R_5)_x$ unit, Z represents a CH unit, $R_4$ represents a nitrile group and $R_1$, $R_3$, $R_5$ and $R_7$ represent a hydrogen atom and:
  if the dashed line is an unsaturated bond, then $R_2$ is different from a benzyloxy group, or
  if the dashed line is a saturated bond, then $R_2$ is different from a hydrogen atom;

(C)

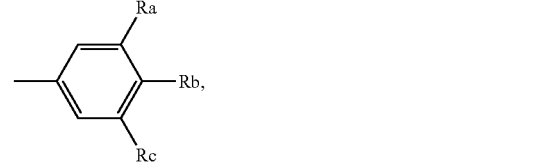

(D)

with:
  Ra and Rc, independently the one of the other, represent a hydrogen atom, a halogen, a nitro, a nitrile, an amine, an amide or a $(C_1-C_5)$alkoxy group;
  Rb represents a hydrogen atom, a halogen or a hydroxyl group;
  Rb and Rc may form with the aromatic cycle a condensed saturated cycle in $C_5$, if necessary interrupted by one or several heteroatom;
provided that:
  when Ar is (D) with Ra and Rc representing a methoxy group (—$OCH_3$), Y represents a $C(R_5)_1$ unit, Z represents a CH unit and $R_1$, $R_3$, $R_5$ and $R_7$ represent a hydrogen atom, $R_4$ represents a nitrile group and Rb represents a hydroxyl group, then $R_2$ is different from a hydrogen atom; and
  when Ar is (D) with Ra, Rb, $R_1$, $R_2$, $R_3$, $R_5$ and $R_7$ represent a hydrogen atom, Y represents a $C(R_5)_1$ unit, $R_4$ represents a nitrile group and Z represents a CH unit, then Rc is different from a methoxy group (—$OCH_3$);

(E)

(F)

with $R_8$ represents a hydrogen atom or a $(C_1-C_5)$alkyl group; or one of its pharmaceutically acceptable salts,
for the manufacture of a pharmaceutical composition intended for the treatment of cancer.

The derivatives of formula (I) can be used for treatment or prevention.

As used herein, the term "cancer" or "cancerous growth" means the uncontrolled, abnormal growth of cells and includes within its scope all the well known diseases that are caused by the uncontrolled and abnormal growth of cells. Non-limiting examples of common cancers include bladder cancer, breast cancer, ovarian cancer, pancreatic cancer, and gastric cancer, cervical cancer, colon cancer, endometrial cancer, head and neck cancer, lung cancer, melanoma, multiple myeloma, leukemia (e.g. myeloid, lymphocytic, myelocytic and lymphoblastic leukemias), non-hodgkin's lymphoma, prostate cancer, rectal cancer, and malignant melanomas.

In still other embodiments, a compound according to the invention is also active against solid tumors and also kills and/or inhibits the growth of multidrug resistant cells (MDR cells).

The compounds of formula (I) can comprise one or more asymmetrical carbon atoms. They can thus exist in the form of enantiomers or of diastereoisomers. These enantiomers, diastereoisomers, as their mixtures, including the racemic mixtures form part of the invention.

The compounds of formula (I) may comprise an unsaturation site and thus may be in their tautomeric form. The instant invention also extends to the compounds of formula (I) in their tautomeric form.

The compounds of formula (I) can be provided in the form of a free base or in the form of addition salts with acids, which also form part of the invention.

These salts can be prepared with pharmaceutically acceptable acids, but salts with other acids, useful for example for the purification or for the isolation of the compounds of formula (I), also form part of the invention.

It may be also a salt with the nitrogen atom of pyridine group as Ar for $R_6$ as illustrated by the compound (Z)-3-[2-cyano-2-(5-methoxy-1H-indol-3-yl)-vinyl]-1-methylpyridinium iodide.

The compounds of formula (I) can also exist in the form of a hydrate or of a solvate, i.e. in the form of associations or combinations with one or more water or solvent molecules. Such hydrates and solvates also form part of the invention.

According to the present invention, the terms below have the following meanings:

The terms mentioned herein with prefixes such as for example $C_1$-$C_5$ or $C_1$-$C_{10}$ can also be used with lower numbers of carbon atoms such as $C_1$-$C_3$ or $C_1$-$C_7$. If for example the term $C_1$-$C_5$ is used, it means that the corresponding hydrocarbon chain may comprise from 1 to 5 carbon atoms. If for example the term $C_3$-$C_8$ is used, it means that the corresponding hydrocarbon chain or cycle may comprise from 3 to 8 carbon atoms.

The term "halogen atom" corresponds to a fluorine, chlorine, bromine or iodine atom.

Fluorine and chlorine are preferred halogen atoms in the framework of the present invention.

The term "alkyl" as used herein refers to a saturated, linear or branched aliphatic group. The following examples may be cited: methyl, ethyl, 1-propyl, 2-propyl, 1-butyl, 2-methyl-1-propyl (also named i-Bu), 2-butyl (also named s-Bu), 2-methyl-2-propyl (also named t-Bu), 1-pentyl (also named n-pentyl), 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl. Preferred alkyl according to the invention are methyl, ethyl, 1-propyl, 2-propyl, 1-butyl, 2-methyl-1-propyl (also named i-Bu), 2-butyl (also named s-Bu), 2-methyl-2-propyl (also named t-Bu), 1-pentyl (also named n-pentyl), 2-pentyl, 3-pentyl, 2-methyl-2-butyl, 3-methyl-2-butyl, 3-methyl-1-butyl, 2-methyl-1-butyl.

The term "alkoxy" corresponds to a —O-alkyl group, wherein the alkyl group is as defined above. The following examples may be cited: methoxy, ethoxy, propoxy, isopropoxy.

The term "aryl" as used herein means an aromatic mono- or poly-cyclic group. An example of monocyclic group may be phenyl.

The term "heteroaryl" as used herein corresponds to an aromatic, mono- or poly-cyclic group comprising between 5 and 14 carbon atoms and comprising at least one heteroatom such as nitrogen, oxygen or sulphur atom. Examples of such mono- and poly-cyclic heteroaryl group may be: pyridyl, dihydroypyridyl, thiazolyl, thiophenyl, furanyl, azocinyl, pyranyl, pyrrolyl, pyrazolyl, imidazolyl, tetrazolyl, benzofuranyl, thianaphthalenyl, indolyl, indolenyl, quinolinyl, isoquinolinyl, benzimidazolyl, pyrrolinyl, tetrahydroquinolinyl, tetrahydroisoquinolinyl, triazinyl, 6H-1,2,5-thiadiazinyl, 2H,6H-1,5,2-dithiazinyl, thianthrenyl, isobenzofuranyl, chromenyl, xanthenyl, phenoxanthinyl, 2H-pyrrolyl, isothiazolyl, isoxazolyl, pyrazinyl, pyridazinyl, indolizinyl, isoindolyl, 3H-indolyl, 1H-indazolyl, purinyl, 4H-quinolizinyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, indolinyl, isoindolinyl, oxazolidinyl, benzotriazolyl, benzisoxazolyl, oxindolyl, benzoxazolinyl, benzothienyl, benzothiazolyl, isatinyl, pyridyl, dihydropyridyl, pyrimidinyl, pyrazinyl, s-triazinyl, oxazolyl, thiofuranyl.

Rings as defined above may be bonded through a carbon atom or a heteroatom, if any.

By way of example, when they are bonded through a carbon atom, they are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example, when they are bonded through an heteroatom such as nitrogen, nitrogen bonded heterocyclic rings are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. Still more typically, nitrogen bonded heterocycles include 1-aziridyl, 1-azetedyl, 1-pyrrolyl, 1-imidazolyl, 1-pyrazolyl, and 1-piperidinyl.

Regardless of bond indications, if a substituent is polyvalent (based on its position in the structure referred to), then any and all possible orientations of the substituent are intended.

Among the compound of formula (I) defined above, the compounds for which the use is preferred may be given in details as follows.

According to a preferred embodiment of the invention, Y represents a $C(R_5)_x$ unit.

According to another preferred embodiment of the invention, Z represents a CH unit.

According to another preferred embodiment of the invention, when Y represents a $C(R_5)_x$ unit, then $R_4$ is different from $R_5$.

According to another preferred embodiment of the invention, when $R_6$ is an Ar group represented by an aromatic cycle in $C_5$ such as above-mentioned, said aromatic cycle in $C_5$ is advantageously chosen from a thiophene or a pyrazole group, optionally substituted by at least one $(C_1-C_5)$alkyl group, and in particular by a methyl group.

More particularly, a compound of formula (I) may be represented by a compound of formula (II):

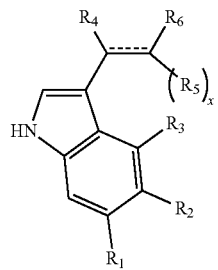

(II)

wherein:
$R_4$ represents a hydrogen atom or a nitrile group;
$R_5$, different from $R_4$, represents a hydrogen atom, a $(C_1-C_5)$alkyl, a nitrile or Ar group, with x being 1 or 2;
$R_6$ represents a hydrogen atom, a $(C_1-C_5)$alkyl or an Ar group;
provided that:
when $R_4$ represents a hydrogen atom, then $R_5$ represents a nitrile group and $R_6$ represents an Ar group, and
when $R_4$ represents a nitrile group, then one of $R_5$ and $R_6$, different the one of the other, is an Ar group;
the dashed line --- represents a saturated or an unsaturated bond;
$R_1$, $R_2$ and $R_3$, independently the ones of the others, represent a hydrogen atom, a halogen, a hydroxyl, a $(C_1-C_{10})$alkoxy, a benzyloxy, an acetate or a $(C_1-C_{10})$alkoxyacetate group;
Ar represents an aromatic radical such as an aryl or a heteroaryl group more particularly selected among:

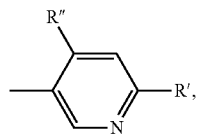

(A')

wherein R' represents a hydrogen atom or a halogen, and R" represents a hydrogen atom or a $(C_1-C_5)$alkyl group; and

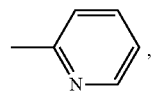

(B')

provided that, when Ar is (B') and $R_1$, $R_3$ and $R_5$ represent a hydrogen atom:
if the dashed line is an unsaturated bond, then $R_2$ is different from a benzyloxy group, or
if the dashed line is a saturated bond, then $R_2$ is different from a hydrogen atom;

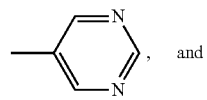

(C')

and

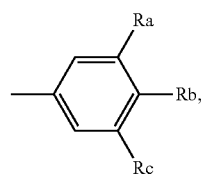

(D')

with:
Ra and Rc, independently the one of the other, represent a hydrogen atom, a halogen, a nitrile, an amide or a $(C_1-C_5)$alkoxy group;
Rb represents a hydrogen atom, a halogen or a hydroxyl group;
Rb and Rc may form with the aromatic cycle a condensed saturated cycle in $C_5$, if necessary interrupted by one or several heteroatom;
provided that:
when Ar is (D') with Ra and Rc representing a methoxy group (—$OCH_3$), x is 1 and $R_1$, $R_3$ and $R_5$ represent a hydrogen atom and Rb represents a hydroxyl group, then $R_2$ is different from a hydrogen atom; and
when Ra, Rb, $R_1$, $R_2$, $R_3$ and $R_5$ represent a hydrogen atom and x is 1, then Rc is different from a methoxy group (—$OCH_3$)
or one of its pharmaceutically acceptable salts,
for the manufacture of a pharmaceutical composition intended for the treatment of cancer.

According to a particular embodiment of the invention, when the dashed line is a saturated bond, Ar differs preferably from (B').

According to another embodiment, a compound of formula (I) may be represented by a compound of formula (III):

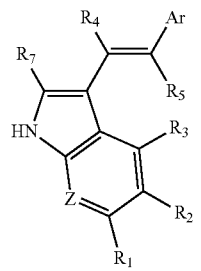

(III)

wherein $R_1$, $R_2$, $R_3$, $R_4$, $R_5$, $R_7$, Z and Ar are as previously defined for compounds of formula (I).

Among the compounds of formula (I) or (III), the compounds for which the therapeutical use is particularly interesting are characterized in that $R_4$ represents a nitrile or a carboxamide group and $R_5$ and $R_7$ represent a hydrogen atom.

In particular, they are characterized in that $R_4$ represents a nitrile group and $R_5$ and $R_7$ represent a hydrogen atom.

Among the compounds of formula (I) or (III), a preferred embodiment of the instant invention encompasses a group of compounds of formula (I) or (III) wherein Ar represents:

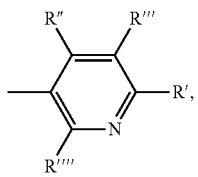

(A)

like
in particular (A'):

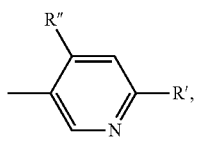

(A')

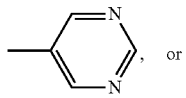

(C)

or

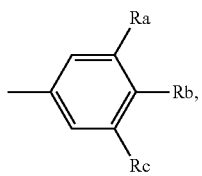

(D)

wherein R', R", R'", R"", Ra, Rb and Rc are as previously defined.

In another preferred embodiment, a group of compounds of formula (I), (II) or (III) is defined such as Ar represents:

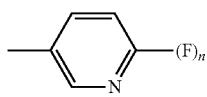

wherein n represents 0 or 1, and in particular represents 0.

In still yet another preferred embodiment, a group of compounds of formula (I), (II) or (III) is defined such as Ar represents:

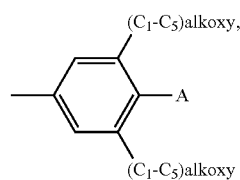

(a)

wherein A represents a hydrogen atom or a hydroxyl group;

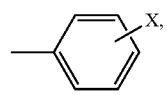

(b)

wherein X represents a halogen selected among fluorine and chlorine in meta or in para or a nitrile group in meta; or

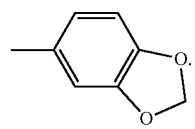

(c)

Among the compounds of formula (I), (II) or (III), a preferred embodiment of the instant invention encompasses a group of compounds of formula (I), (II) or (III) wherein:
$R_1$, $R_2$ and $R_3$ represent a hydrogen atom; or
$R_1$ and $R_3$ represent a hydrogen atom and $R_2$ is different from a hydrogen atom, or
$R_1$ and $R_2$ represent a hydrogen atom and $R_3$ is different from a hydrogen atom, or
$R_2$ and $R_3$ represent a hydrogen atom and $R_1$ is different from a hydrogen atom, or
$R_1$ represents a hydrogen atom and $R_2$ and $R_3$ are different from a hydrogen atom, or
$R_2$ represents a hydrogen atom and $R_1$ and $R_3$ are different from a hydrogen atom, or
$R_3$ represents a hydrogen atom and $R_1$ and $R_2$ are different from a hydrogen atom.

Among the compounds according to the instant invention, the following list of compounds may be cited:
(Z)-2-(5-methoxy-1H-indol-3-yl)-3-pyridin-3-yl-acrylonitrile;
(Z)-2-(5-ethoxy-1H-indol-3-yl)-3-pyridin-3-yl-acrylonitrile;
(Z)-2-(5-isopropoxy-1H-indol-3-yl)-3-pyridin-3-yl-acrylonitrile;
(Z)-2-(5-chloro-1H-indol-3-yl)-3-pyridin-3-yl-acrylonitrile;
(Z)-2-(5-fluoro-1H-indol-3-yl)-3-pyridin-3-yl-acrylonitrile;
(Z)-2-(4-methoxy-1H-indol-3-yl)-3-pyridin-3-yl-acrylonitrile;
(Z)-3-(6-fluoropyridin-3-yl)-2-(5-methoxy-1H-indol-3-yl)-acrylonitrile;
(Z)-2-(6-methoxy-1H-indol-3-yl)-3-pyridin-3-yl-acrylonitrile;
(Z)-2-(1H-indol-3-yl)-3-pyrimidin-5-yl-acrylonitrile;
(Z)-2-(5-methoxy-1H-indol-3-yl)-3-pyrimidin-5-yl-acrylonitrile;
(Z)-3-(1-cyano-2-(pyridin-3-yl)vinyl)-1H-indol-5-yl-acetate;

(Z)-3-(1-cyano-2-(pyridin-3-yl)vinyl)-1H-indol-5-yl 2-methoxyacetate;
(Z)-2-(5-benzyloxy-1H-indol-3-yl)-3-pyridin-3-yl-acrylonitrile;
(Z)-2-(1H-indol-3-yl)-3-pyridin-3-yl-acrylonitrile;
(Z)-3-(3,5-dimethoxy-phenyl)-2-(5-methoxy-1H-indol-3-yl)-acrylonitrile;
(Z)-3-(3,5-dimethoxy-phenyl)-2-(1H-indol-3-yl)-acrylonitrile;
(Z)-3-(4-chloro-phenyl)-2-(1H-indol-3-yl)-acrylonitrile;
(Z)-2-(5-methoxy-1H-indol-3-yl)-3-pyridin-3-yl-propionitrile;
(Z)-3-benzo[1,3]dioxol-5-yl-2-(1H-indol-3-yl)-acrylonitrile;
(Z)-3-(1H-indol-3-yl)-2-pyridin-3-yl-acrylonitrile;
(Z)-3-(4-fluoro-phenyl)-2-(1H-indol-3-yl)-acrylonitrile;
(Z)-2-(5-methoxy-1H-indol-3-yl)-3-pyridin-2-yl-acrylonitrile;
(Z)-3-(3-chloro-phenyl)-2-(1H-indol-3-yl)-acrylonitrile;
(Z)-3-(4-hydroxy-3,5-dimethoxy-phenyl)-2-(5-methoxy-1H-indol-3-yl)-acrylonitrile;
(Z)-2-(1H-indol-3-yl)-3-phenyl-acrylonitrile;
(Z)-2-(1H-indol-3yl-)-3-pyridin-3-yl-propionitrile;
(Z)-2-(1H-indol-3-yl)-3-pyridin-2-yl-acrylonitrile;
(E)-2-(1H-indol-3-yl)-3-pyridin-3-yl-acrylonitrile;
(Z)-2-(5-hydroxy-1H-indol-3-yl)-3-pyridin-3-yl-acrylonitrile;
(Z)-3-[2-cyano-2-(5-methoxy-1H-indol-3-yl)-vinyl]-benzonitrile;
(Z)-2-(5-methoxy-1H-indol-3-yl)-3-(4-methyl-pyridin-3-yl)-acrylonitrile;
(Z)-3-[2-cyano-2-(5-methoxy-1H-indol-3-yl)-vinyl]-benzamide;
(Z)-3-[2-cyano-2-(5-methoxy-1H-indol-3-yl)-vinyl]-1-methylpyridinium iodide;
(Z)-2-(2-propyl-6H-oxazolo[4,5-e]indol-8-yl)-3-(pyridin-3-yl)acrylonitrile;
(Z)-2-(5-methoxy-2-methyl-1H-indol-3-yl)-3-pyridin-3-yl-acrylonitrile;
(Z)-3-(pyridin-3-yl)-2-(1H-pyrrolo[2,3-b]pyridin-3-yl)-acrylonitrile;
(Z)-2-(5-bromo-1H-indol-3-yl)-3-pyridin-3-yl-acrylonitrile;
(Z)-3-(pyridin-3-yl)-2-(5-(3,4,5-trimethoxyphenyl)-1H-indol-3-yl)-acrylonitrile;
(Z)-2-(5-(4-fluorophenyl)-1H-indol-3-yl)-3-(pyridin-3-yl)-acrylonitrile;
(Z)-2-(5-amino-1H-indol-3-yl)-3-pyridin-3-yl-acrylonitrile;
(Z)-methyl 3-(1-cyano-2-(pyridin-3-yl)vinyl)-1H-indol-5-ylcarbamate;
(Z)-2-(1H-indol-3-yl)-3-(3-nitro-phenyl)-acrylonitrile;
(Z)-2-(5-methoxy-1H-indol-3-yl)-3-(3-nitro-phenyl)-acrylonitrile;
(Z)-3-(3-amino-phenyl)-2-(1H-indol-3-yl)-acrylonitrile;
(Z)-3-(3-amino-phenyl)-2-(5-methoxy-1H-indol-3-yl)-acrylonitrile;
(Z)-2-(5-methoxy-1H-indol-3-yl)-3-(5-methoxy-pyridin-3-yl)-acrylonitrile;
(Z)-3-(4-chloro-pyridin-3-yl)-2-(5-methoxy-1H-indol-3-yl)-acrylonitrile;
(Z)-3-(2-fluoropyridin-3-yl)-2-(5-methoxy-1H-indol-3-yl)-acrylonitrile;
(Z)-3-(6-chloropyridin-3-yl)-2-(5-methoxy-1H-indol-3-yl)-acrylonitrile;
(Z)-2-(5-methoxy-1H-indol-3-yl)-3-thiophen-3-yl-acrylonitrile;
(Z)-2-(5-methoxy-1H-indol-3-yl)-3-(1-methyl-1H-pyrazol-3-yl)-acrylonitrile;
(Z)-3-(6-methoxy-pyridin-3-yl)-2-(5-methoxy-1H-indol-3-yl)-acrylonitrile;
(Z)-2-(5-methoxy-1H-indol-3-yl)-3-(6-methylpyridin-3-yl)-acrylonitrile;
(Z)-5-[2-cyano-2-(5-methoxy-1H-indol-3-yl)-vinyl]-picolinonitrile;
(Z)-3-[2-cyano-2-(5-hydroxy-1H-indol-3-yl)-vinyl]-benzonitrile;
(Z)-2-(1H-indol-3-yl)-3-pyridin-3-yl-acrylamide;
(E)-3-(2-pyridin-3-yl-vinyl)-1H-indole;
(E)-5-methoxy-3-(1-(pyridin-3-yl)but-1-en-3-yn-2-yl)-1H-indole;
5-methoxy-3-(1-(pyridin-3-yl)prop-1-en-2-yl)-1H-indole;
(Z)-2-(5-methoxy-1H-indol-3-yl)-3-(pyridin-3-yl)-but-2-enenitrile;
(Z)-(1H-indol-3-yl)-(pyridin-3-ylimino)-acetonitrile;
and their pharmaceutically acceptable salts.

More preferably, the following list of compounds may be cited:
(Z)-2-(5-methoxy-1H-indol-3-yl)-3-pyridin-3-yl-acrylonitrile;
(Z)-2-(5-ethoxy-1H-indol-3-yl)-3-pyridin-3-yl-acrylonitrile;
(Z)-2-(5-isopropoxy-1H-indol-3-yl)-3-pyridin-3-yl-acrylonitrile;
(Z)-2-(5-chloro-1H-indol-3-yl)-3-pyridin-3-yl-acrylonitrile;
(Z)-2-(5-fluoro-1H-indol-3-yl)-3-pyridin-3-yl-acrylonitrile;
(Z)-2-(4-methoxy-1H-indol-3-yl)-3-pyridin-3-yl-acrylonitrile;
(Z)-3-(6-fluoropyridin-3-yl)-2-(5-methoxy-1H-indol-3-yl)-acrylonitrile;
(Z)-2-(6-methoxy-1H-indol-3-yl)-3-pyridin-3-yl-acrylonitrile;
(Z)-2-(1H-indol-3-yl)-3-pyrimidin-5-yl-acrylonitrile;
(Z)-2-(5-methoxy-1H-indol-3-yl)-3-pyrimidin-5-yl-acrylonitrile;
(Z)-3-(1-cyano-2-(pyridin-3-yl)vinyl)-1H-indol-5-yl-acetate;
(Z)-3-(1-cyano-2-(pyridin-3-yl)vinyl)-1H-indol-5-y 2l-methoxyacetate;
(Z)-2-(1H-indol-3-yl)-3-pyridin-3-yl-acrylonitrile;
(Z)-2-(5-hydroxy-1H-indol-3-yl)-3-pyridin-3-yl-acrylonitrile;
(Z)-3-[2-cyano-2-(5-methoxy-1H-indol-3-yl)-vinyl]-benzonitrile;
(Z)-2-(5-methoxy-1H-indol-3-yl)-3-(4-methyl-pyridin-3-yl)-acrylonitrile;
(Z)-3-(pyridin-3-yl)-2-(5-(3,4,5-trimethoxyphenyl)-1H-indol-3-yl)-acrylonitrile;
(Z)-methyl 3-(1-cyano-2-(pyridin-3-yl)vinyl)-1H-indol-5-ylcarbamate;
(Z)-3-(4-chloro-pyridin-3-yl)-2-(5-methoxy-1H-indol-3-yl)-acrylonitrile;
(Z)-2-(5-methoxy-1H-indol-3-yl)-3-(6-methylpyridin-3-yl)-acrylonitrile;
(Z)-3-[2-cyano-2-(5-hydroxy-1H-indol-3-yl)-vinyl]-benzonitrile;
5-methoxy-3-(1-(pyridin-3-yl)prop-1-en-2-yl)-1H-indole;
(Z)-2-(5-methoxy-1H-indol-3-yl)-3-(pyridin-3-yl)-but-2-enenitrile;
(Z)-(1H-indol-3-yl)-(pyridin-3-ylimino)-acetonitrile;
and their pharmaceutically acceptable salts.

More preferably, the following list of compounds may be cited:
(Z)-2-(5-methoxy-1H-indol-3-yl)-3-pyridin-3-yl-acrylonitrile;

(Z)-2-(5-ethoxy-1H-indol-3-yl)-3-pyridin-3-yl-acrylonitrile;
(Z)-2-(5-isopropoxy-1H-indol-3-yl)-3-pyridin-3-yl-acrylonitrile;
(Z)-2-(5-chloro-1H-indol-3-yl)-3-pyridin-3-yl-acrylonitrile;
(Z)-2-(5-fluoro-1H-indol-3-yl)-3-pyridin-3-yl-acrylonitrile;
(Z)-2-(4-methoxy-1H-indol-3-yl)-3-pyridin-3-yl-acrylonitrile;
(Z)-3-(6-fluoropyridin-3-yl)-2-(5-methoxy-1H-indol-3-yl)-acrylonitrile;
(Z)-2-(6-methoxy-1H-indol-3-yl)-3-pyridin-3-yl-acrylonitrile;
(Z)-2-(1H-indol-3-yl)-3-pyrimidin-5-yl-acrylonitrile;
(Z)-2-(5-methoxy-1H-indol-3-yl)-3-pyrimidin-5-yl-acrylonitrile;
(Z)-3-(1-cyano-2-(pyridin-3-yl)vinyl)-1H-indol-5-yl-acetate;
(Z)-3-(1-cyano-2-(pyridin-3-yl)vinyl)-1H-indol-5-yl 2-methoxyacetate;
(Z)-2-(1H-indol-3-yl)-3-pyridin-3-yl-acrylonitrile;
(Z)-2-(5-hydroxy-1H-indol-3-yl)-3-pyridin-3-yl-acrylonitrile;
(Z)-3-[2-cyano-2-(5-methoxy-1H-indol-3-yl)-vinyl]-benzonitrile;
(Z)-2-(5-methoxy-1H-indol-3-yl)-3-(4-methyl-pyridin-3-yl)-acrylonitrile;
(Z)-methyl 3-(1-cyano-2-(pyridin-3-yl)vinyl)-1H-indol-5-ylcarbamate;
5-methoxy-3-(1-(pyridin-3-yl)prop-1-en-2-yl)-1H-indole;
(Z)-(1H-indol-3-yl)-(pyridin-3-ylimino)-acetonitrile,
and their pharmaceutically acceptable salts.

The invention further relates to compounds of general formula (IV):

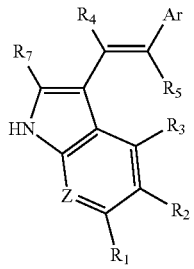

in which:
Z represents a CH unit or a nitrogen atom;
$R_4$ and $R_5$, different the one of the other, with:
  $R_4$ represents a hydrogen atom, a nitrile, an ethyne, a $(C_1$-$C_5)$alkyl or a carboxamide group;
  —$R_5$ represents a hydrogen atom, a $(C_1$-$C_5)$alkyl, a nitrile or a carboxamide group;
$R_7$ represents a hydrogen atom or a $(C_1$-$C_5)$alkyl group;
$R_1$, $R_2$ and $R_3$, independently, represent a hydrogen atom, a halogen, a hydroxyl, an amine, or a radical $(C_1$-$C_5)$ alkoxy, phenyl, benzyloxy, acetate, methylcarbamate, $(C_1$-$C_{10})$alkoxyacetate, said radical being optionally substituted by at least one halogen or a $(C_1$-$C_{10})$alkoxy group;
$R_2$ and $R_3$ may form with the phenyl cycle a condensed heterocycle, like for example a benzoxazole, optionally substituted by a $(C_1$-$C_5)$alkyl group;

Ar represents an aromatic radical selected among:

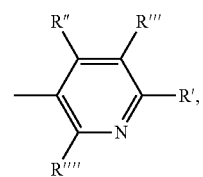

(A″)

with R' represents a hydrogen atom, a halogen, a cyano, a $(C_1$-$C_5)$alkyl or a $(C_1$-$C_{10})$alkoxy group,
R″ and R″″, independently the one of the other, represent a hydrogen atom, a halogen or a $(C_1$-$C_5)$alkyl group, and
R‴ represents a hydrogen atom or a $(C_1$-$C_{10})$alkoxy group;

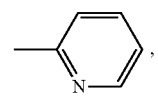

(B″)

provided that, when Ar is (B″), Z represents a CH unit and $R_1$, $R_3$, $R_5$ and $R_7$ represent a hydrogen atom and $R_4$ represents a nitrile group, then $R_2$ is different from a hydrogen atom;

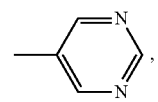

(C″)

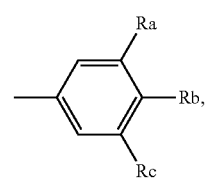

(D″)

with:
Ra and Rc, independently the one of the other, represent a hydrogen atom, a chloride, a nitro, a nitrile, an amine, an amide or a $(C_1$-$C_5)$alkoxy group; and
Rb represents a hydrogen atom, a chloride or a hydroxyl group,
provided that:
when $R_1$, $R_2$, $R_3$, $R_5$ and $R_7$ represent a hydrogen atom, $R_4$ represents a nitrile group and Z represents a CH unit, then at least one moieties among Ra, Rb and Rc is different from a hydrogen atom, and
when Ra and Rc represent a methoxy group (—OCH$_3$), Z represents a CH unit, $R_4$ represents a nitrile group and $R_1$, $R_3$, $R_5$ and $R_7$ represent a hydrogen atom, if Rb represents a hydroxyl group, then $R_2$ is different from a hydrogen atom; and
when Ra, Rb, Rc, $R_1$, $R_2$, $R_3$ and $R_7$ represent a hydrogen atom, Z represents a CH unit and $R_5$ represents a nitrile group, then $R_4$ is different from a hydrogen atom.

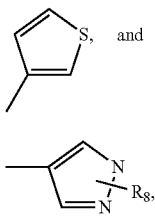 (E″)

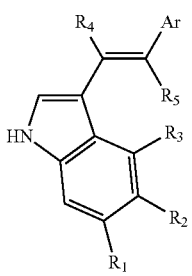 (F″)

with $R_8$ represents a hydrogen atom or a $(C_1-C_5)$alkyl group;
with the compound of formula (IV) being different from (Z)-2-(1H-indol-3-yl)-3-pyridin-3-yl-acrylonitrile,
and their pharmaceutically acceptable salts.

More particularly, a compound of formula (IV) may be represented by a compound of formula (V):

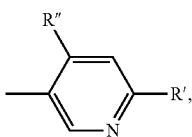 (V)

in which:
$R_4$ and $R_5$, different the one of the other, represent a hydrogen atom or a nitrile group;
$R_1$, $R_2$ and $R_3$, independently, represent a hydrogen atom, a halogen, a hydroxyl, a $(C_1-C_5)$alkoxy, a benzyloxy, an acetate or a $(C_1-C_{10})$alkoxyacetate group;
Ar represents an aromatic radical selected among:

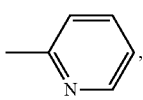 (A‴)

with R' represents a hydrogen atom or a halogen, and R″ represents a hydrogen atom or a $(C_1-C_5)$alkyl group;

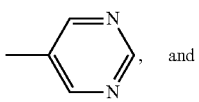 (B‴)

provided that, when Ar is (B‴) and $R_1$, $R_3$ and $R_5$ represent a hydrogen atom, then $R_2$ is different from a hydrogen atom;

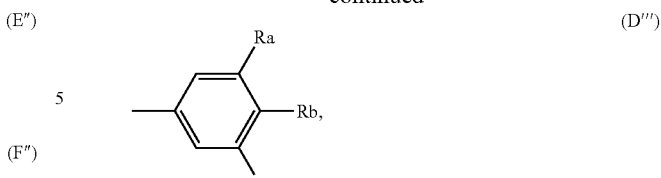 (C‴) and (D‴)

with:
Ra and Rc, independently the one of the other, represent a hydrogen atom, a chloride, a nitrile, an amide or a $(C_1-C_5)$alkoxy group; and
Rb represents a hydrogen atom, a chloride or a hydroxyl group,
provided that:
when $R_1$, $R_2$, $R_3$, $R_5$ is a hydrogen atom, at least one moieties among Ra, Rb and Rc is different from a hydrogen atom, and
when Ra and Rc represent a methoxy group (—$OCH_3$) and $R_1$, $R_3$ and $R_5$ represent a hydrogen atom, if Rb represents a hydroxyl group, then $R_2$ is different from a hydrogen atom;
when Ra, Rb, Rc, $R_1$, $R_2$ and $R_3$ represent a hydrogen atom and $R_5$ represents a nitrile group, then $R_4$ is different from a hydrogen atom; and
with the compound of formula (V) being different from (Z)-2-(1H-indol-3-yl)-3-pyridin-3-yl-acrylonitrile,
and their pharmaceutically acceptable salts.

Among the compound of formula (IV) according to the instant invention, the following list of compounds may be cited:
(Z)-2-(5-methoxy-1H-indol-3-yl)-3-pyridin-3-yl-acrylonitrile;
(Z)-2-(5-ethoxy-1H-indol-3-yl)-3-pyridin-3-yl-acrylonitrile;
(Z)-2-(5-isopropoxy-1H-indol-3-yl)-3-pyridin-3-yl-acrylonitrile;
(Z)-2-(5-chloro-1H-indol-3-yl)-3-pyridin-3-yl-acrylonitrile;
(Z)-2-(5-fluoro-1H-indol-3-yl)-3-pyridin-3-yl-acrylonitrile;
(Z)-2-(4-methoxy-1H-indol-3-yl)-3-pyridin-3-yl-acrylonitrile;
(Z)-3-(6-fluoropyridin-3-yl)-2-(5-methoxy-1H-indol-3-yl)-acrylonitrile;
(Z)-2-(6-methoxy-1H-indol-3-yl)-3-pyridin-3-yl-acrylonitrile;
(Z)-2-(1H-indol-3-yl)-3-pyrimidin-5-yl-acrylonitrile;
(Z)-2-(5-methoxy-1H-indol-3-yl)-3-pyrimidin-5-yl-acrylonitrile;
(Z)-3-(1-cyano-2-(pyridin-3-yl)vinyl)-1H-indol-5-yl-acetate;
(Z)-3-(1-cyano-2-(pyridin-3-yl)vinyl)-1H-indol-5-yl 2-methoxyacetate;
(Z)-2-(5-benzyloxy-1H-indol-3-yl)-3-pyridin-3-yl-acrylonitrile;
(Z)-3-(3,5-dimethoxy-phenyl)-2-(1H-indol-3-yl)-acrylonitrile;
(Z)-3-(3,5-dimethoxy-phenyl)-2-(5-methoxy-1H-indol-3-yl)-acrylonitrile;
(Z)-3-(4-chloro-phenyl)-2-(1H-indol-3-yl)-acrylonitrile;
(Z)-2-(5-methoxy-1H-indol-3-yl)-3-pyridin-3-yl-propionitrile;
(Z)-3-(1H-indol-3-yl)-2-pyridin-3-yl-acrylonitrile;
(Z)-2-(5-methoxy-1H-indol-3-yl)-3-pyridin-2-yl-acrylonitrile;
(Z)-3-(3-chloro-phenyl)-2-(1H-indol-3-yl)-acrylonitrile;

(Z)-3-(4-hydroxy-3,5-dimethoxy-phenyl)-2-(5-methoxy-1H-indol-3-yl)-acrylonitrile;
(Z)-2-(5-hydroxy-1H-indol-3-yl)-3-pyridin-3-yl-acrylonitrile;
(Z)-3-[2-cyano-2-(5-methoxy-1H-indol-3-yl)-vinyl]-benzonitrile;
(Z)-2-(5-methoxy-1H-indol-3-yl)-3-(4-methyl-pyridin-3-yl)-acrylonitrile;
(Z)-3-[2-cyano-2-(5-methoxy-1H-indol-3-yl)-vinyl]-benzamide;
(Z)-3-[2-cyano-2-(5-methoxy-1H-indol-3-yl)-vinyl]-1-methylpyridinium iodide;
(Z)-2-(2-propyl-6H-oxazolo[4,5-e]indol-8-yl)-3-(pyridin-3-yl)acrylonitrile;
(Z)-2-(5-methoxy-2-methyl-1H-indol-3-yl)-3-pyridin-3-yl-acrylonitrile;
(Z)-3-(pyridin-3-yl)-2-(1H-pyrrolo[2,3-b]pyridin-3-yl)-acrylonitrile;
(Z)-2-(5-bromo-1H-indol-3-yl)-3-pyridin-3-yl-acrylonitrile;
(Z)-3-(pyridin-3-yl)-2-(5-(3,4,5-trimethoxyphenyl)-1H-indol-3-yl)-acrylonitrile;
(Z)-2-(5-(4-fluorophenyl)-1H-indol-3-yl)-3-(pyridin-3-yl)-acrylonitrile;
(Z)-2-(5-amino-1H-indol-3-yl)-3-pyridin-3-yl-acrylonitrile;
(Z)-methyl 3-(1-cyano-2-(pyridin-3-yl)vinyl)-1H-indol-5-ylcarbamate;
(Z)-2-(1H-indol-3-yl)-3-(3-nitro-phenyl)-acrylonitrile;
(Z)-2-(5-methoxy-1H-indol-3-yl)-3-(3-nitro-phenyl)-acrylonitrile;
(Z)-3-(3-amino-phenyl)-2-(1H-indol-3-yl)-acrylonitrile;
(Z)-3-(3-amino-phenyl)-2-(5-methoxy-1H-indol-3-yl)-acrylonitrile;
(Z)-2-(5-methoxy-1H-indol-3-yl)-3-(5-methoxy-pyridin-3-yl)-acrylonitrile;
(Z)-3-(4-chloro-pyridin-3-yl)-2-(5-methoxy-1H-indol-3-yl)-acrylonitrile;
(Z)-3-(2-fluoropyridin-3-yl)-2-(5-methoxy-1H-indol-3-yl)-acrylonitrile;
(Z)-3-(6-chloropyridin-3-yl)-2-(5-methoxy-1H-indol-3-yl)-acrylonitrile;
(Z)-2-(5-methoxy-1H-indol-3-yl)-3-thiophen-3-yl-acrylonitrile;
(Z)-2-(5-methoxy-1H-indol-3-yl)-3-(1-methyl-1H-pyrazol-3-yl)-acrylonitrile;
(Z)-3-(6-methoxy-pyridin-3-yl)-2-(5-methoxy-1H-indol-3-yl)-acrylonitrile;
(Z)-2-(5-methoxy-1H-indol-3-yl)-3-(6-methylpyridin-3-yl)-acrylonitrile;
(Z)-5-[2-cyano-2-(5-methoxy-1H-indol-3-yl)-vinyl]-picolinonitrile;
(Z)-3-[2-cyano-2-(5-hydroxy-1H-indol-3-yl)-vinyl]benzonitrile;
(Z)-2-(1H-indol-3-yl)-3-pyridin-3-yl-acrylamide;
(E)-5-methoxy-3-(1-(pyridin-3-yl)but-1-en-3-yn-2-yl)-1H-indole;
5-methoxy-3-(1-(pyridin-3-yl)prop-1-en-2-yl)-1H-indole;
(Z)-2-(5-methoxy-1H-indol-3-yl)-3-(pyridin-3-yl)-but-2-enenitrile;
(Z)-(1H-indol-3-yl)-(pyridin-3-ylimino)-acetonitrile;
and their pharmaceutically acceptable salts.

More preferably, the following list of compounds of formula (IV) may be cited:
(Z)-2-(5-methoxy-1H-indol-3-yl)-3-pyridin-3-yl-acrylonitrile;
(Z)-2-(5-ethoxy-1H-indol-3-yl)-3-pyridin-3-yl-acrylonitrile;
(Z)-2-(5-isopropoxy-1H-indol-3-yl)-3-pyridin-3-yl-acrylonitrile;
(Z)-2-(5-chloro-1H-indol-3-yl)-3-pyridin-3-yl-acrylonitrile;
(Z)-2-(5-fluoro-1H-indol-3-yl)-3-pyridin-3-yl-acrylonitrile;
(Z)-2-(4-methoxy-1H-indol-3-yl)-3-pyridin-3-yl-acrylonitrile;
(Z)-3-(6-fluoropyridin-3-yl)-2-(5-methoxy-1H-indol-3-yl)-acrylonitrile;
(Z)-2-(6-methoxy-1H-indol-3-yl)-3-pyridin-3-yl-acrylonitrile;
(Z)-2-(1H-indol-3-yl)-3-pyrimidin-5-yl-acrylonitrile;
(Z)-2-(5-methoxy-1H-indol-3-yl)-3-pyrimidin-5-yl-acrylonitrile;
(Z)-3-(1-cyano-2-(pyridin-3-yl)vinyl)-1H-indol-5-yl-acetate;
(Z)-3-(1-cyano-2-(pyridin-3-yl)vinyl)-1H-indol-5-yl 2-methoxyacetate;
(Z)-2-(5-hydroxy-1H-indol-3-yl)-3-pyridin-3-yl-acrylonitrile;
(Z)-3-[2-cyano-2-(5-methoxy-1H-indol-3-yl)-vinyl]-benzonitrile;
(Z)-2-(5-methoxy-1H-indol-3-yl)-3-(4-methyl-pyridin-3-yl)-acrylonitrile;
(Z)-3-(pyridin-3-yl)-2-(5-(3,4,5-trimethoxyphenyl)-1H-indol-3-yl)-acrylonitrile
(Z)-methyl 3-(1-cyano-2-(pyridin-3-yl)vinyl)-1H-indol-5-ylcarbamate;
(Z)-3-(4-chloro-pyridin-3-yl)-2-(5-methoxy-1H-indol-3-yl)-acrylonitrile;
(Z)-2-(5-methoxy-1H-indol-3-yl)-3-(6-methylpyridin-3-yl)-acrylonitrile;
(Z)-3-[2-cyano-2-(5-hydroxy-1H-indol-3-yl)-vinyl]benzonitrile;
5-methoxy-3-(1-(pyridin-3-yl)prop-1-en-2-yl)-1H-indole;
(Z)-(1H-indol-3-yl)-(pyridin-3-ylimino)-acetonitrile;
and their pharmaceutically acceptable salts.

According to another embodiment of the invention, the compounds of the present invention are used as a medicament.

Accordingly, the instant invention is also directed to a pharmaceutical composition containing as an active ingredient at least one compound of the invention.

The compounds of the present invention can be prepared by conventional methods of organic synthesis practiced by those skilled in the art. The general reaction sequences outlined below represent a general method useful for preparing the compounds of the present invention and are not meant to be limiting in scope or utility.

Some compounds of general formula (I) and in particular of the general formula (III) can be prepared via one step sequence starting from a compound of formula (i) according to scheme 1 below.

Scheme 1

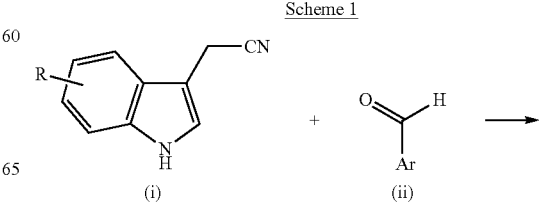

-continued

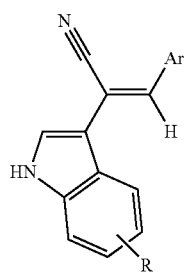

According to this process, a 3-indolyleacetonitrile derivative of formula (I) can be reacted with the compound of formula (II) (wherein Ar is independently a five or six-membered ring bearing eventually heteroatoms) for example in the presence of Na or NaH, for example in a solvent such as methanol or DMSO, for example at a temperature ranging between room temperature to reflux, to obtain a compound according to the invention.

The starting compounds of formula (I) and (ii) are commercially available or can be prepared according to methods known to the person skilled in the art, such as described hereafter.

The chemical structures and physical data of some compounds of formula (I) of the invention are illustrated in the following Table I.

TABLE I (I)

| N° | $R_1$ | $R_2$ | $R_3$ | Z | $R_4$ | | Y |
|---|---|---|---|---|---|---|---|
| 1 | H | H | H | CH | CN | | $C(R_5)_1$ |
| 2 | H | H | H | CH | CN | | $C(R_5)_1$ |
| 3 | H | H | H | CH | CN | | $C(R_5)_1$ |
| 4 | H | $OCH_3$ | H | CH | CN | | $C(R_5)_1$ |
| 5 | H | OCH₂C₆H₅ | H | CH | CN | | $C(R_5)_1$ |
| 6 | H | $OCH_3$ | H | CH | CN | | $C(R_5)_1$ |
| 7 | H | $OCH_3$ | H | CH | CN | | $C(R_5)_1$ |
| 8 | H | H | H | CH | CN | | $C(R_5)_1$ |

TABLE I-continued
(I)
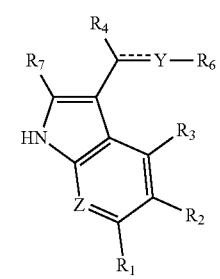
| | R₁ | R₂ | R₃ | Z | R₇ | R₄═Y—R₆ | Y |
|---|---|---|---|---|---|---|---|
| 9 | H | H | H | CH | CN | 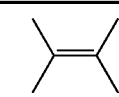 | C(R₅)₁ |
| 10 | H | H | H | CH | CN | 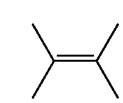 | C(R₅)₁ |
| 11 | H | H | H | CH | CN | 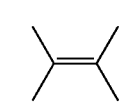 | C(R₅)₁ |
| 12 | H | H | H | CH | CN | 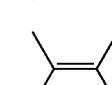 | C(R₅)₁ |
| 13 | H | H | H | CH | CN | 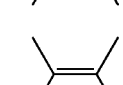 | C(R₅)₁ |
| 14 | H | OCH₃ | H | CH | CN | 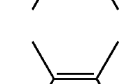 | C(R₅)₁ |
| 15 | H | H | H | CH | CN | 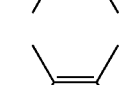 | C(R₅)₁ |
| 16 | H | OCH₃ | H | CH | CN | 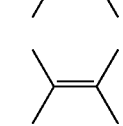 | C(R₅)₂ |
| 17 | H | H | H | CH | CN |  | C(R₅)₂ |
| 18 | H | OCH₃ | H | CH | CN |  | C(R₅)₁ |
| 19 | H | H | H | CH | H |  | C(R₅)₁ |
| 20 | H | 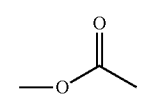 | H | CH | CN | 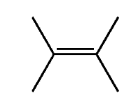 | C(R₅)₁ |
| 21 | H | 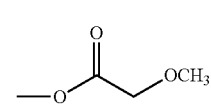 | H | CH | CN | 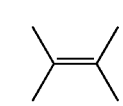 | C(R₅)₁ |

TABLE I-continued (I)

| | R7 | R2 | R3 | Z | R6 | | |
|---|---|---|---|---|---|---|---|
| 22 | H | —O—CH₂—CH₃ | H | CH | CN | | C(R₅)₁ |
| 23 | H | —O—CH(CH₃)₂ | H | CH | CN | | C(R₅)₁ |
| 24 | H | Cl | H | CH | CN | | C(R₅)₁ |
| 25 | H | F | H | CH | CN | | C(R₅)₁ |
| 26 | OCH₃ | H | H | CH | CN | | C(R₅)₁ |
| 27 | H | H | OCH₃ | CH | CN | | C(R₅)₁ |
| 28 | H | OCH₃ | H | CH | CN | | C(R₅)₁ |
| 29 | H | OH | H | CH | CN | | C(R₅)₁ |
| 30 | H | OCH₃ | H | CH | CN | | C(R₅)₁ |
| 31 | H | OCH₃ | H | CH | CN | | C(R₅)₁ |
| 32 | H | OCH₃ | H | CH | CN | | C(R₅)₁ |
| 33 | H | OCH₃ | H | CH | CN | | C(R₅)₁ |
| 34 | H | (2-propyl-4,5-dihydrooxazole) | | CH | CN | | C(R₅)₁ |

TABLE I-continued
(I)
| | | | | | | | |
|---|---|---|---|---|---|---|---|
| 35 | H | OCH$_3$ | H | CH | CN |  | C(R$_5$)$_1$ |
| 36 | H | H | H | N | CN |  | C(R$_5$)$_1$ |
| 37 | H | Br | H | CH | CN | 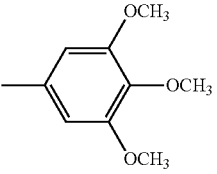 | C(R$_5$)$_1$ |
| 38 | H |  | H | CH | CN | 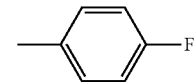 | C(R$_5$)$_1$ |
| 39 | H |  | H | CH | CN |  | C(R$_5$)$_1$ |
| 40 | H | NH$_2$ | H | CH | CN |  | C(R$_5$)$_1$ |
| 41 | H | NHC(O)OCH$_3$ | H | CH | CN |  | C(R$_5$)$_1$ |
| 42 | H | H | H | CH | CN |  | C(R$_5$)$_1$ |
| 43 | H | OCH$_3$ | H | CH | CN |  | C(R$_5$)$_1$ |
| 44 | H | H | H | CH | CN |  | C(R$_5$)$_1$ |
| 45 | H | OCH$_3$ | H | CH | CN |  | C(R$_5$)$_1$ |
| 46 | H | OCH$_3$ | H | CH | CN | | C(R$_5$)$_1$ |

TABLE I-continued (I)

|  | R7 | R2 | R3 | R4 | R6 | | C(R5)/Z |
|---|---|---|---|---|---|---|---|
| 47 | H | OCH$_3$ | H | CH | CN | | C(R$_5$)$_1$ |
| 48 | H | OCH$_3$ | H | CH | CN | | C(R$_5$)$_1$ |
| 49 | H | OCH$_3$ | H | CH | CN | | C(R$_5$)$_1$ |
| 50 | H | OCH$_3$ | H | CH | CN | | C(R$_5$)$_1$ |
| 51 | H | OCH$_3$ | H | CH | CN | | C(R$_5$)$_1$ |
| 52 | H | OCH$_3$ | H | CH | CN | | C(R$_5$)$_1$ |
| 53 | H | OCH$_3$ | H | CH | CN | | C(R$_5$)$_1$ |
| 54 | H | OCH$_3$ | H | CH | CN | | C(R$_5$)$_1$ |
| 55 | H | OH | H | CH | CN | | C(R$_5$)$_1$ |
| 56 | H | H | H | CH | C(O)NH$_2$ | | C(R$_5$)$_1$ |
| 57 | H | H | H | CH | H | | C(R$_5$)$_1$ |
| 58 | H | OCH$_3$ | H | CH | C≡CH | | C(R$_5$)$_1$ |
| 59 | H | OCH$_3$ | H | CH | CH$_3$ | | C(R$_5$)$_1$ |

TABLE I-continued
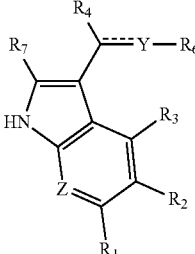
(I)
| N° | | | | | | | |
|----|---|---|---|---|---|---|---|
| 60 | H | OCH₃ | H | CH | CN | 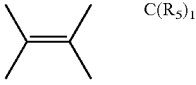 | C(R₅)₁ |
| 61 | H | H | H | CH | CN | 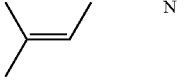 | N |
| N° | R₅ | R₇ | R₆ | M.p (° C.) |
|----|----|----|----|------------|
| 1 | H | H | 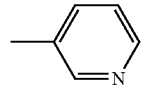 | 201 |
| 2 | 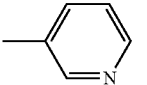 | H | H | 218 |
| 3 | H | H | 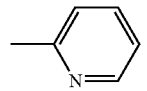 | 152 |
| 4 | H | H | 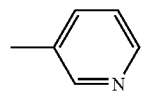 | 175 |
| 5 | H | H | 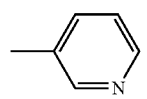 | 192 |
| 6 | H | H | 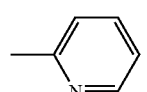 | 148 |
| 7 | H | H | 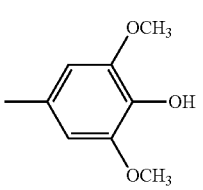 | 176 |
| 8 | H | H | 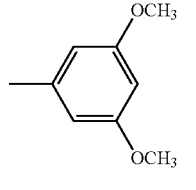 | 118 |
| 9 | H | H | 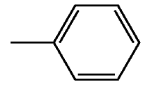 | 112 |

TABLE I-continued
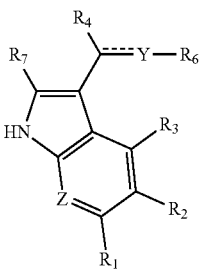
(I)
| | | | | |
|---|---|---|---|---|
| 10 | H | H | 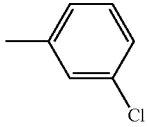 | 149 |
| 11 | H | H | 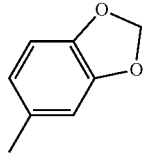 | 168 |
| 12 | H | H | 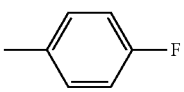 | 132 |
| 13 | H | H | 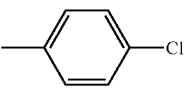 | 140 |
| 14 | H | H | 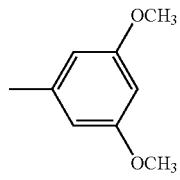 | 141 |
| 15 | H | H | 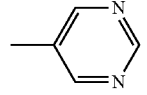 | 231 |
| 16 | H | H | 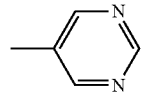 | 214 |
| 17 | H | H | 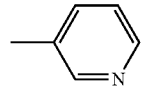 | 138 |
| 18 | H | H | 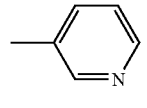 | 129 |
| 19 | CN | H | 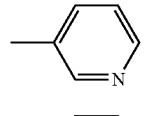 | 189 |
| 20 | H | H | 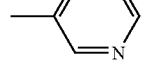 | 228 |

TABLE I-continued (I)

[Structure: indole-like bicycle with R7 at 2-position, HN, Z in ring, R1, R2, R3 substituents, and C(R4)=Y-R6 at 3-position]

| | | | | |
|---|---|---|---|---|
| 21 | H | H | [3-pyridyl] | 184 |
| 22 | H | H | [3-pyridyl] | 196 |
| 23 | H | H | [3-pyridyl] | 211 |
| 24 | H | H | [3-pyridyl] | — |
| 25 | H | H | [3-pyridyl] | — |
| 26 | H | H | [3-pyridyl] | — |
| 27 | H | H | [3-pyridyl] | 177 |
| 28 | H | H | [6-fluoro-3-pyridyl] | — |
| 29 | H | H | [3-pyridyl] | 258 |
| 30 | H | H | [3-cyanophenyl] | 149 |
| 31 | H | H | [4-methyl-3-pyridyl] | 213 |

TABLE I-continued
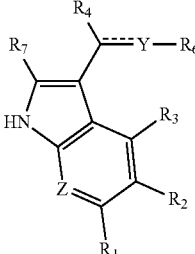
(I)
| | | | | |
|---|---|---|---|---|
| 32 | H | H | 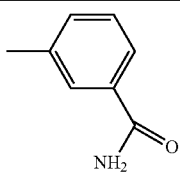 | 234 |
| 33 | H | H | 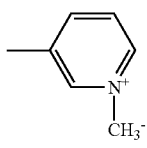 | — |
| 34 | C(R$_5$)$_1$ | H | 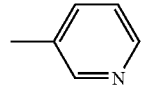 | — |
| 35 | H | CH$_3$ | 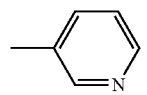 | — |
| 36 | H | H | 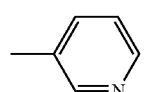 | — |
| 37 | H | H | 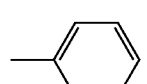 | — |
| 38 | H | H | 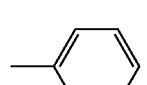 | — |
| 39 | H | H | 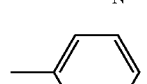 | — |
| 40 | H | H | 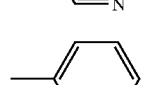 | — |
| 41 | H | H | 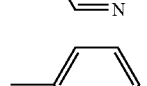 | — |
| 42 | H | H | 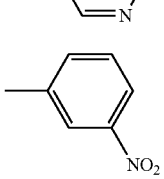 | 203 |

TABLE I-continued

| | | | | (I) |
|---|---|---|---|---|

| 43 | H | H | 3-methyl-5-nitrophenyl | 188 |
| 44 | H | H | 3-methyl-5-aminophenyl | 138 |
| 45 | H | H | 3-aminophenyl | 124 |
| 46 | H | H | 5-methoxypyridin-3-yl | 162 |
| 47 | H | H | 4-chloro-3-methylpyridinyl | — |
| 48 | H | H | 2-fluoro-3-methylpyridinyl | — |
| 49 | H | H | 6-chloropyridin-3-yl | 184 |
| 50 | H | H | 3-methylthiophen-yl | — |
| 51 | H | H | 1-methyl-1H-pyrazol-4-yl | 178 |
| 52 | H | H | 6-methoxypyridin-3-yl | — |

TABLE I-continued

| # | R7 | R3 | R6 | value |
|---|----|----|----|-------|
| 53 | H | H | 5-methyl-2-methylpyridine | — |
| 54 | H | H | 5-methyl-pyridine-2-carbonitrile | 221 |
| 55 | H | H | 3-methylbenzonitrile | — |
| 56 | H | H | 3-methylpyridine | 96 |
| 57 | H | H | 3-methylpyridine | 190 |
| 58 | H | H | 3-methylpyridine | 136 |
| 59 | H | H | 3-methylpyridine | — |
| 60 | CH₃ | H | 3-methylpyridine | — |
| 61 | / | H | 3-methylpyridine | — |

The following examples illustrate in detail the preparation of compounds of formula (I) and sub-groups of compounds of formula (II), (III) (IV) and (V) according to the invention. The structures of the products obtained have been confirmed by NMR spectra.

Starting compounds and reactants, unless otherwise indicated, are commercially available or described in literature, or can be prepared according to methods described in literature or known to one skilled in the art.

EXAMPLE 1

(Z)-2-(1H-indol-3-yl)-3-pyridin-3-yl-acrylonitrile

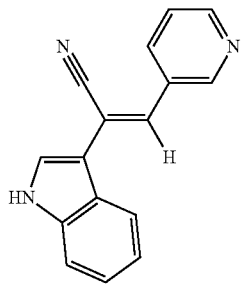 [SMILES: N#C/C(=C\c1cccnc1)c1c[nH]c2ccccc12]

To a solution of sodium methanolate [prepared from sodium (530 mg, 9.8 mmol, 1.5 eq.) in anhydrous methanol (10 mL)] were added, under an argon atmosphere, (1H-indol-3-yl)-acetonitrile (1 g, 6.4 mmol, 1.0 eq.) and pyridine-3-carbaldehyde (1000 μl, 10.7 mmol, 1.7 eq.). The reaction apparatus was protected from light and the mixture heated at reflux for 3 hours. The reaction was allowed to cool to room temperature and again cooled to −78° C. in a dry ice/ethanol bath. The resulting precipitate was filtered and washed with methanol and diethyl ether to afford the compound (1) as a yellow powder (1.07 g, 68%). TLC: Rf=0.12 (heptane 60/EtOAc 40); Mp 201° C.; IR $\square_{max}$ (cm$^{-1}$): 2219 ($v_{CN}$); $^1$H NMR (DMSO, 500 MHz): δ (ppm): 7.19 (1H, t, $J_{5'-6'}$=$J_{5'-4'}$=7.9 Hz, H5'), 7.25 (1H, t, $J_{6'-5'}$=$J_{6'-7'}$=7.9 Hz, H6'), 7.52 (1H, d, $J_{7'-6'}$=7.9 Hz, H7'), 7.54 (1H, dd, $J_{5''-4''}$=8.2 Hz, $J_{5''-6''}$=4.9 Hz, H5''), 7.82 (1H, s, H3), 7.85 (1H, s, H2'), 8.10 (1H, d, $J_{4'-5'}$=7.9 Hz, H4'), 8.32 (1H, d, $J_{4''-5''}$=8.2 Hz, H4''), 8.59 (1H, dd, $J_{6''-5''}$=4.9 Hz, $J_{6''-4''}$=1.5 Hz, H6''), 9.00 (1H, d, $J_{2''-4''}$=2.4 Hz, H2''); $^{13}$C NMR (DMSO, 75.5 MHz): δ (ppm): 108.2 (C2), 110.6 (C3'), 112.7 (C7'), 118.2 (C1), 119.7 (C4'), 120.8 (C5'), 122.8 (C6'), 123.7 (C3a'), 123.8 (C5''), 127.4 (C2'), 130.9 (C3''), 132.6 (C3), 134.7 (C4''), 137.4 (C7a'), 149.7 (C6''), 150.0 (C2''); ESI-MS m/z: 246.1 [M+H]$^+$, 268.1 [M+Na]$^+$, 300.1 [M+Na+MeOH]$^+$; HRES-MS m/z 246.0999 (calcd for $C_{16}H_{12}N_3$, 246.1031).

EXAMPLE 2

(E)-2-(1H-indol-3-yl)-3-pyridin-3-yl-acrylonitrile

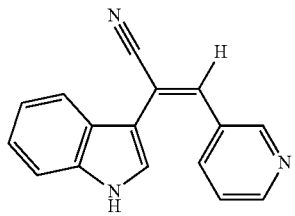 [SMILES: N#C/C(=C/c1cccnc1)c1c[nH]c2ccccc12]

A solution of compound according to example 1 (200 mg, 0.8 mmol) in ethanol (50 mL) was irradiated under argon bubbling for 4 hours in a closed air glass apparatus with a halogen lamp (150 W). The solvent was removed under reduced pressure, and the crude purified by silica gel flash-column chromatography (eluent: CH$_2$Cl$_2$/MeOH, 99:1 to 97:3). The residue was triturated with dichloromethane to afford the compound (2) as a pale yellow powder (70 mg, 35%). TLC: Rf=0.46 (EtOAc100); Mp 218° C. IR $v_{max}$ (cm$^{-1}$): 2214 ($v_{CN}$); $^1$H NMR (DMSO, 300 MHz): δ (ppm): 6.93 (1H, m, H5'), 6.96 (1H, t, H6'), 7.14 (1H, m, H7'), 7.23 (1H, dd, $J_{5''-4''}$=8.0 Hz, $J_{5''-6''}$=4.8 Hz, H5''), 7.47 (1H, d, $J_{7'-6'}$=8.2 Hz, H7'), 7.55 (1H, s, H3), 7.59 (1H, d, $J_{4''-5''}$=8.0 Hz, H4''), 7.66 (1H, s, H2'), 8.41 (1H, dd, $J_{6''-5''}$=4.8 Hz, $J_{6''-4''}$=1.6 Hz, H6''), 8.49 (d, $J_{2''-4''}$=2.3 Hz, H2''), 11.71 (1H, s, indolic H); $^{13}$C NMR (DMSO, 75.5 MHz): δ (ppm): 106.8 (C3'), 108.5 (C1), 112.4 (C7'), 119.3 (C5'), 120.0 (C6'), 120.2 (C2), 122.1 (C4'), 123.3 (C5''), 123.6 (C3a'), 127.1 (C2'), 130.7 (C3''), 135.8 (C4''), 136.4 (C7a'), 138.1 (C3), 149.7 (C6''), 150.1 (C2''). ES-MS m/z 246.1 [M+H]$^+$; HRES-MS m/z 246.1038 (calcd for $C_{16}H_{12}N_3$, 246.1031).

EXAMPLE 3

(Z)-2-(1H-indol-3-yl)-3-pyridin-2-yl-acrylonitrile

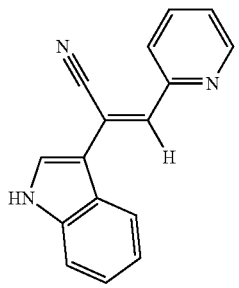 [SMILES: N#C/C(=C\c1ccccn1)c1c[nH]c2ccccc12]

The same procedure was performed as for example 1 except that the used carbaldehyde was the pyridine-2-carbaldehyde (1 mL, 10.5 mmol, 1.6 eq.). The mixture was heated at reflux for 2 h15. The reaction was allowed to cool to room temperature and the solvent was removed under reduced pressure. The residue was purified by silica gel flash-column chromatography (eluent: CH$_2$Cl$_2$/MeOH, 100:0 to 96:4). Then the product was recristallized from dichloromethane (dry ice/ethanol bath) to afford the compound (3) as yellow crystals (350 mg, 22%). TLC: Rf=0.32 (CH$_2$Cl$_2$ 98/MeOH 2). Mp 152° C.; IR $v_{max}$ (cm$^{-1}$): 2216 ($v_{CN}$), 3373 ($v_{N-H}$); $^1$H NMR (DMSO, 300 MHz): δ (ppm): 7.20 (1H, td, $J_{5'-6'}$=$J_{5'-4'}$=7.2 Hz, $J_{5'-7'}$=1.3 Hz, H5'), 7.25 (1H, td, $J_{6'-5'}$=$J_{6'-7'}$=7.2 Hz, $J_{6'-4'}$=1.3 Hz, H6'), 7.37 (1H, ddd, $J_{5''-4''}$=7.5 Hz, $J_{5''-6''}$=4.8 Hz, $J_{5''-3''}$=1.1 Hz, H5''), 7.52 (1H, dd, $J_{7'-6'}$=7.2 Hz, $J_{7'-5'}$=1.3 Hz, H7'), 7.75 (1H, s, H3), 7.78 (1H, d, $J_{3''-4''}$=7.9 Hz, H3''), 7.86 (1H, s, H2'), 7.89 (1H, td, $J_{4''-5''}$=$J_{4''-3''}$=7.5 Hz, $J_{4''-6''}$=1.9 Hz, H4''), 8.10 (1H, dd, $J_{4'-5'}$=7.2 Hz, $J_{4'-6'}$=1.3 Hz, H4'), 8.69 (1H, d, $J_{6''-5''}$=4.8 Hz, H6''), 11.20 (1H, s, indolic H). $^{13}$C NMR (DMSO, 75.5 MHz): δ (ppm): 108.6 (C2), 111.2 (C3'), 112.5 (C7'), 117.9 (C1), 119.7 (C4'), 120.7 (C5'), 122.6 (C6'), 123.5 (C5''), 123.6 (C3a'), 124.7 (C3''), 127.9 (C2'), 133.7 (C3), 136.9 (C4''), 137.4 (C7a'), 149.3 (C6''), 152.7 (C2''); ES m/z 246.1 [M+H]$^+$, 268.1 [M+Na]$^+$, 300.1 [M+Na+MeOH]$^+$; HRES-MS m/z 268.0844 (calc for $C_{16}H_{11}N_3Na$, 268.0851).

EXAMPLE 4

(Z)-2-(5-methoxy-1H-indol-3-yl)-3-pyridin-3-yl-acrylonitrile

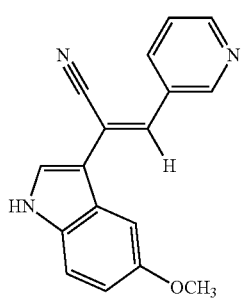 [SMILES: COc1ccc2[nH]cc(/C(C#N)=C/c3cccnc3)c2c1]

To a solution of sodium ethanolate [prepared from sodium (350 mg, 15.2 mmol, 2.8 eq.) in anhydrous ethanol (30 mL)] were added, under an argon atmosphere, (5-methoxy-1H-indol-3-yl)-acetonitrile (1.0 g, 5.4 mmol, 1.0 eq.) and pyridine-3-carbaldehyde (1 mL, 10.7 mmol, 2.0 eq.). The reaction mixture was heated at reflux for 1 hour. The reaction was allowed to cool to room temperature and then, the solvent was removed under reduced pressure and the residue purified by silica gel flash-column chromatography (eluent: $CH_2Cl_2$/MeOH, 98:2 to 97:3). The product impure was triturated with ethanol and diethyl ether to afford the compound (4) as yellow crystals (1.08 g, 73%). TLC: Rf=0.29 ($CH_2Cl_2$ 97/MeOH 3); Mp 175° C.; 2216 ($v_{CN}$); $^1$H NMR (DMSO, 300 MHz): δ (ppm): 3.83 (3H, s, 5'-methoxy), 6.90 (1H, dd, $J_{6'-7'}$=8.9 Hz, $J_{6'-4'}$=2.4 Hz, H6'), 7.40 (1H, d, $J_{7'-6'}$=8.9 Hz, H7'), 7.48 (1H, d, $J_{4'-6'}$=2.4 Hz, H4'), 7.52 (1H, dd, $J_{5''-4''}$=8.1 Hz, $J_{5''-6''}$=4.8 Hz, H5''), 7.74 (1H, s, H3), 7.78 (1H, s, H2'), 8.32 (1H, d, $J_{4''-5''}$=8.1 Hz, H4''), 8.58 (1H, dd, $J_{6''-5''}$=4.8 Hz, $J_{6''-4''}$=1.6 Hz, H6''), 8.98 (1H, d, $J_{2''-4''}$=2.3 Hz, H2''), 11.65 (1H, s, indolic H); $^{13}$C NMR (DMSO, 75.5 MHz): δ (ppm): 55.6 (5'-methoxy), 101.9 (C4'), 108.2 (C2), 110.2 (C3'), 112.4 (C6'), 113.2 (C7'), 118.1 (C1), 123.6 (C5''), 124.0 (C3a'), 127.6 (C2'), 130.9 (C3''), 132.2 (C3), 132.2 (C7a'), 134.6 (C4''), 149.5 (C6''), 149.9 (C2''), 154.6 (C5'); ES-MS m/z 276.1 [M+H]$^+$, 298.1 [M+Na]$^+$, 330.1 [M+Na+MeOH]$^+$; HRES-MS m/z 276.110 (calcd for $C_{17}H_{14}N_3O$, 276.1137; Anal. Calcd for $C_{17}H_{14}N_3O$: C, 74.17%; H, 4.76%; N, 15.26%; O, 5.81%. Found C, 73.89%; H, 4.82%; N, 15.33%; O, 6.03%.

EXAMPLE 5

(Z)-2-(5-benzyloxy-1H-indol-3-yl)-3-pyridin-3-yl-acrylonitrile

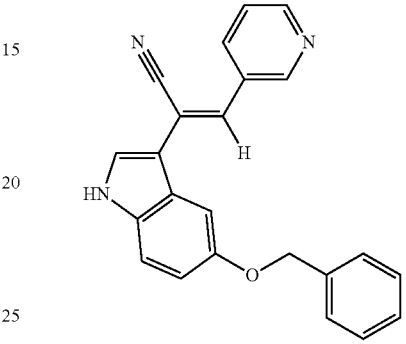

To a suspension of NaH (30 mg, 80%, 1.3 mmol, 1.6 eq.) in anhydrous DMSO (2.8 mL) was added, under an argon atmosphere, a solution of (5-benzyloxy-1H-indol-3-yl)-acetonitrile (200 mg, 0.8 mmol, 1 eq.) and pyridin-3-carbaldehyde (100 μl, 1.1 mmol, 1.4 eq.) in a mixture of anhydrous DMSO 4 mL) and diethyl ether (4 mL). The reaction apparatus was protected from light and the mixture was stirred at ambient temperature for 1 h30, and then treated with brine. The mixture was extracted with ethyl acetate and the organic layer was washed with water and saturated aqueous ammonium chloride solution, and then dried over $MgSO_4$. The solvent was removed under reduced pressure, and the residue triturated with dichloromethane and diethyl ether to afford the compound (5) as a yellow powder (80 mg, 30%). TLC: Rf=0.22 (heptane 40/EtOAc 60); Mp 192° C.; IR $v_{max}$ (cm$^{-1}$): 2218 ($v_{CN}$); $^1$H NMR (DMSO, 300 MHz): δ (ppm): 5.19 (2H, s, 2H8'), 6.98 (1H, dd, $J_{6'-7'}$=8.9 Hz, $J_{6'-4'}$=2.3 Hz, H6'), 7.34 (1H, m, H12'), 7.39 (2H, m, H11' and H13'), 7.41 (1H, d, $J_{7'-6'}$=8.9 Hz, H7'), 7.50 (2H, d, $J_{10'-11'}$=$J_{14'-13'}$=7.2 Hz, H10' and H14'), 7.53 (1H, dd, $J_{5''-4''}$=8.1 Hz, $J_{5''-6''}$=4.8 Hz, H5''), 7.58 (1H, d, $J_{4'-6'}$=2.3 Hz, H4'), 7.70 (1H, s, H3), 7.78 (1H, s, H2'), 8.31 (1H, d, $J_{4''-5''}$=8.1 Hz, H4''), 8.59 (1H, dd, $J_{6''-5''}$=4.8 Hz, $J_{6''-4''}$=1.5 Hz, H6''), 8.97 (1H, d, $J_{2''-4''}$=2.1 Hz, H2''), 11.67 (1H, s, indolic H); $^{13}$C NMR (DMSO, 75.5 MHz): δ (ppm): 70.0 (C8'), 103.4 (C4'), 108.2 (C2), 110.2 (C3'), 113.1 (C6'), 113.2 (C7'), 118.0 (C1), 123.7 (C5''), 123.9 (C3a'), 127.7 (C10', C14' and C12'), 127.8 (C2'), 128.4 (C11' and C13'), 130.9 (C3''), 132.0 (C3), 132.4 (C7a'), 134.5 (C4''), 137.6 (C9'), 149.5 (C6''), 149.9 (C2''), 153.6 (C5'); ES-MS m/z 352.1 [M+H]$^+$, 374.1 [M+Na]$^+$; HRES-MS m/z 352.1467 (calcd for $C_{23}H_{18}N_3O$, 352.1450).

EXAMPLE 6

(Z)-2-(5-methoxy-1H-indol-3-yl)-3-pyridin-2-yl-acrylonitrile

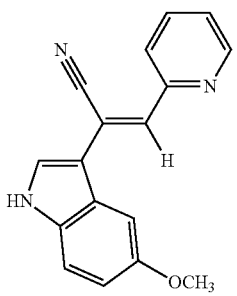 [SMILES: COc1ccc2[nH]cc(/C(C#N)=C/c3ccccn3)c2c1]

To a suspension of NaH (49.2 mg, 80%, 1.6 mmol, 1.5 eq.) in anhydrous DMSO (1.8 mL) was added, under an argon atmosphere, a solution of (5-methoxy-1H-indol-3-yl)-acetonitrile (200 mg, 1.1 mmol, 1.0 eq.) and pyridine-2-carbaldehyde (110 µl, 1.16 mmol, 1.1 eq.) in a mixture of anhydrous DMSO (4 ml) and diethyl ether (4 ml). The reaction apparatus was protected from light and the mixture was stirred at ambient temperature for 1 h15, cooled to 0° C., and treated with methanol. The reaction was stirred again for 20 minutes. The mixture was extracted with ethyl acetate, and the organic layer was washed with water and brine, and then dried over $MgSO_4$. The solvent was removed under reduced pressure, and the residue purified by silica gel flash-column chromatography (eluent: $CH_2Cl_2$/MeOH, 100:0 to 98.5:1.5). The product was further purified by aluminium oxide pad filtration (eluent: heptane/$CH_2Cl_2$). The residue was triturated with diethyl ether and heptane to afford the compound (6) as a yellow powder (83 mg, Rdt: 28%). TLC: Rf=0.32 ($CH_2Cl_2$ 98/MeOH 2); Mp 148° C.; IR $\nu_{max}$ (cm$^{-1}$): 2217 ($\nu_{CN}$); $^1$H NMR (DMSO, 500 MHz): δ (ppm): 3.84 (3H, s, 5'-methoxy), 6.90 (1H, dd, $J_{6'-7'}$=8.9 Hz, $J_{6'-4'}$=2.2 Hz, H6'), 7.38 (1H, dd, $J_{5'''-4'''}$=7.6 Hz, $J_{5'''-6'''}$=4.9 Hz, H5'''), 7.41 (1H, d, $J_{7'-6'}$=8.9 Hz, H7'), 7.50 (1H, d, $J_{4'-6'}$=2.2 Hz, H4'), 7.68 (1H, s, H3), 7.78 (1H, d, $J_{3'''-6'''}$=7.9 Hz, H3'''), 7.82 (1H, s, H2'), 7.90 (1H, td, $J_{4'''-5'''}$=$J_{4'''-3'''}$=7.6 Hz, $J_{4'''-6'''}$=1.8 Hz, H4'''), 8.69 (1H, d, $J_{6'''-5'''}$=4.9 Hz, H6'''), 11.67 (1H, s, indolic H); $^{13}$C NMR (DMSO, 75.5 MHz): δ (ppm): 56.0 (5'-methoxy), 102.6 (C4'), 109.2 (C2), 111.3 (C3'), 112.8 (C6'), 113.8 (C7'), 118.5 (C1), 124.0 (C5'''), 124.6 (C3a'), 125.3 (C3'''), 128.8 (C2'), 132.87 (C7a'), 134.0 (C3), 137.4 (C4'''), 149.8 (C6'''), 153.2 (C2'''), 155.1 (C5'); ES-MS m/z 276.1 [M+H]$^+$, 298.1 [M+Na]$^+$; HRES-MS m/z 276.1128 (calcd for $C_{17}H_{14}N_3O$, 276.1137).

EXAMPLE 7

(Z)-3-(4-hydroxy-3,5-dimethoxy-phenyl)-2-(5-methoxy-1H-indol-3-yl)-acrylonitrile

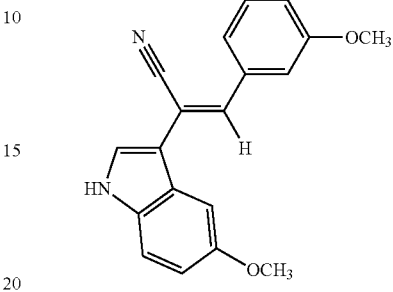

1) Preparation of 3,5-dimethoxy-4-(2-methoxy-ethoxymethoxy)-benzaldehyde

To a mixture of 4-hydroxy-3,5-dimethoxy-benzadehyde (1 g, 5.5 mmol, 1.0 eq.) in dichloroethane (13 mL) were added DIPEA (1.43 mL, 8.2 mmol, 1.5 eq.) and MEMCl (816 µl, 7.1 mmol, 1.3 eq.). The mixture was heated at reflux for 2 hours. The reaction was allowed to cool to room temperature and the organic layer was washed with a saturated aqueous ammonium chloride solution, 0.1 M aqueous sodium hydroxide solution and brine, and then dried over $MgSO_4$. The solvent was removed under reduced pressure and the residue purified by silica gel pad filtration (eluent: EtOAc/MeOH) to afford the 3,5-dimethoxy-4-(2-methoxy-ethoxymethoxy)-benzaldehyde as a beige oil (1.44 g, 97%).

2) Preparation of (Z)-3-[3,5-dimethoxy-4-(2-methoxy-ethoxymethoxy)-phenyl]-2-(5-methoxy-1H-indol-3-yl)-acrylonitrile To a suspension of NaH (60 mg, 80%, 2.5 mmol, 1.7 eq.) in DMSO (5 mL) was added, under an argon atmosphere, a solution of (5-methoxy-1H-indol-3-yl)-acetonitrile (331 mg, 1.8 mmol, 1.2 eq.) and 3,5-dimethoxy-4-(2-methoxy-ethoxymethoxy)-benzaldehyde (400 mg, 1.5 mmol, 1.0 eq.) in a mixture of DMSO (7 mL) and tert-butyl methyl ether (7 mL). The reaction apparatus was protected from light and the mixture was stirred at ambient temperature for 3 hours, and then treated with brine (10 mL). The mixture was extracted with ethyl acetate (3×30 mL), and the organic layer was washed with water and saturated aqueous ammonium chloride solution, and then dried over $MgSO_4$. The solvent was removed under reduced pressure and the residue purified by silica gel flash-column chromatography (eluent: heptane/AcOEt, 70:30 to 50:50) to afford (Z)-3-[3,5-dimethoxy-4-(2-methoxy-ethoxymethoxy)-phenyl]-2-(5-methoxy-1H-indol-3-yl)-acrylonitrile as a yellow oil (100 mg) used in the next synthetic step without further purification.

3) Preparation of (Z)-3-(4-hydroxy-3,5-dimethoxy-phenyl)-2-(5-methoxy-1H-indol-3-yl)-acrylonitrile To a solution of (Z)-3-[3,5-dimethoxy-4-(2-methoxy-ethoxymethoxy)-phenyl]-2-(5-methoxy-1H-indol-3-yl)-acrylonitrile (100 mg) in THF (5 mL) was added a 2M aqueous hydrochloric acid solution (4 mL). The reaction apparatus was protected from light and the mixture stirred at ambient temperature for 5 days. The mixture was poured into water, extracted with dichloromethane (3×20 mL) and the organic layer was dried over MgSO$_4$. The solvent was removed under reduced pressure and the crude purified by silica gel flash-column chromatography (eluent: CH$_2$Cl$_2$/MeOH, 99:1). The residue was triturated with diethyl ether to afford the compound (7) as a yellow powder (50 mg, 10% for two steps). TLC: Rf=0.53 (CH$_2$Cl$_2$ 96/MeOH 4); Mp 176° C.; IR $\nu_{max}$ (cm$^{-1}$): 2212 ($\nu_{CN}$), 3343 ($\nu_{N-H}$), 3526 ($\nu_{O-H}$); $^1$H NMR (DMSO, 500 MHz): δ (ppm): 3.82 (3H, s, 5'-methoxy), 3.83 (6H, s, 3"-methoxy and 5"-methoxy), 6.89 (1H, dd, J$_{6'-7'}$=8.9 Hz, J$_{6'-4'}$=2.4 Hz, H6'), 7.31 (2H, s, H2" and H6"), 7.39 (1H, d, J$_{7'-6'}$=8.9 Hz, H7'), 7.44 (1H, d, J$_{4'-6'}$=2.4 Hz, H4'), 7.58 (1H, s, H3), 7.68 (1H, s, H2'), 9.01 (1H, s, phenolic H), 11.51 (1H, s, indolic H); $^{13}$C NMR (DMSO, 75.5 MHz): δ (ppm): 55.6 (5'-methoxy), 56.0 (3"-methoxy and 5"-methoxy), 101.8 (C4'), 102.1 (C2), 106.6 (C2" and C6"), 110.6 (C3'), 111.9 (C6'), 113.0 (C7'), 119.3 (C1), 124.2 (C3a'), 124.9 (C1"), 126.1 (C2'), 132.2 (C7a'), 137.6 (C3), 147.9 (C3" and C5"), 154.2 (C5'); ES-MS m/z 349.1 [M−H]$^-$; HRES-MS m/z 349.1188 (calcd for C$_{20}$H$_{17}$N$_2$O$_4$, 349.1188).

EXAMPLE 8

(Z)-3-(3,5-dimethoxy-phenyl)-2-(1H-indol-3-yl)-acrylonitrile

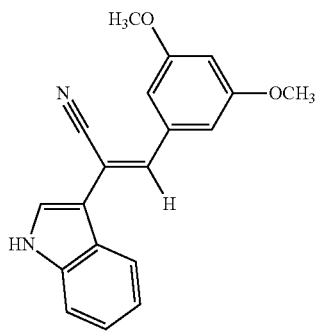 [SMILES: COc1cc(/C=C(\C#N)c2c[nH]c3ccccc23)cc(OC)c1]

To a solution of sodium ethanolate [prepared from sodium (100 mg, 4.3 mmol, 1.7 eq.) in anhydrous ethanol (6 mL)] were added, under an argon atmosphere, (1H-indol-3-yl)-acetonitrile (400 mg, 2.6 mmol, 1.0 eq.) and, after 30 minutes stirring, 3,5-dimethoxy-benzaldehyde (420 mg, 2.5 mmol, 1.0 eq.). The reaction apparatus was protected from light and the mixture stirred at room temperature for 38 hours. The solvent was removed under reduced pressure, and the residue purified by silica gel flash-column chromatography (eluent: heptane/EtOAc, 95:5 to 70:30). The product was further purified by silica gel flash-column chromatography (eluent: CH$_2$Cl$_2$/MeOH, 100:0 to 99:1), and the residue was triturated with ethanol and diethyl ether to afford the compound (8) as a yellow powder (150 mg, 19%). TLC: Rf=0.27 (heptane 70/EtOAc 30); Mp 118° C.; IR $\nu_{max}$ (cm$^{-1}$): 2219 ($\nu_{CN}$), 3357 ($\nu_{N-H}$); $^1$H NMR (DMSO, 300 MHz): δ (ppm): 3.81 (6H, s, 3"-methoxy and 5"-methoxy), 6.59 (1H, s, H4"), 7.14 (2H, s, H2" and H6"), 7.19 (1H, t, J$_{5'-4'}$=J$_{5'-6'}$=7.9 Hz, H5'), 7.24 (1H, t, J$_{6'-5'}$=J$_{6'-7'}$=7.9 Hz, H6'), 7.50 (1H, d, J$_{7'-6'}$=7.9 Hz, H7'), 7.71 (1H, s, H2'), 7.79 (1H, s, H3), 8.06 (1H, d, J$_{4'-5'}$=7.9 Hz, H4'), 11.73 (1H, s, indolic H); $^{13}$C NMR (DMSO, 75.5 MHz): δ (ppm): 55.8 (3"-methoxy and 5"-methoxy), 102.0 (C4"), 106.6 (C2), 107.0 (C2" and C6"), 111.1 (C3'), 113.0 (C7'), 118.9 (C1), 119.3 (C1), 120.0 (C4'), 121.0 (C5'), 123.0 (C6'), 124.1 (C3a'), 127.3 (C2'), 136.7 (C3), 132.3 (C3), 136.8 (C1"), 137.7 (C7a'), 161.0 (C3" and C5"); ES-MS m/z 327.1 [M+Na]$^+$; HRES-MS m/z 327.1080 (calcd for C$_{19}$H$_{16}$N$_2$O$_2$Na, 327.1109); Anal. Calcd for C$_{19}$H$_{16}$N$_2$O$_2$: C, 74.98%; H, 5.30%; N, 9.20%; O, 10.71%. Found C, 74.76%; H, 5.24%; N, 9.04%.

EXAMPLE 9

(Z)-2-(1H-indol-3-yl)-3-phenyl-acrylonitrile

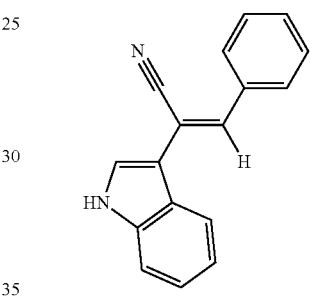

To a solution of sodium ethanolate [prepared from sodium (50 mg, 2.3 mmol, 1.7 eq.) in anhydrous ethanol (4 mL)] were added, under an argon atmosphere, (1H-indol-3-yl)-acetonitrile (200 mg, 1.3 mmol, 1.0 eq.) and, after 30 minutes stirring, benzaldehyde (157 µl, 1.5 mmol, 1.2 eq.). The reaction apparatus was protected from light and the mixture stirred at room temperature for 48 hours. The solvent was removed under reduced pressure, and the residue purified by silica gel flash-column chromatography (eluent: heptane/EtOAc, 90:10 to 80:20) to afford the compound (9) as a yellow powder (200 mg, 64%). $^1$H NMR (DMSO, 300 MHz): δ (ppm): 7.18 (1H, td, J$_{5'-4'}$=J$_{5'-6'}$=7.4 Hz, J$_{5'-7'}$=1.1 Hz, H5'), 7.24 (1H, t, J$_{6'-5'}$=J$_{6'-7'}$=7.4 Hz, J$_{6'4'}$=1.1 Hz, H6'), 7.42 (1H, m, H4"), 7.50 (3H, m, H7', H3" and H5"), 7.77 (1H, s, H3), 7.80 (1H, d, J=2.6 Hz, H2'), 7.91 (2H, d, J$_{2"-3"}$=J$_{6"-5"}$=7.3 Hz, H2" and H6"), 8.05 (1H, d, J$_{4'-5'}$=7.4 Hz, H4'), 11.72 (1H, s, indolic H); $^{13}$C NMR (DMSO, 75.5 MHz): δ (ppm): 105.8 (C2), 110.7 (C3'), 112.4 (C7'), 118.4 (C1), 119.4 (C4'), 120.5 (C5'), 122.5 (C6'), 123.7 (C3a'), 126.6 (C2'), 128.5 (C2" and C6"), 128.8 (C3" and C5"), 129.3 (C4"), 134.6 (C1"), 136.6 (C3), 137.2 (C7a'); TLC: Rf=0.58 (heptane 50/EtOAc 50); MS: ESI: m/z: 267.1 ([M+Na]$^+$), 511.2 ([2M+Na]$^+$) HRMS (ESI): calcd for C$_{17}$H$_{12}$N$_2$Na: m/z=267.0898. found: 267.0905; Microanalysis: Calcd for C$_{17}$H$_{12}$N$_2$%: C, 83.58; H, 4.95; N, 11.47 Found %: C, 83.32; H, 4.91; N, 11.36; IR $\nu_{max}$ (cm$^{-1}$): 2220 ($\nu_{CN}$); 3320 ($\nu_{N-H}$); Mp 112° C.

EXAMPLE 10

(Z)-3-(3-chloro-phenyl)-2-(1H-indol-3-yl)-acrylonitrile

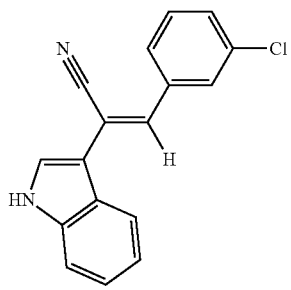 [SMILES: N#C/C(=C\c1cccc(Cl)c1)c1c[nH]c2ccccc12]

To a solution of sodium ethanolate [prepared from sodium (50 mg, 2.3 mmol, 1.7 eq.) in anhydrous ethanol (4 mL)] were added, under an argon atmosphere, (1H-indol-3-yl)-acetonitrile (200 mg, 1.3 mmol, 1.0 eq.) and, after 30 minutes stirring, 3-chloro-benzaldehyde (174 µl, 1.5 mmol, 1.2 eq.). The reaction apparatus was protected from light and the mixture stirred at room temperature for 48 hours. The solvent was removed under reduced pressure, and the crude purified by silica gel flash-column chromatography (eluent: heptane/EtOAc, 95:5 to 80:20). The residue was triturated with diisopropyl ether and heptane to afford the compound (10) as a yellow powder (110 mg, 31%); $^1$H NMR (DMSO, 300 MHz): δ (ppm): 7.18 (1H, t, $J_{5'-4'}=J_{5'-6'}=7.6$ Hz, H5'), 7.24 (1H, t, $J_{6'-5'}=J_{6'-7'}=7.6$ Hz, H6'), 7.50 (1H, m, H4" and 1-15"), 7.52 (1H, d, $J_{7'-6'}=7.6$ Hz, H7'), 7.76 (1H, s, H3), 7.76 (1H, s, H3), 7.82 (1H, m, H2'), 7.89 (1H, d, $J_{6''-5''}=7.5$ Hz, H6"), 7.96 (1H, s, H2"), 8.08 (1H, d, $J_{4'-5'}=7.6$ Hz, H4'), 11.77 (1H, s, indolic H); $^{13}$C NMR (DMSO, 75.5 MHz): δ (ppm): 107.3 (C2), 110.5 (C3'), 112.5 (C7'), 118.0 (C1), 119.6 (C4'), 120.6 (C5'), 122.6 (C6'), 123.5 (C3a'), 126.7 (C6"), 127.2 (C2'), 128.2 (C2"), 128.8 (C4"), 130.6 (C5"), 133.4 (C3"), 134.2 (C3), 136.8 (C1"), 137.2 (C7a'); TLC: Rf=0.66 (heptane 50/EtOAc 50); MS: ESI: m/z: 101.1 ([M+Na]$^+$)HRMS (ESI): calcd for $C_{17}H_{11}ClN_2Na$ m/z=301.0508. found: 301.0516; Microanalysis: Calcd for $C_{17}H_{11}ClN_2$%: C, 73.25; H, 3.98; Cl 12.72; N, 10.05. Found %: C, 72.94; H, 4.04; N, 9.89; IR $v_{max}$ (cm$^{-1}$): 2221 ($v_{CN}$), 3331 ($v_{N-H}$); Mp 149° C.

EXAMPLE 11

(Z)-3-benzo[1,3]dioxol-5-yl-2-(1H-indol-3-yl)-acrylonitrile

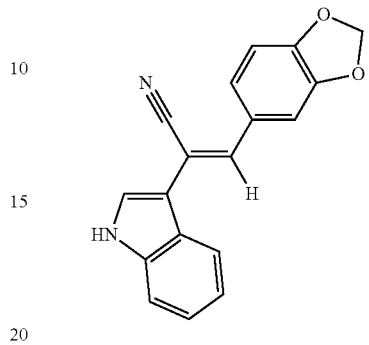

To a solution of sodium ethanolate [prepared from sodium (50 mg, 2.3 mmol, 1.7 eq.) in anhydrous ethanol (4 mL)] were added, under an argon atmosphere, (1H-indol-3-yl)-acetonitrile (200 mg, 1.3 mmol, 1.0 eq.) and, after 30 minutes stirring, benzo[1,3]dioxole-5-carbaldehyde (230 mg, 1.5 mmol, 1.2 eq.). The reaction apparatus was protected from light and the mixture stirred at room temperature for 48 hours. The solvent was removed under reduced pressure, and the residue was triturated with diethyl and washed with ethanol to afford the compound (11) as a yellow powder (130 mg, 35%); $^1$H NMR (DMSO, 500 MHz): δ (ppm): 6.12 (2H, s, 2H2"), 7.06 (1H, d, $J_{7''-6''}=7.9$ Hz, H7"), 7.16 (1H, t, $J_{5'-4'}=J_{5'-6'}=7.6$ Hz, H5'), 7.22 (1H, t, $J_{6'-5'}=J_{6'-7'}=7.6$ Hz, H6'), 7.43 (1H, d, $J_{6''-7''}=7.9$ Hz, H6"), 7.49 (1H, s, H7"), 7.56 (1H, s, H4"), 7.66 (1H, s, H3), 7.74 (1H, s, H2'), 8.01 (1H, d, $J_{4'-5'}=7.6$ Hz, H4'); $^{13}$C NMR (DMSO, 75.5 MHz): δ (ppm): 101.6 (C2"), 103.4 (C2), 107.4 (C4"), 108.7 (C7"), 110.6 (C3'), 112.5 (C7'), 118.8 (C1), 119.4 (C4'), 120.3 (C5'), 122.3 (C6'), 123.7 (C3a'), 124.2 (C6"), 126.1 (C2'), 128.8 (C5"), 136.5 (C3), 137.1 (C7a'), 147.7 (C3a"), 148.3 (C7a"); TLC: Rf=0.60 (heptane 40/EtOAc 60); SM: ESI: m/z: 287.1 ([M−H]$^-$); HRMS (ESI): calcd for $C_{18}H_{11}N_2O_2$: m/z=287.0821. found: 287.0831; IR $v_{max}$ (cm$^{-1}$): 2212 ($v_{CN}$), 3348 ($v_{N-H}$); Mp 168° C.

EXAMPLE 12

(Z)-3-(4-fluoro-phenyl)-2-(1H-indol-3-yl)-acrylonitrile

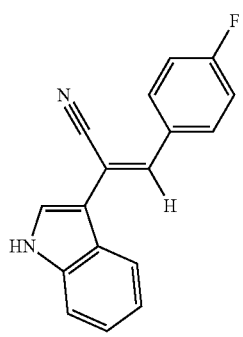 [SMILES: N#C/C(=C\c1ccc(F)cc1)c1c[nH]c2ccccc12]

To a solution of sodium ethanolate [prepared from sodium (50 mg, 2.3 mmol, 1.7 eq.) in anhydrous ethanol (4 mL)] were added, under an argon atmosphere, (1H-indol-3-yl)-acetonitrile (200 mg, 1.3 mmol, 1.0 eq.) and, after 30 minutes stirring, 4-fluoro-benzaldehyde (163 μl, 1.5 mmol, 1.2 eq.). The reaction apparatus was protected from light and the mixture stirred at room temperature for 48 hours. The solvent was removed under reduced pressure, and the residue purified by silica gel flash-column chromatography (eluent: heptane/EtOAc, 95:5 to 80:20). The product was further purified by aluminium oxide pad filtration (eluent: $CH_2Cl_2$/MeOH) to afford the compound (12) as a yellow powder (160 mg, 48%). $^1$H NMR (DMSO, 300 MHz): δ (ppm): 7.17 (1H, t, $J_{5'-4'}=J_{5'-6'}$=7.7 Hz, H5'), 7.23 (1H, t, $J_{6'-5'}=J_{6'-7'}$=7.7 Hz, H6'), 7.35 (2H, t, $J_{3''-2''}=J_{5''-6''}=J_{3''-F}=J_{5''-F}$=8.9 Hz, H3" and H5"), 7.50 (1H, d, $J_{7'-6'}$=7.7 Hz, H7'), 7.77 (1H, s, H3), 7.79 (1H, m, H2'), 7.96 (2H, dd, $J_{2''-3''}=J_{6''-5''}$=8.9 Hz and $J_{2''-F}=J_{6''-F}$=5.6 Hz, H2" and H6"), 8.05 (1H, d, $J_{4'-5'}$=7.7 Hz, H4'), 11.71 (1H, s, indolic H); $^{13}$C NMR (DMSO, 75.5 MHz): δ (ppm): 105.6 (C2), 110.5 (C3), 112.4 (C7'), 115.8 (2C, d, $^2J_{C-F}$=21 Hz, C3" and C5"), 118.3 (C1), 119.5 (C4'), 120.5 (C5'), 122.5 (C6'), 123.6 (C3a'), 126.5 (C2'), 130.7 (2C, d, $^3J_{C-F}$=8 Hz, C2" and C6"), 131.2 (1C, d, $^4J_{C-F}$=3 Hz, C1"), 135.3 (C3), 137.1 (C7a'), 162.3 (1C, $^1J_{C-F}$=248 Hz, C4"); TLC: Rf=0.58 (heptane 50/EtOAc 50); MS: ESI: m/z: 285.1 ([M+Na]$^+$), 317.2 ([M+Na+MeOH]$^+$), 547.3 ([2M+Na]$^+$); HRMS (ESI): calcd for $C_{17}H_{11}N_2$FNa: m/z=285.0804. found: 285.0807; Microanalysis: Calcd for $C_{17}H_{11}N_2$F %: C, 77.85; H, 4.23; F, 7.24; N, 10.68. Found %: C, 77.57; H, 4.15; N, 10.53; IR $v_{max}$ (cm$^{-1}$): 2212 ($v_{CN}$), 3320 ($v_{N-H}$); Mp 132° C.

EXAMPLE 13

(Z)-3-(4-chloro-phenyl)-2-(1H-indol-3-yl)-acrylonitrile

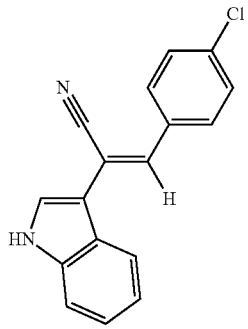 [SMILES: N#C/C(=C\c1ccc(Cl)cc1)c1c[nH]c2ccccc12]

To a solution of sodium ethanolate [prepared from sodium (50 mg, 2.3 mmol, 1.7 eq.) in anhydrous ethanol (4 mL)] were added, under an argon atmosphere, (1H-indol-3-yl)-acetonitrile (200 mg, 1.3 mmol, 1.0 eq.) and, after 30 minutes stirring, 4-chloro-benzaldehyde (216 mg, 1.5 mmol, 1.2 eq.). The reaction apparatus was protected from light and the mixture stirred at room temperature for 48 hours. The solvent was removed under reduced pressure, and the crude purified by silica gel flash-column chromatography (eluent: heptane/EtOAc, 95:5 to 80:20). The residue was triturated with diisopropyl ether and heptane to afford the compound (13) as a yellow powder (200 mg, 56%). $^1$H NMR (DMSO, 300 MHz): δ (ppm): 7.17 (1H, t, $J_{5'-4'}=J_{5'-6'}$=7.5 Hz, H5'), 7.24 (1H, t, $J_{6'-5'}=J_{6'-7'}$=7.5 Hz, H6'), 7.49 (1H, d, $J_{7'-6'}$=7.5 Hz, H7'), 7.57 (2H, d, $J_{3''-2''}=J_{5''-6''}$=8.6 Hz, H3" and H5"), 7.76 (1H, s, H3), 7.81 (1H, s, H2'), 7.92 (2H, d, $J_{2''-3''}=J_{6''-5''}$=8.6 Hz, H2" and H6"), 8.06 (1H, d, $J_{4'-5'}$=7.5 Hz, H4'), 11.74 (1H, s, indolic H); $^{13}$C NMR (DMSO, 75.5 MHz): δ (ppm): 106.5 (C2), 110.6 (C3'), 112.4 (C7'), 118.2 (C1), 119.5 (C4'), 120.5 (C5'), 122.1 (C6'), 123.6 (C3a'), 126.9 (C2'), 128.8 (C3" and C5"), 130.1 (C2" and C6"), 133.6 (C1" and C4"), 134.8 (C3), 137.2 (C7a'); TLC: Rf=0.64 (heptane 50/EtOAc 50); MS: ESI: m/z: 277.1 ([M−H]$^-$); HRMS (ESI): calcd for $C_{17}H_{10}ClN_2$: m/z=277.0533. found: 277.0534; Microanalysis: Calcd for $C_{17}H_{11}ClN_2$, 0.1 $H_2$O %: C, 72.78; H, 4.02; Cl 12.64; N, 9.99. Found %: C, 72.54; H, 4.05; N, 9.39; IR $v_{max}$ (cm$^{-1}$): 2224 ($v_{CN}$), 3296 ($v_{N-H}$); Mp 140° C.

EXAMPLE 14

(Z)-3-(3,5-dimethoxy-phenyl)-2-(5-methoxy-1H-indol-3-yl)-acrylonitrile

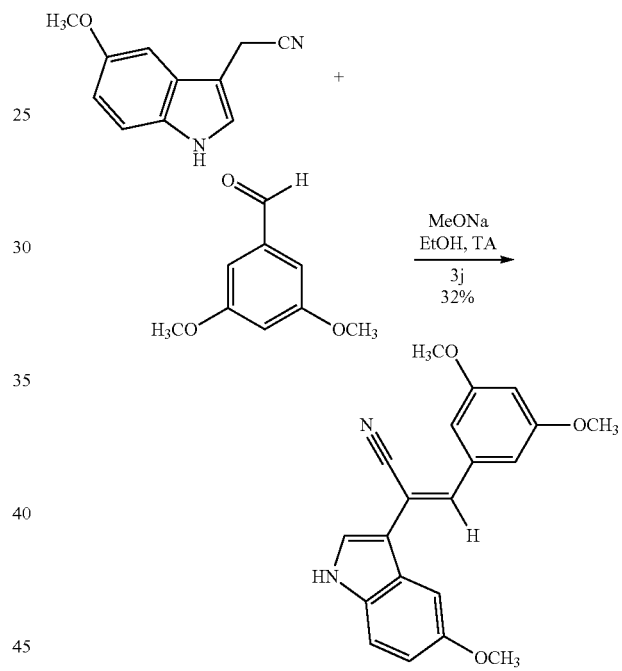

To a solution of sodium methanolate (61 mg, 1.1 mmol, 1.4 eq.) in anhydrous ethanol (10 mL) were added, under an argon atmosphere, (5-methoxy-1H-indol-3-yl)-acetonitrile (150 mg, 0.8 mmol, 1.0 eq.) and, after 30 minutes stirring, 2,4-dimethoxy-benzaldehyde (200 mg, 1.2 mmol, 1.5 eq.). The reaction apparatus was protected from light and the mixture stirred at room temperature for 3 days. The solvent was removed under reduced pressure and the residue purified by silica gel flash-column chromatography (eluent: $CH_2Cl_2$/EtOH, 100:0 to 98:2) to afford, after trituration with diethyl ether, the compound (14) as a yellow powder (85 mg, 32%). TLC: Rf=0.55 ($CH_2Cl_2$ 96/EtOH 4); mp: 141° C.; IR $v_{max}$ (cm-1): 2212 ($v_{CN}$), 3400 ($v_{N-H}$); $^1$H NMR (DMSO, 300 MHz): δ (ppm): 3.81 (6H, s, 3"-methoxy and 5"-methoxy), 3.82 (3H, s, 5'-methoxy), 6.58 (1H, s, H4"), 6.89 (1H, dd, $J_{6'-7'}$=8.9 Hz, $J_{6'-4'}$=2.1 Hz, H6'), 7.11 and 7.12 (2H, m, H2" and H6"), 7.39 (1H, d, $J_{7'-6'}$=8.9 Hz, H7'), 7.44 (1H, d, $J_{4'-6'}$=2.1 Hz, H4'), 7.64 (1H, s, H2'), 7.74 (1H, s, H3), 11.60 (1H, s, H indolic H); $^{13}$C NMR (DMSO, 75.5 MHz): δ (ppm): 55.8 (3"-methoxy and 5"-methoxy), 56.0 (5'-methoxy), 101.8

(C4'), 102.3 (C4"), 106.7 (C2), 107.0 (C2" and C6"), 110.7 (C3'), 112.7 (C6'), 113.6 (C7'), 118.9 (C1), 124.5 (C3a'), 127.6 (C2'), 132.7 (C7a'), 136.5 (C3), 136.9 (C1"), 154.9 (C5'), 161.0 (C3" and C5"); ESI-MS: m/z 357.1 ([M+Na]$^+$); HRESI-MS: m/z 357.1219 (calcd for $C_{20}H_{18}N_2O_3Na$, 357.1205); Anal. Calcd for $C_{20}H_{18}N_2O_2$, 0.2 $H_2O$: C, 71.08; H, 5.49; N, 8.29; O, 15.15. Found: C, 70.89; H, 5.23; N, 8.34.

EXAMPLE 15

(Z)-2-(1H-indol-3-yl)-3-pyrimidin-5-yl-acrylonitrile

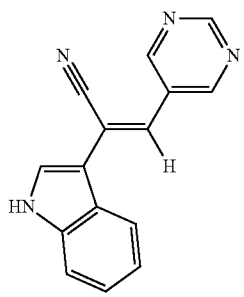 [SMILES: N#C/C(=C\c1cncnc1)c1c[nH]c2ccccc12]

1) Preparation of pyrimidine-5-carbaldehyde

A solution of 5-bromo-pyrimidine (5 g, 31.4 mmol, 1.0 eq.) in anhydrous THF (300 mL) was placed under an argon atmosphere in a three-necked round bottom flask equipped with a low-temperature thermometer. The mixture was cooled to –100° C. in a EtOH/N$_2$(1) bath. To the solution of 5-bromopyridine was added a solution of n-BuLi in hexane (20 mL, 1.6 M, 32.5 mmol, 1.0 eq.). The resulting mixture was stirred for 20 minutes at 100° C. and the organolithium that formed was trapped with a solution of ethyl formate (2.7 mL, 33.5 mmol, 1.1 eq.) in THF (10 mL). The reaction was stirred for another 20 minutes at 100° C. and quenched with a solution of hydrochloric acid in ether (17 mL, 2M, 34 mmol). Then, the cold bath was removed and the mixture stirred at room temperature for 1 hour. The solution was concentrated under reduced pressure, and then treated with water and saturated aqueous sodium carbonate (10 mL). The mixture was extracted with dichloromethane and the organic layer was dried over MgSO$_4$. The solvent was removed under reduced pressure and the residue purified by silica gel flash-column chromatography (eluent: $CH_2Cl_2$/AcOEt, 60:40 to 50:50) to afford pyrimidine-5-carbaldehyde as beige crystals (1.2 g, 35%).

2) Preparation of (Z)-2-(1H-indol-3-yl)-3-pyrimidin-5-yl-acrylonitrile

To a solution of sodium ethanolate [prepared from sodium (53 mg, 2.3 mmol, 1.8 eq.) and anhydrous ethanol (10 mL)] were added, under an argon atmosphere, (1H-indol-3-yl)-acetonitrile (200 mg, 1.3 mmol, 1.0 eq.) and, after 10 minutes stirring, pyrimidine-5-carbaldehyde (207 mg, 1.9 mmol, 1.5 eq.). The reaction apparatus was protected from light and the mixture stirred at room temperature for 40 hours. The solvent was removed under reduced pressure, and the crude purified by silica gel flash-column chromatography (eluent: $CH_2Cl_2$/MeOH, 1:99 to 2:98). The residue was triturated with diethyl ether to afford the compound (15) as a yellow powder (65 mg, 21%). $^1$H NMR (DMSO, 500 MHz): δ (ppm): 7.22 (1H, t, $J_{5'-6'}=J_{5'-4'}=7.9$ Hz, H5'), 7.27 (1H, t, $J_{6'-5'}=J_{6'-7'}=7.9$ Hz, H6'), 7.53 (1H, d, $J_{7'-6'}=7.9$ Hz, H7'), 7.81 (1H, s, H3), 7.88 (1H, s, H2'), 8.13 (1H, d, $J_{4'-5'}=7.9$ Hz, H4'), 9.19 (1H, s, H2"), 9.25 (1H, s, H4" and H6"), 11.87 (1H, s, indolic H); $^{13}$C NMR (DMSO, 75.5 MHz): δ (ppm): 113.9 and 114.3 (C2 and C3'), 116.5 (C7'), 121.6 (C1), 123.6 (C4'), 124.8 (C5'), 126.7 (C6'), 127.3 (C3a'), 131.9 (C2'), 132.3 (C3), 133.3 (C5"), 141.2 (C7a'), 159.8 (C4" and C6"), 161.4 (C2"); TLC: Rf=0.47 ($CH_2Cl_2$ 96/MeOH 4); MS: ESI: m/z: 245.0 ([M–H]$^-$); HRMS (ESI): calcd for $C_{15}H_9N_4$: m/z=245.0827. found: 245.0818; IR $v_{max}$ (cm$^{-1}$): 2219 ($v_{CN}$); Mp 231° C.

EXAMPLE 16

(Z)-2-(5-methoxy-1H-indol-3-yl)-3-pyrimidin-5-yl-acrylonitrile

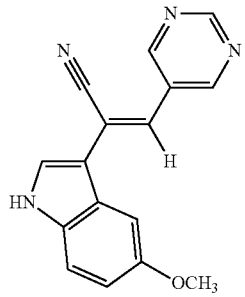 [SMILES: COc1ccc2[nH]cc(/C(C#N)=C/c3cncnc3)c2c1]

To a solution of sodium ethanolate [prepared from sodium (44 mg, 1.9 mmol, 1.8 eq.) and anhydrous ethanol (10 mL)] were added, under an argon atmosphere, (5-methoxy-1H-indol-3-yl)-acetonitrile 8a (200 mg, 1.1 mmol, 1.0 eq.) and, after 10 minutes stirring, pyrimidine-5-carbaldehyde (207 mg, 1.9 mmol, 1.5 eq.). The reaction apparatus was protected from light and the mixture stirred at room temperature for 40 hours. The solvent was removed under reduced pressure, and the crude purified by silica gel flash-column chromatography (eluent: $CH_2Cl_2$/MeOH, 2:98 to 3:97). The residue was triturated with diethyl ether to afford the compound (16) as a yellow powder (60 mg, 20%). $^1$H NMR (DMSO, 500 MHz): δ (ppm): 3.84 (3H, s, 5'-methoxy), 6.92 (1H, dd, $J_{6'-7'}=8.5$ Hz, $J_{6'-4'}=1.8$ Hz, H6'), 7.42 (1H, d, $J_{7'-6'}=8.5$ Hz, H7'), 7.52 (1H, d, $J_{4'-6'}=1.8$ Hz, H4'), 7.74 (1H, s, H3), 7.83 (1H, s, H2'), 9.18 (1H, s, H2'), 9.24 (1H, s, H4" and H6"), 11.74 (1H, s, indolic H); $^{13}$C NMR (DMSO, 75.5 MHz): δ (ppm): 59.6 (5'-methoxy), 106.1 (C4'), 114.0 and 114.1 (C2 and C3'), 116.4 (C6'), 117.2 (C7'), 121.6 (C1), 127.8 (C3a'), 131.9 (C3), 132.3 (C2'), 133.4 (C5"), 136.3 (C7a'), 158.6 (C5'), 159.8 (C4" and C6"), 161.4 (C2"); TLC: Rf=0.24 ($CH_2Cl_2$ 96/MeOH 4); MS: ESI: m/z: 275.1 ([M–H]$^-$); HRMS (ESI): calcd for $C_{16}H_{11}N_4O$: m/z=275.0933. found: 275.0922; IR $v_{max}$ (cm$^{-1}$): 2217 ($v_{CN}$); Mp 214° C.

EXAMPLE 17

2-(1H-indol-3yl-)-3-pyridin-3-yl-propionitrile

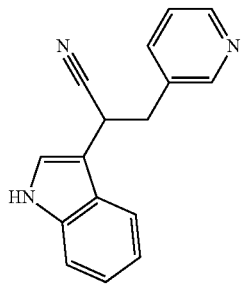

To a solution of (Z)-2-(1H-indol-3-yl)-3-pyridin-3-yl-acrylonitrile (compound of example 2) (200 mg, 0.82 mmol, 1 eq.) in a mixture of THF (3 mL) and methanol (0.6 mL) was added, under an argon atmosphere, sodium borohydride (69 mg, 1.83 mmol, 3 eq.). The reaction mixture was stirred under microwave irradiation for 60 minutes at 115° C. and then, quenched with brine after cooling to room temperature. The mixture was extracted with ethyl acetate and the organic layer was washed with water and saturated aqueous ammonium chloride, and then dried over MgSO$_4$. The solvent was removed under reduced pressure, and the residue purified by silica gel flash-column chromatography (eluent: heptane/EtOAc, 60:40 to 20:80) to afford the compound (17) as a beige powder (80 mg, 40%). $^1$H NMR (DMSO, 500 MHz): δ (ppm): 3.32 (2H, m, 2H3), 4.77 (1H, t, J$_{2-3}$=7.3 Hz, H2), 7.07 (1H, t, J$_{5'-6'}$=J$_{5'-4'}$=7.9 Hz, H5'), 7.33 (2H, m, 112' and H5''), 7.41 (1H, d, J$_{7'-6'}$=7.9 Hz, H7'), 7.70 (2H, d, J$_{4'-5'}$=7.9 Hz, J$_{4''-5''}$=7.9 Hz, H4' and H4''), 7.45 (2H, m, H2'' and H6''), 11.17 (1H, s, indolic H); $^{13}$C NMR (DMSO, 75.5 MHz): δ (ppm): 29.4 (C2), 35.7 (C3), 108.1 (C3'), 111.9 (C7'), 118.3 (C4'), 119.1 (C5'), 121.0 (C1), 121.7 (C6'), 123.3 (C5''), 123.8 (C2'), 125.1 (C3a'), 133.1 (C3''), 136.3 (C7a'), 136.7 (C4''), 148.0 (C6''), 150.2 (C2''). TLC: Rf=0.15 (heptane 30/EtOAc 70). SM: ESI: m/z: 248.1 ([M+H]$^+$); HRMS (ESI): calcd for C$_{16}$H$_{14}$N$_3$: m/z=248.1188. found: 248.1195; IR ν$_{max}$ (cm$^{-1}$): 2239 (ν$_{CN}$); Mp138° C.

EXAMPLE 18

2-(5-methoxy-1H-indol-3-yl)-3-pyridin-3-yl-propionitrile

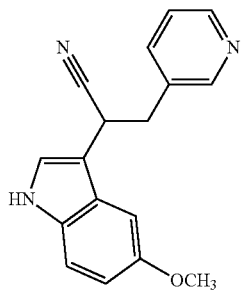 [SMILES: COc1ccc2[nH]cc(C(C#N)Cc3cccnc3)c2c1]

To a solution of (Z)-2-(5-methoxy-1H-indol-3-yl)-3-pyridin-3-yl-acrylonitrile (compound of example 4) (150 mg, 0.55 mmol, 1 eq.) in a mixture of THF (6 mL) and methanol (1.2 mL) was added, under an argon atmosphere, sodium borohydride (69 mg, 1.83 mmol, 3 eq.). The reaction mixture was heated at 60° C. A second amount of sodium borohydride (1 eq.) was added after stirring for 19 hours. The reaction was pursued for 22 hours (41 hours overall) at 60° C. and then, quenched with brine after cooling to room temperature. The mixture was extracted with ethyl acetate and the organic layer was washed with water and saturated aqueous ammonium chloride, and then dried over MgSO$_4$. The solvent was removed under reduced pressure, and the residue purified by silica gel flash-column chromatography (eluent: heptane/EtOAc, 60:40 to 20:80) to afford the compound (18) as a beige powder (115 mg, 75%). $^1$H NMR (DMSO, 300 MHz): δ (ppm): 3.31 (2H, m, 2H3), 3.77 (3H, s, 5'-methoxy), 4.77 (1H, t, J$_{2-3}$=7.5 Hz, H2), 6.78 (1H, dd, J$_{6'-7'}$=8.8 Hz, J$_{6'-4'}$=2.4 Hz, H6'), 7.12 (1H, d, J$_{4'-6'}$=2.4 Hz, H4'), 7.28 (1H, s, H2), 7.29 (1H, d, J$_{7'-6'}$=8.8 Hz, H7'), 7.32 (1H, dd, J$_{5''-4''}$=7.8 Hz, J$_{5''-6''}$=4.8 Hz, H5''), 7.69 (1H, dt, J$_{4''-5''}$=7.8 Hz, J$_{4''-6''}$=J$_{4''-2''}$=2.1 Hz, H4''), 8.45 (2H, m, H2'' and H6''), 11.01 (1H, s, indolic H). $^{13}$C NMR (DMSO, 75.5 MHz): δ (ppm): 29.24 (C2), 35.64 (C3), 55.4 (5'-methoxy), 100.1 (C4'), 107.9 (C3'), 111.8 (C6'), 112.6 (C7'), 121.0 (C1), 123.3 (C5''), 124.3 (C2'), 125.5 (C3a'), 131.3 (C7a'), 133.1 (C3''), 136.7 (C4''), 148.0 (C6''), 150.3 (C2''), 153.4 (C5'). TLC: Rf=0.13 (heptane 30/EtOAc 70). MS: ESI: m/z: 278.1 ([M+H]$^+$), 300.1 ([M+Na]$^+$); HRMS (ESI): calcd for C$_{17}$H$_{16}$N$_3$O: m/z=278.1293. found: 278.1304; IR ν$_{max}$ (cm$^{-1}$): 2237 (ν$_{CN}$). Mp129° C.

EXAMPLE 19

(Z)-3-(1H-indol-3-yl)-2-pyridin-3-yl-acrylonitrile

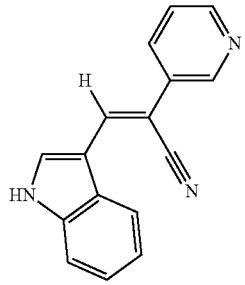 [SMILES: N#C/C(=C\c1c[nH]c2ccccc12)c1cccnc1]

To a solution of sodium ethanolate [prepared from sodium (64 mg, 2.8 mmol, 1.6 eq.) in anhydrous ethanol (15 mL)] were added, under an argon atmosphere, pyridin-3-yl-acetonitrile (235 μl, 2.2 mmol, 1.6 eq.) and, after 10 minutes stirring, 1H-indole-3-carbaldehyde (200 mg, 1.4 mmol, 1.0 eq.). The reaction apparatus was protected from light and the mixture stirred at ambient temperature. Pyridine-3-acetonitrile (1.0 eq.) and sodium (1.5 eq.) were added after stirring for 21 h, and just sodium (1.5 eq.) after stirring for 47 h. The reaction was pursued for 89 hours (136 hours overall) at room temperature, the solvent removed under reduced pressure, and the crude purified by silica gel flash-column chromatography (eluent: CH$_2$Cl$_2$/MeOH, 1:99 to 3:97). The residue was triturated with dichloromethane to afford the compound (19) as a yellow powder (230 mg, 68%). $^1$H NMR (DMSO, 300 MHz): δ (ppm): 7.20 (1H, t, J$_{5'-6'}$=J$_{5'-4'}$=7.2 Hz, H5'), 7.25 (1H, t, J$_{6'-5'}$=J$_{6'-7'}$=7.2 Hz, H6'), 7.49 (1H, J$_{5''-4''}$=8.1 Hz, J$_{5''-6''}$=4.8 Hz, H5''), 7.53 (1H, d, J$_{7'-6'}$=7.2 Hz, H7'), 8.11 (1H, d, J$_{4'-5'}$=7.2 Hz, H4'), 8.16 (1H, d, J$_{4''-5''}$=8.1 Hz, H4''), 8.37 (1H, s, H), 8.42 (1H, s, H2'), 8.54 (dd, J$_{6''-5''}$=4.8 Hz, $J_{6''-4''}$=1.4 Hz, H6''), 8.99 (d, $J_{2''-4''}$=2.4 Hz, H2''), 12.06 (1H, s, indolic H). $^{13}$C NMR (DMSO, 75.5 MHz): δ (ppm): 98.9 (C3'), 110.8 (C2), 112.3 (C7'), 118.9 (C4'), 119.3 (C1), 120.8 (C5'), 122.9 (C6'), 123.8 (C5''), 127.2 (C3a'), 127.7 (C2'), 130.4 (C3''), 132.2 (C4''), 135.8 (C7a'), 136.2 (C3), 146.0 (C2''), 148.5 (C6''). TLC: Rf=0.32 (CH$_2$Cl$_2$ 98/MeOH 2). MS: ESI: 244.0 [M−H]$^-$HRMS (ESI): calcd for C$_{16}$H$_{10}$N$_3$: m/z=244.0875. found: 244.0880. Microanalysis: Calcd for C$_{16}$H$_{11}$N$_3$, 0.1 H$_2$O %: C, 77.78; H, 4.57; N, 17.01 Found %: C, 77.71; H, 4.73; N, 17.16; IR $ν_{max}$ (cm$^{-1}$): 2205 ($ν_{CN}$). Mp189° C.

EXAMPLE 20

3-(1-cyano-2-(pyridin-3-yl)vinyl)-1H-indol-5-yl-acetate

The 3-(1-cyano-2-(pyridin-3-yl)vinyl)-1H-indol-5-yl-acetate can be prepared according to scheme below.

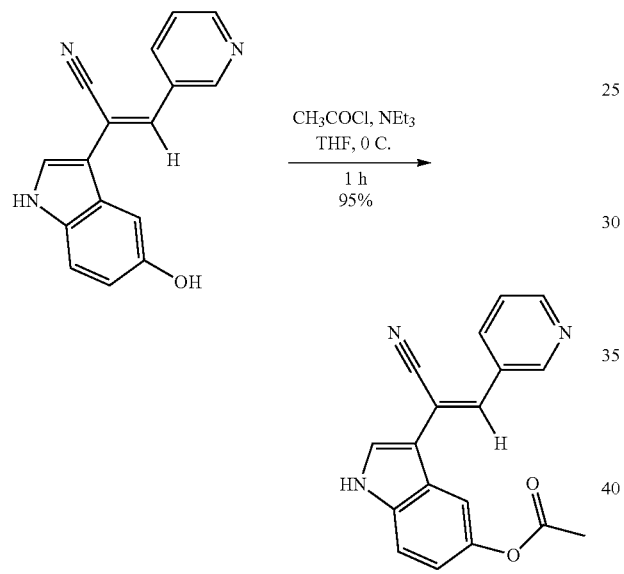

1) Preparation of (Z)-2-(5-hydroxy-1H-indol-3-yl)-3-pyridin-3-yl-acrylonitrile

To a mixture of (Z)-2-(5-methoxy-1H-indol-3-yl)-3-pyridin-3-yl-acrylonitrile (compound of example 4) (175 mg, 0.6 mmol, 1.0 eq.) in anhydrous dichloromethane (2 mL) cooled to −78° C. (dry ice/ethanol bath) was added, under an argon atmosphere, a 1M boron tribromide solution in dichloromethane (2 mL, 2.0 mmol, 3.2 eq.). The reaction mixture was stirred at ambient temperature for 18 hours ant then quenched with ethanol. The solvent was removed under reduced pressure and the residue purified by silica gel flash-column chromatography (eluent: CH$_2$Cl$_2$/MeOH, 95:5 to 93:7) to afford (Z)-2-(5-hydroxy-1H-indol-3-yl)-3-pyridin-3-yl-acrylonitrile as a yellow powder (150 mg, 91%).

2) Preparation of 3-(1-cyano-2-(pyridin-3-yl)vinyl)-1H-indol-5-yl-acetate

To a solution of (Z)-2-(5-hydroxy-1H-indol-3-yl)-3-pyridin-3-yl-acrylonitrile (100 mg, 0.38 mmol, 1.0 eq.) in anhydrous THF (10 mL) maintained at 0° C. were added, under an argon atmosphere, triethylamine (58 μL, 0.42 mmol, 1.1 eq.) and, after 20 minutes stirring, acetyl chloride (30 μL, 0.42 mmol, 1.1 eq.). The reaction apparatus was protected from light and the mixture was stirred at 0° C. for 1 hour, and then quenched with a saturated aqueous ammonium chloride solution. The mixture was extracted with ethyl acetate and the organic layer was washed with brine, and then dried over MgSO$_4$. The solvent was removed under reduced pressure, and the residue purified by silica gel flash-column chromatography (eluent: CH$_2$Cl$_2$/EtOH, 98:2 to 92:8) to afford, after triturating with diethyl ether, the compound (20) as a yellow powder (110 mg, 95%). TLC: Rf=0.30 (CH$_2$Cl$_2$ 96/EtOH 4); mp: 228° C.; IR $ν_{max}$ (cm-1): 1754 ($ν_{C=O}$), 2218 ($ν_{CN}$); $^1$H NMR (DMSO, 300 MHz): δ (ppm): 2.30 (3H, s, acetyl CH$_3$), 7.01 (1H, dd, $J_{6-7}$=8.9 Hz, $J_{6-4}$=1.9 Hz, H6), 7.51 (1H, d, $J_{7-6}$=8.9 Hz, H7), 7.54 (1H, dd, $J_{5'-4''}$=8.1 Hz, $J_{5''-6''}$=4.9 Hz, H5''), 7.77 (1H, s, H3), 7.81 (1H, d, $J_{4-6}$=1.9 Hz, H4), 7.91 (1H, s, H2), 8.33 (1H, d, $J_{4''-5''}$=8.1 Hz, H4''), 8.59 (1H, d, $J_{6''-5''}$=4.9 Hz, H6''), 8.99 (1H, d, $J_{2''-4''}$=1.3 Hz, H2''), 11.90 (1H, s, H indolic H); $^{13}$C NMR (DMSO, 75.5 MHz): δ (ppm): 21.4 (acetyl CH$_3$), 108.2 (C2'), 111.1 (C3), 112.5 (C6), 113.4 (C7), 117.8 (C4), 118.4 (C1'), 124.0 (C3a'), 124.1 (C5''), 129.0 (C2), 131.2 (C3''), 133.3 (C3'), 135.1 (C4''), 135.5 (C7a'), 145.5 (C5), 150.1 (C6''), 150.5 (C2''), 170.3 (acetyl CO); ESI-MS: m/z 304.1 ([M+H]$^+$), 326.1 ([M+Na]$^+$); HRESI-MS: m/z 304.1091 (calcd for C$_{18}$H$_{14}$N$_3$O$_2$, 304.1086), 326.0895 (calcd for C$_{18}$H$_{13}$N$_3$O$_2$Na, 326.0905); Anal. Calcd for C$_{18}$H$_{13}$N$_3$O$_2$, 0.2 H$_2$O: C, 70.44; H, 4.40; N, 13.69; O, 11.47. Found: C, 70.51; H, 4.43; N, 13.43.

EXAMPLE 21

3-(1-cyano-2-(pyridin-3-yl)vinyl)-1H-indol-5-yl-methoxyacetate

The 3-(1-cyano-2-(pyridin-3-yl)vinyl)-1H-indol-5-yl-methoxyacetate can be prepared according to scheme below.

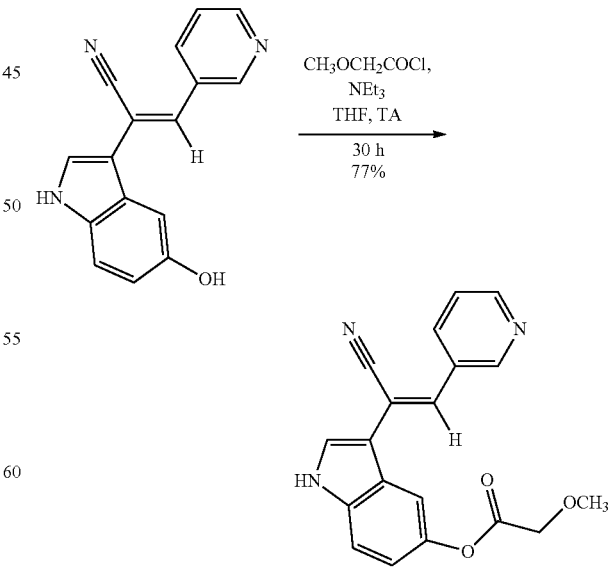

To a solution of (Z)-2-(5-hydroxy-1H-indol-3-yl)-3-pyridin-3-yl-acrylonitrile (see example 20) (80 mg, 0.31 mmol, 1.0 eq.) in anhydrous THF (10 mL) maintained at 0° C. were added, under an argon atmosphere, triethylamine (94 μL, 0.68 mmol, 2.2 eq.) and, after 20 minutes stirring, 2-methoxyacetyl chloride (62 μL, 0.68 mmol, 2.2 eq.). The reaction apparatus was protected from light and the mixture was stirred at room temperature for 30 hours, and then quenched with a saturated aqueous ammonium chloride solution. The mixture was extracted with ethyl acetate and the organic layer was washed with brine, and then dried over MgSO$_4$. The solvent was removed under reduced pressure, and the residue purified by silica gel flash-column chromatography (eluent: heptane/EtOAc, 60:40 to 30:70) to afford, after trituration with diethyl ether, the compound (21) as a yellow powder (80 mg, 77%). mp: 184° C.; IR $\nu_{max}$ (cm-1): 1766 ($\nu_{C=O}$), 2218 ($\nu_{CN}$); $^1$H NMR (DMSO, 300 MHz): δ (ppm): 3.41 (3H, s, methoxy CH$_3$), 4.37 (2H, s, CH$_2$), 7.05 (1H, dm, $J_{6-7}$=8.9 Hz, H6), 7.53 (1H, d, $J_{7-6}$=8.9 Hz, H7), 7.55 (1H, m, H5"), 7.77 (1H, s, H3), 7.85 (1H, m, H4), 7.92 (1H, s, H2), 8.32 (1H, dm, $J_{4''-5''}$=8.1 Hz, H4"), 8.59 (1H, d, $J_{6''-5''}$=4.9 Hz, H6"), 8.98 (1H, s, H2"), 11.93 (1H, s, H indolic H); $^{13}$C NMR (DMSO, 75.5 MHz): δ (ppm): 59.1 (CH$_2$), 69.5 (methoxy CH$_3$), 108.2 (C2'), 111.1 (C3), 112.4 (C6), 113.5 (C7), 117.6 (C4), 118.4 (C1'), 124.1 (C3a'), 124.2 (C5"), 129.1 (C2), 133.4 (C3"), 133.4 (C3'), 135.2 (C4"), 135.6 (C7a'), 144.9 (C5), 150.2 (C6"), 150.4 (C2"), 170.1 (acetyl CO); ESI-MS: m/z 334.1 ([M+H]$^+$), 356.1 ([M+Na]$^+$); HRESI-MS: m/z 356.1023 (calcd for C$_{19}$H$_{15}$N$_3$O$_3$Na, 356.1011).

EXAMPLE 22

(Z)-2-(5-ethoxy-1H-indol-3-yl)-3-pyridin-3-yl-acrylonitrile

The (Z)-2-(5-ethoxy-1H-indol-3-yl)-3-pyridin-3-yl-acrylonitrile can be prepared according to scheme below.

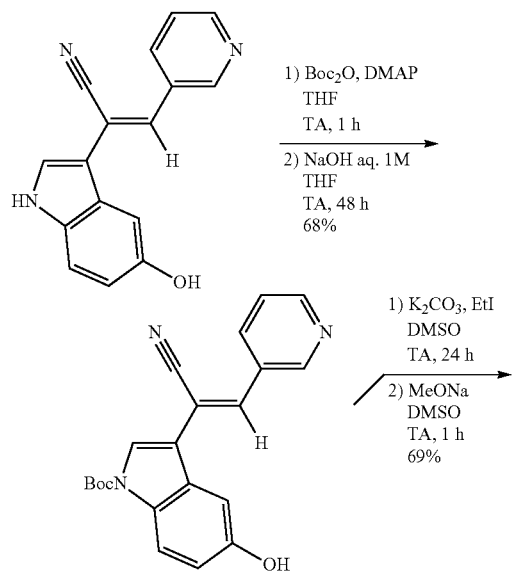

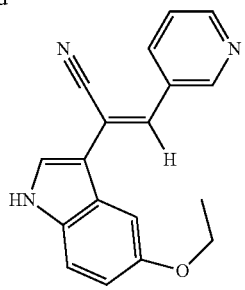

1) Preparation of tert-butyl 3-(1-cyano-2-(pyridin-3-yl)vinyl)-5-hydroxy-1H-indole-1-carboxylate To a solution of (Z)-2-(5-hydroxy-1H-indol-3-yl)-3-pyridin-3-yl-acrylonitrile (see example 20) (850 mg, 3.3 mmol, 1.0 eq.) and (Boc)$_2$O (1.53 mL, 7.2 mmol, 2.2 eq.) in anhydrous THF (60 mL) was added, under an argon atmosphere, DMAP (80 mg, 0.65 mmol, 0.2 eq.). The mixture was stirred for 1 hour, and then quenched with aqueous bicarbonate solution. The organic layer was washed with water and brine, dried over MgSO$_4$ and then, evaporated. To the residue taken up in THF (30 mL) was added a 1 M aqueous sodium hydroxide solution (30 mL). The mixture was stirred at room temperature for 48 hours and then, quenched with a saturated aqueous ammonium chloride solution. The mixture was extracted with ethyl acetate and the organic layer was washed dried over MgSO$_4$. The solvent was removed under reduced pressure, and the residue purified by silica gel flash-column chromatography (eluent: CH$_2$Cl$_2$/EtOH, 98:2 to 96:4) to afford tert-butyl 3-(1-cyano-2-(pyridin-3-yl)vinyl)-5-hydroxy-1H-indole-1-carboxylate as yellow specks (800 mg, 68%).

2) Preparation of (Z)-2-(5-ethoxy-1H-indol-3-yl)-3-pyridin-3-yl acrylonitrile

To a solution of tert-butyl 3-(1-cyano-2-(pyridin-3-yl)vinyl)-5-hydroxy-1H-indole-1-carboxylate (110 mg, 0.30 mmol, 1.0 eq.) and ethyl iodide (32 μL, 0.40 mmol, 1.3 eq.) in DMSO (8 mL) was added potassium carbonate (100 mg, 0.73 mmol, 2.4 eq.). The reaction apparatus was protected from light and the mixture was stirred at room temperature for 24 hours before sodium methanolate (41 mg, 0.75 mmol, 2.5 eq.) was added. The reaction was pursued at room temperature for 1 hour, and then quenched with a saturated aqueous ammonium chloride solution. The mixture was extracted with ethyl acetate and the organic layer was washed with brine, and then dried over MgSO$_4$. The solvent was removed under reduced pressure, and the residue purified by silica gel flash-column chromatography (eluent: heptane/EtOAc, 60:40 to 40:60) to afford, after trituration with diethyl ether, the compound (22) as a yellow powder (60 mg, 69%). mp: 196° C.; IR $\nu_{max}$ (cm-1): 2216 ($\nu_{CN}$); $^1$H NMR (DMSO, 300 MHz): δ (ppm): 1.36 (3H, t, $J_{9'-8'}$=7.0 Hz, 3H9'), 4.10 (2H, q, $J_{8'-9'}$=7.0 Hz, 2H8'), 6.90 (1H, dd, $J_{6'-7'}$=8.9 Hz, $J_{6'-4'}$=2.1 Hz, H6'), 7.40 (1H, d, $J_{7'-6'}$=8.9 Hz, H7'), 7.48 (1H, d, $J_{4'-6'}$=2.1 Hz, H4'), 7.54 (1H, dd, $J_{5''-4''}$=7.9 Hz, $J_{5''-6''}$=4.7 Hz, H5"), 7.74 (1H, s, H3), 7.78 (1H, s, H2'), 8.32 (1H, d, $J_{4''-5''}$=8.1 Hz, H4"), 8.58 (1H, dd, $J_{6''-5''}$=4.8 Hz, $J_{6''-4''}$=1.6 Hz, H6"), 8.98 (1H, d, $J_{2''-4''}$=2.3 Hz, H2"), 11.65 (1H, s, indolic H); $^{13}$C NMR (DMSO, 75.5 MHz): δ (ppm): 15.3 (C9'), 64.1 (C8'), 103.3 (C4'), 108.7 (C2), 110.6 (C3'), 113.3 (C6'), 113.6 (C7'), 118.6 (C1), 124.1 (C5"), 124.5 (C3a'), 128.1 (C2'), 131.4 (C3"), 132.7 (C3 and C7a'), 135.1 (C4"), 150.0 (C6"), 150.4 (C2"), 154.2 (C5'); ESI-MS: m/z 290.1 ([M+H]$^+$), 312.1 ([M+Na]$^+$); HRESI-MS: m/z 290.1293 (calcd for $C_{18}H_{16}N_3O$, 290.1293).

EXAMPLE 23

(Z)-2-(5-isopropoxy-1H-indol-3-yl)-3-pyridin-3-yl-acrylonitrile

The (Z)-2-(5-isopropoxy-1H-indol-3-yl)-3-pyridin-3-yl-acrylonitrile can be prepared according to scheme below.

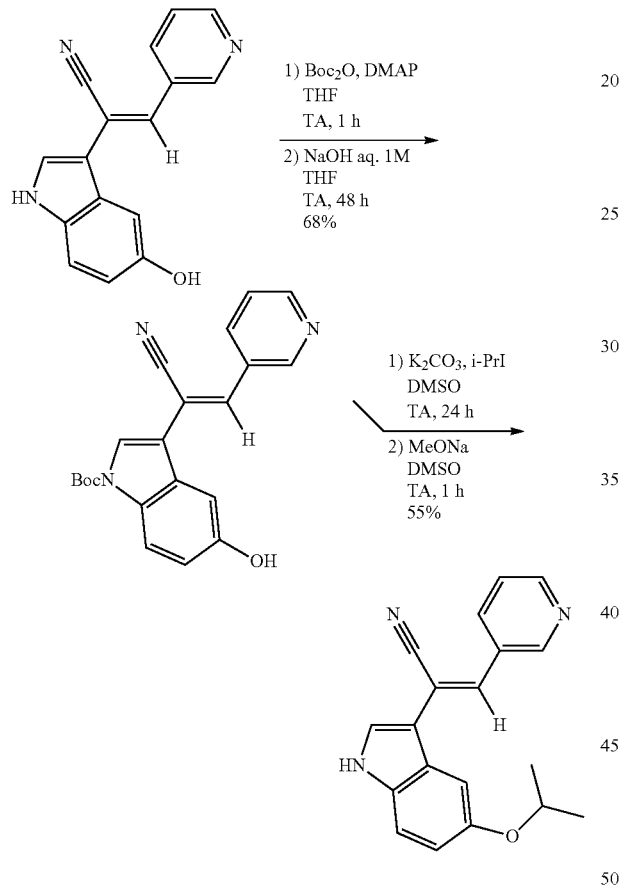

To a solution of tert-butyl 3-(1-cyano-2-(pyridin-3-yl)vinyl)-5-hydroxy-1H-indole-1-carboxylate (see example 22) (110 mg, 0.30 mmol, 1.0 eq.) and isopropyl iodide (40 μL, 0.40 mmol, 1.3 eq.) in DMSO (8 mL) was added potassium carbonate (100 mg, 0.73 mmol, 2.4 eq.). The reaction apparatus was protected from light and the mixture was stirred at room temperature for 24 hours before sodium methanolate (41 mg, 0.75 mmol, 2.5 eq.) was added. The reaction was pursued at room temperature for 1 hour, and then quenched with a saturated aqueous ammonium chloride solution. The mixture was extracted with ethyl acetate and the organic layer was washed with brine, and then dried over $MgSO_4$. The solvent was removed under reduced pressure, and the residue purified by silica gel flash-column chromatography (eluent: heptane/EtOAc, 60:40 to 40:60) to afford, after trituration with diethyl ether, the compound (23) as a yellow powder (50 mg, 55%). TLC: Rf=0.25 (heptane 40/EtOAc 60); mp: 211° C.; IR $v_{max}$ (cm-1): 2218 ($v_{CN}$); $^1$H NMR (DMSO, 300 MHz): δ (ppm): 1.29 (6H, d, $J_{9'-8'}=J_{9'-8'}=6.1$ Hz, 3H9' and 3H10'), 4.65 (1H, h, $J_{8'-9'}=J_{8'-9'}=6.1$ Hz, H8'), 6.90 (1H, dd, $J_{6'-7'}=8.9$ Hz, $J_{6'-4'}=2.1$ Hz, H6'), 7.39 (1H, d, $J_{7'-6'}=8.9$ Hz, H7'), 7.51 (1H, d, $J_{4'-6'}=2.1$ Hz, H4'), 7.54 (1H, dd, $J_{5''-4''}=7.9$ Hz, $J_{5''-6''}=4.9$ Hz, H5"), 7.73 (1H, s, H3), 7.79 (1H, s, H2'), 8.32 (1H, d, $J_{4''-5''}=7.9$ Hz, H4"), 8.59 (1H, dd, $J_{6''-5''}=4.9$ Hz, $J_{6''-4''}=1.2$ Hz, H6"), 8.98 (1H, d, $J_{2''-4''}=1.6$ Hz, H2"), 11.64 (1H, s, indolic H); $^{13}$C NMR (DMSO, 75.5 MHz): δ (ppm): 22.5 (C9' and C10'), 70.7 (C8'), 105.9 (C4'), 108.7 (C2), 110.6 (C3'), 113.6 (C6'), 114.6 (C7'), 118.6 (C1), 124.1 (C5"), 124.6 (C3a'), 128.1 (C2'), 131.4 (C3"), 132.7 (C3), 132.9 (C7a'), 135.1 (C4"), 150.0 (C6"), 150.4 (C2"), 152.9 (C5'); ESI-MS: m/z 304.1 ([M+H]$^+$), 326.1 ([M+Na]$^+$); HRESI-MS: m/z 304.1448 (calcd for $C_{19}H_{18}N_3O$, 304.1450).

EXAMPLE 24

(Z)-2-(5-chloro-1H-indol-3-yl)-3-pyridin-3-yl-acrylonitrile

The (Z)-2-(5-chloro-1H-indol-3-yl)-3-pyridin-3-yl-acrylonitrile can be prepared according to scheme below.

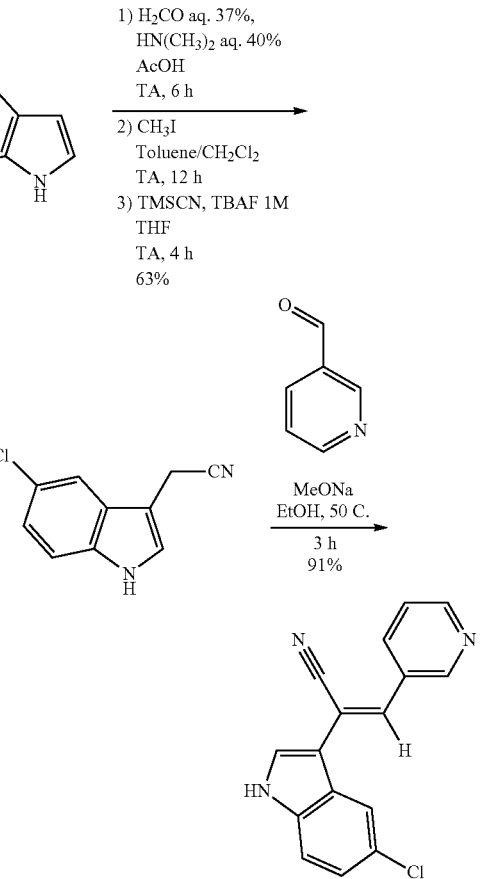

1) Preparation of (5-chloro-1H-indol-3-yl)-acetonitrile

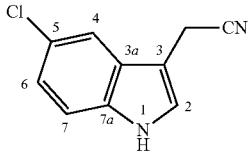 [SMILES: N#CCc1c[nH]c2ccc(Cl)cc12]

To a solution of 5-chloroindole (1.0 g, 6.8 mmol, 1.0 eq.) in a mixture of acetic acid (2 mL) and water (1 mL) were added, at 0° C., formaldehyde (720 µL, 37% in H$_2$O, 8.9 mmol, 1.3 eq) and dimethylamine (1.23 mL, 40% in H$_2$O, 10.9 mmol, 1.7 eq). The mixture was stirred at room temperature for 6 hours and then, quenched with ice and 5 M aqueous sodium hydroxide. The mixture was extracted with dichloromethane and then, the organic layer was dried over MgSO$_4$ and partially evaporated. To the solution gramine in dichloromethane (20 mL) were added, under an argon atmosphere, anhydrous toluene (40 mL) and methyl iodide (824 µL, 13.2 mmol, 2.0 eq.). The mixture was stirred at room temperature for 12 hours and then, concentrated under reduced pressure. To the residue taken up in anhydrous THF (60 mL) were added, under an argon atmosphere, TMSCN (1.25 mL, 9.9 mmol, 1.5 eq.) and TBAF (19.9 mL, 1M, 19.9 mmol, 3.0 eq.). The mixture was stirred at room temperature for 4 hours and then, concentrated under reduced pressure. The crude was taken up in ethyl acetate and the organic layer was washed with aqueous bicarbonate solution and then dried over MgSO$_4$. The solvent was removed under reduced pressure, and the residue purified by silica gel pad filtration (eluent: EtOAc) to afford (5-chloro-1H-indol-3-yl)-acetonitrile as a beige solid (0.80 g, 63%).

2) Preparation of (Z)-2-(5-chloro-1H-indol-3-yl)-3-pyridin-3-yl-acrylonitrile To a solution of sodium methanolate (213 mg, 3.9 mmol, 1.5 eq.) in anhydrous ethanol (40 mL) were added, under an argon atmosphere, (5-chloro-1H-indol-3-yl)-acetonitrile (500 mg, 2.6 mmol, 1.0 eq.) and, after 30 minutes stirring, pyridine-3-carbaldehyde (493 µL, 5.3 mmol, 2.0 eq.). The reaction apparatus was protected from light and the mixture heated at 50° C. for 3 hours. The reaction was allowed to cool to room temperature and then, the solvent was removed under reduced pressure and the crude taken up in ethyl acetate. The organic layer was washed with water and brine, dried over MgSO$_4$ and then, evaporated. The residue was purified by silica gel flash-column chromatography (eluent: CH$_2$Cl$_2$/EtOH, 98:2 to 93:7) to afford the compound (24) as a yellow powder (670 mg, 91%). TLC: Rf=0.30 (CH$_2$Cl$_2$ 96/EtOH 4); IR $\nu_{max}$ (cm-1): 2217 ($\nu_{CN}$); $^1$H NMR (DMSO, 300 MHz): δ (ppm): 7.26 (1H, d, J$_{6'-7'}$=8.9 Hz, H6'), 7.53 (1H, d, J$_{7'-6'}$=8.9 Hz, H7'), 7.55 (1H, m, H5''), 7.84 (1H, s, H3), 7.93 (1H, s, H2'), 8.13 (1H, s, H4'), 8.34 (1H, d, J$_{4''-5''}$=7.9 Hz, H4''), 8.60 (1H, d, J$_{6''-5''}$=4.7 Hz, H6''), 9.00 (1H, s, H2''), 11.99 (1H, s, indolic H); $^{13}$C NMR (DMSO, 75.5 MHz): δ (ppm): 107.8 (C2), 110.7 (C3'), 114.5 (C7'), 118.4 (C1), 119.3 (C4'), 123.2 (C6'), 124.1 (C5''), 125.0 (C3a'), 125.9 (C5'), 129.2 (C2'), 131.2 (C3''), 134.1 (C3), 135.2 (C4''), 136.2 (C7a'), 150.2 (C6''), 150.5 (C2''); ESI-MS: m/z 280.1 ([M+H]$^+$); HRESI-MS: m/z 280.0641 (calcd for C$_{16}$H$_{11}$N$_3$$^{35}$Cl, 280.0642);

Anal. Calcd for C$_{16}$H$_{10}$ClN$_3$, 0.2 H$_2$O: C, 67.83; H, 3.70; N, 14.83. Found: C, 67.88; H, 3.64; N, 14.91.

EXAMPLE 25

(Z)-2-(5-fluoro-1H-indol-3-yl)-3-pyridin-3-yl-acrylonitrile

The (Z)-2-(5-fluoro-1H-indol-3-yl)-3-pyridin-3-yl-acrylonitrile can be prepared according to scheme below.

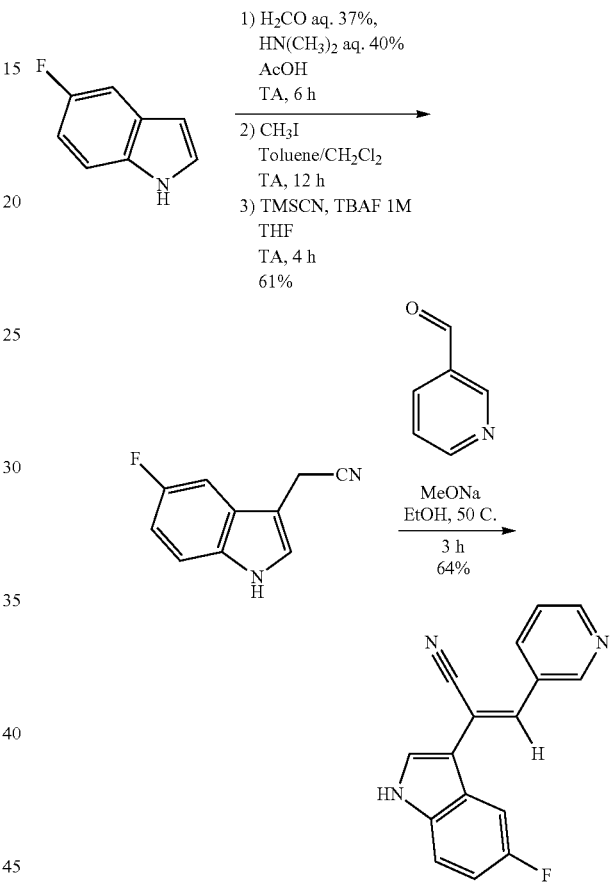

1) Preparation of (5-fluoro-1H-indol-3-yl)-acetonitrile

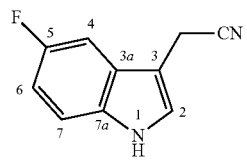

To a solution of 5-fluoroindole (0.9 g, 6.8 mmol, 1.0 eq.) in a mixture of acetic acid (2 mL) and water (1 mL) were added, at 0° C., formaldehyde (720 µL, 37% in H$_2$O, 8.9 mmol, 1.3 eq) and dimethylamine (1.23 mL, 40% in H$_2$O, 10.9 mmol, 1.7 eq). The mixture was stirred at room temperature for 6 hours and then, quenched with ice and 5 M aqueous sodium hydroxide. The mixture was extracted with dichloromethane and then, the organic layer was dried over MgSO$_4$ and partially evaporated. To the solution gramine in dichloromethane (20 mL) were added, under an argon atmosphere, anhydrous toluene (40 mL) and methyl iodide (824 µL, 13.2 mmol, 2.0 eq.). The mixture was stirred at room temperature for 12 hours and then, concentrated under reduced pressure. To the residue taken up in anhydrous THF (60 mL) were added, under an argon atmosphere, TMSCN (1.25 mL, 9.9 mmol, 1.5 eq.) and TBAF (19.9 mL, 1M, 19.9 mmol, 3.0 eq.). The mixture was stirred at room temperature for 4 hours and then, concentrated under reduced pressure. The crude was taken up in ethyl acetate and the organic layer was washed with aqueous bicarbonate solution and then dried over MgSO$_4$. The solvent was removed under reduced pressure, and the residue purified by silica gel flash-column chromatography (eluent: heptane/CH$_2$Cl$_2$, 80:20 to 40:60) to afford (5-fluoro-1H-indol-3-yl)-acetonitrile as beige oil (0.70 g, 61%).

2) Preparation of (Z)-2-(5-fluoro-1H-indol-3-yl)-3-pyridin-3-yl-acrylonitrile

To a solution of sodium methanolate (233 mg, 4.3 mmol, 1.5 eq.) in anhydrous ethanol (40 mL) were added, under an argon atmosphere, (5-fluoro-1H-indol-3-yl)-acetonitrile (500 mg, 2.9 mmol, 1.0 eq.) and, after 30 minutes stirring, pyridine-3-carbaldehyde (539 µL, 5.7 mmol, 2.0 eq.). The reaction apparatus was protected from light and the mixture heated at 50° C. for 3 hours. The reaction was allowed to cool to room temperature and then, the solvent was removed under reduced pressure and the crude taken up in ethyl acetate. The organic layer was washed with water and brine, dried over MgSO$_4$ and then, evaporated. The residue was purified by silica gel flash-column chromatography (eluent: CH$_2$Cl$_2$/EtOH, 98:2 to 95:5) to afford the compound (25) as a yellow powder (480 mg, 64%). TLC: Rf=0.35 (CH$_2$Cl$_2$ 96/EtOH 4); IR $\nu_{max}$ (cm-1): 2215 ($\nu_{CN}$); $^1$H NMR (DMSO, 300 MHz): δ (ppm): 7.11 (1H, td, $J_{6'-7'}$=$J_{6'-F}$=9.0 Hz, $J_{6'-4'}$=2.1 Hz, H6'), 7.49 to 7.56 (2H, m, H7' and H5"), 7.79 (1H, s, H3), 7.90 (1H, m, H4'), 7.91 (1H, s, H2'), 8.34 (1H, d, $J_{4"-5"}$=8.1 Hz, H4"), 8.59 (1H, dd, $J_{6"-5"}$=4.7 Hz, $J_{6"-4"}$=1.3 Hz, H6"), 9.01 (1H, d, $J_{2"-4"}$=1.9 Hz, H2"), 11.89 (1H, s, indolic H); $^{13}$C NMR (DMSO, 75.5 MHz): δ (ppm): 105.3 (1C, d, $^2J_{C-F}$=25 Hz, C4'), 108.1 (C2), 111.3 (1C, d, $^2J_{C-F}$=27 Hz, C6'), 114.1 (1C, d, $^3J_{C-F}$=10 Hz, C7'), 118.4 (C1), 124.1 (C3a' and C5"), 129.5 (C2'), 131.2 (C3"), 133.3 (C3), 134.4 (C7a'), 135.1 (C4"), 150.1 (C6"), 150.5 (C2"), 158.3 (1C, d, $^1J_{C-F}$=233 Hz, C5'); ESI-MS: m/z 264.1 ([M+H]$^+$); HRESI-MS: m/z 264.0940 (calcd for C$_{16}$H$_{11}$N$_3$F, 264.0937).

EXAMPLE 26

(Z)-2-(6-methoxy-1H-indol-3-yl)-3-pyridin-3-yl-acrylonitrile

The (Z)-2-(6-methoxy-1H-indol-3-yl)-3-pyridin-3-yl-acrylonitrile can be prepared according to scheme below.

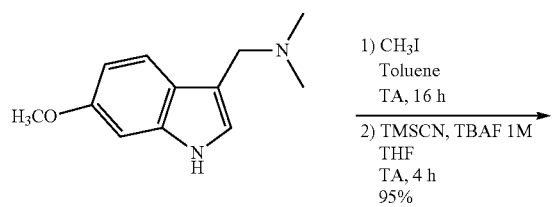

1) Preparation of (6-methoxy-1H-indol-3-yl)-acetonitrile

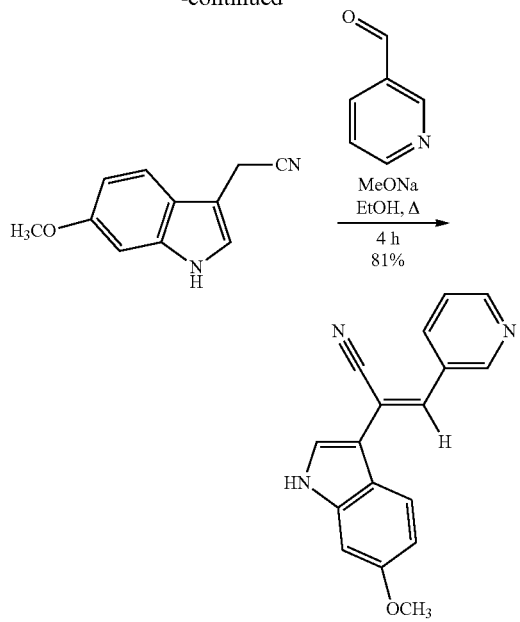

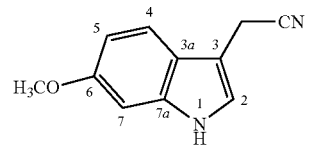

To a solution of 6-methoxygramine (1.0 g, 4.9 mmol, 1.0 eq.) in a mixture of anhydrous dichloromethane (16 mL) and toluene (30 mL) was added, under an argon atmosphere, methyl iodide (610 µL, 9.8 mmol, 2.0 eq.). The mixture was stirred at room temperature for 16 hours and then, concentrated under reduced pressure. To the residue taken up in anhydrous THF (40 mL) were added, under an argon atmosphere, TMSCN (920 µL, 7.3 mmol, 1.5 eq.) and TBAF (14.7 mL, 1M, 14.7 mmol, 3.0 eq.). The mixture was stirred at room temperature for 4 hours and then, concentrated under reduced pressure. The crude was taken up in ethyl acetate and the organic layer was washed with aqueous bicarbonate solution and then dried over MgSO$_4$. The solvent was removed under reduced pressure, and the residue purified by silica gel pad filtration (eluent: EtOAc) to afford (6-methoxy-1H-indol-3-yl)-acetonitrile as a beige powder (0.87 g, 95%). mp: 100° C.

2) Preparation of (Z)-2-(6-methoxy-1H-indol-3-yl)-3-pyridin-3-yl-acrylonitrile

To a solution of sodium methanolate (300 mg, 5.6 mmol, 2.1 eq.) in anhydrous ethanol (40 mL) were added, under an argon atmosphere, (6-methoxy-1H-indol-3-yl)-acetonitrile (500 mg, 2.7 mmol, 1.0 eq.) and pyridine-3-carbaldehyde (379 µL, 4.0 mmol, 1.5 eq.). The reaction apparatus was protected from light and the mixture heated at reflux for 4 hours. The reaction was allowed to cool to room temperature and then, the solvent was removed under reduced pressure and the crude taken up in ethyl acetate. The organic layer was washed with water and brine, dried over MgSO$_4$ and then, evaporated. The residue was purified by silica gel flash-column chromatography (eluent: CH$_2$Cl$_2$/EtOH, 98:2 to 96:4) to afford the compound (26) as a yellow powder (600 mg, 81%). TLC: Rf=0.25 (CH$_2$Cl$_2$ 96/EtOH 4); IR $\nu_{max}$ (cm-1): 2216 ($\nu_{CN}$); $^1$H NMR (DMSO, 300 MHz): δ (ppm): 3.81 (3H, s, 6'-methoxy), 6.90 (1H, dd, J$_{5'-4'}$=8.7 Hz, J$_{5'-7'}$=1.9 Hz, H5'), 6.99 (1H, d, J$_{7'-5'}$=1.9 Hz, H7'), 7.54 (1H, dd, J$_{5''-4''}$=7.9 Hz, J$_{5''-6''}$=4.9 Hz, H5''), 7.70 (1H, s, H2'), 7.77 (1H, s, H3), 7.99 (1H, d, J$_{4'-5'}$=8.7 Hz, H4'), 8.33 (1H, d, J$_{4''-5''}$=7.9 Hz, H4''), 8.58 (1H, d, J$_{6''-5''}$=4.9 Hz, H6''), 8.98 (1H, d, J$_{2''-4''}$=1.7 Hz, H2''), 11.58 (1H, s, indolic H); $^{13}$C NMR (DMSO, 75.5 MHz): δ (ppm): 55.2 (6'-methoxy), 95.3 (C4'), 108.2 (C2), 110.7 (C5' and C3'), 117.7 and 118.0 (C1 and C5'), 120.4 (C4'), 123.6 (C5''), 126.2 (C2'), 130.8 (C3''), 131.8 (C3), 134.5 (C4''), 138.3 (C7a'), 149.5 (C6''), 149.9 (C2''), 156.3 (C5'); ESI-MS: m/z 276.1 ([M+H]$^+$); HRESI-MS: m/z 276.1133 (calcd for C$_{17}$H$_{14}$N$_3$O, 276.1137); Anal. Calcd for C$_{17}$H$_{13}$N$_3$O, 0.1 H$_2$O: C, 73.68; H, 4.80; N, 15.16. Found: C, 73.41; H, 4.97; N, 14.98.

EXAMPLE 27

(Z)-2-(4-methoxy-1H-indol-3-yl)-3-pyridin-3-yl-acrylonitrile

The (Z)-2-(4-methoxy-1H-indol-3-yl)-3-pyridin-3-yl-acrylonitrile can be prepared according to scheme below.

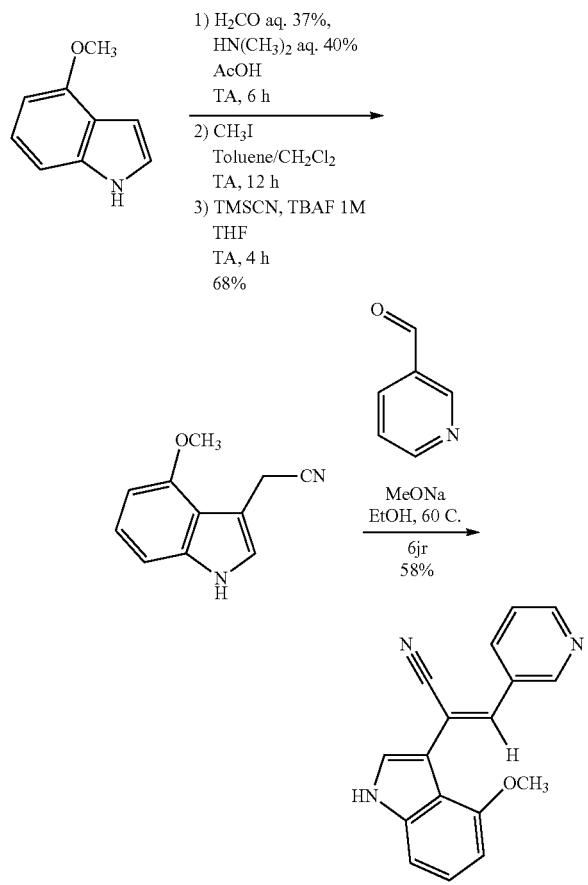

1) Preparation of (4-methoxy-1H-indol-3-yl)-acetonitrile

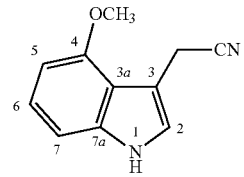 [SMILES: COc1cccc2[nH]cc(CC#N)c12]

To a solution of 4-methoxyindole (1.0 g, 6.8 mmol, 1.0 eq.) in a mixture of acetic acid (2 mL) and water (1 mL) were added, at 0° C., formaldehyde (720 µL, 37% in H$_2$O, 8.9 mmol, 1.3 eq) and dimethylamine (1.23 mL, 40% in H$_2$O, 10.9 mmol, 1.6 eq). The mixture was stirred at room temperature for 6 hours and then, quenched with ice and 5 M aqueous sodium hydroxide. The mixture was extracted with dichloromethane and then, the organic layer was dried over MgSO$_4$ and partially evaporated. To the solution gramine in dichloromethane (20 mL) were added, under an argon atmosphere, anhydrous toluene (40 mL) and methyl iodide (845 µL, 13.6 mmol, 2.0 eq.). The mixture was stirred at room temperature for 12 hours and then, concentrated under reduced pressure. To the residue taken up in anhydrous THF (60 mL) were added, under an argon atmosphere, TMSCN (1.28 mL, 10.2 mmol, 1.5 eq.) and TBAF (20.4 mL, 1M, 20.4 mmol, 3.0 eq.). The mixture was stirred at room temperature for 4 hours and then, concentrated under reduced pressure. The crude was taken up in ethyl acetate and the organic layer was washed with aqueous bicarbonate solution and then dried over MgSO$_4$. The solvent was removed under reduced pressure, and the residue purified by silica gel pad filtration (eluent: EtOAc) to afford (4-methoxy-1H-indol-3-yl)-acetonitrile as a beige solid (0.80 g, 68%).

2) Preparation of (Z)-2-(4-methoxy-1H-indol-3-yl)-3-pyridin-3-yl-acrylonitrile

To a solution of sodium methanolate (261 mg, 4.8 mmol, 1.5 eq.) in anhydrous ethanol (40 mL) were added, under an argon atmosphere, of (4-methoxy-1H-indol-3-yl)-acetonitrile (600 mg, 3.2 mmol, 1.0 eq.) and, after 30 minutes stirring, pyridine-3-carbaldehyde (908 µL, 9.7 mmol, 3.0 eq.). The reaction apparatus was protected from light and the mixture heated at 60° C. Several amounts of sodium methanolate (4×1.0 eq.) and pyridine-3-carbaldehyde (4×1.0 eq.) were added after stirring for 24, 48, 72 and 96 hours respectively. The reaction was pursued for 2 days (6 days overall) at 60° C. and then, the solvent was removed under reduced pressure and the crude taken up in ethyl acetate. The organic layer was washed with water and brine, dried over MgSO$_4$ and then, evaporated. The residue was purified by silica gel flash-column chromatography (eluent: CH$_2$Cl$_2$/EtOH, 98:2 to 97:3) to afford, after trituration with diethyl ether, the compound (27) as a yellow powder (510 mg, 58%). TLC: Rf=0.30 (CH$_2$Cl$_2$ 96/EtOH 4); mp: 177° C.; $^1$H NMR (DMSO, 500 MHz): δ (ppm): 3.90 (3H, s, 4'-methoxy), 6.66 (1H, d, J$_{5'-6'}$=7.9 Hz, H5'), 7.07 (1H, d, J$_{7'-6'}$=7.9 Hz, H7'), 7.14 (1H, t, J$_{6'-5'}$=J$_{6'-7'}$=7.9 Hz, H6'), 7.55 (1H, dd, J$_{5''-4''}$=7.9 Hz, J$_{5''-6''}$=4.9 Hz, H5''), 7.62 (1H, s, H2'), 7.78 (1H, s, H3), 8.31 (1H, d, J$_{4''-5''}$=7.9 Hz, H4''), 8.59 (1H, d, J$_{6''-5''}$=4.9 Hz, H6''), 8.91 (1H, s, H2''), 11.67 (1H, s, indolic H); $^{13}$C NMR (DMSO, 75.5 MHz): δ (ppm): 55.6 (4'-methoxy), 101.4 (C5'), 106.0 (C7'), 108.6 (C2), 111.9 (C3'), 114.7 (C3a'), 119.1 (C1), 124.1

(C5"), 124.3 (C6'), 126.6 (C2'), 131.1 (C3"), 134.9 (C4"), 138.0 (C3), 139.0 (C7a'), 150.3 (C6"), 150.4 (C2"), 153.7 (C4'); ESI-MS: m/z 276.1 ([M+H]$^+$), 298.1 ([M+Na]$^+$); HRESI-MS: m/z 276.1137 (calcd for $C_{17}H_{14}N_3O$, 276.1137).

EXAMPLE 28

(Z)-3-(6-fluoropyridin-3-yl)-2-(5-methoxy-1H-indol-3-yl)-acrylonitrile

The (Z)-3-(6-fluoropyridin-3-yl)-2-(5-methoxy-1H-indol-3-yl)-acrylonitrile can be prepared according to scheme below.

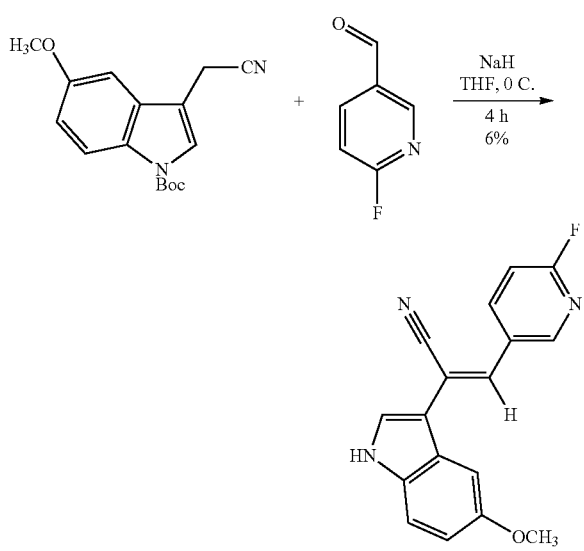

1) Preparation of tert-butyl 3-(cyanomethyl)-5-methoxy-1H-indol-1-carboxylate

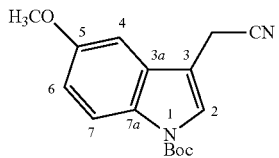

To a solution of (5-methoxy-1H-indol-3-yl)-acetonitrile (2.0 g, 11.0 mmol, 1.0 eq.) and (Boc)$_2$O (3.42 mL, 16.0 mmol, 1.5 eq.) in anhydrous dichloromethane (150 mL) was added, under an argon atmosphere, DMAP (66 mg, 0.54 mmol, 0.05 eq.). The reaction mixture was stirred at room temperature for 1 hour, and then quenched with aqueous bicarbonate solution. The organic layer was washed with water and brine, dried over MgSO$_4$ and then, evaporated to afford tert-butyl 3-(cyanomethyl)-5-methoxy-1H-indol-1-carboxylate as a white powder (3.2 g, quantitative). mp: 130° C.

2) Preparation of (Z)-3-(6-fluoropyridin-3-yl)-2-(5-methoxy-1H-indol-3-yl)-acrylonitrile To a solution of tert-butyl 3-(cyanomethyl)-5-methoxy-1H-indol-1-carboxylate (719 mg, 2.51 mmol, 1.0 eq.) in anhydrous THF (30 mL) was added, under an argon atmosphere, NaH (106 mg, 80%, 3.52 mmol, 1.4 eq.). The mixture was stirred at room temperature for 2 hours, and then cooled to 0° C. before the addition of 6-fluoro-pyridine-3-carbaldehyde (440 mg, 3.52 mmol, 1.4 eq.) in anhydrous THF (6 mL). The reaction apparatus was protected from light and the mixture was stirred at 0° C. for 4 hours, and then quenched with a saturated aqueous ammonium chloride solution. The mixture was stirred again at room temperature for 4 hours and extracted with ethyl acetate. The organic layer was washed with brine and dried over MgSO$_4$. The solvent was removed under reduced pressure, and the residue purified by silica gel flash-column chromatography (eluent: CH$_2$Cl$_2$/EtOH, 98:2) to afford, after trituration with diethyl ether, the compound (28) as a yellow powder (45 mg, 6%). IR $v_{max}$ (cm-1): 2215 ($v_{CN}$); $^1$H NMR (DMSO, 300 MHz): δ (ppm): 3.84 (3H, s, 5'-methoxy), 6.91 (1H, dd, $J_{6'-7'}$=8.9 Hz, $J_{6'-4'}$=2.1 Hz, H6'), 7.36 (1H, dd, $J_{5''-4''}$=8.5 Hz, $J_{5''-F}$=2.1 Hz, H5"), 7.41 (1H, d, $J_{7'-6'}$=8.9 Hz, H7'), 7.49 (1H, d, $J_{4'-6'}$=2.4 Hz, H4'), 7.76 (1H, s, H3), 7.78 (1H, s, H2'), 8.52 (1H, td, $J_{5''-4''}$=$J_{5''-F}$=10.1 Hz, $J_{4''-2''}$=1.8 Hz, H4"), 8.67 (1H, d, $J_{2''-4''}$=1.8 Hz, H2"), 11.66 (1H, s, indolic H); $^{13}$C NMR (DMSO, 75.5 MHz): δ (ppm): 55.6 (5'-methoxy), 102.0 (C4'), 108.2 (C2), 109.7 (1C, d, $^2J_{C-F}$=37 Hz, C5"), 110.0 (C3'), 112.4 (C6'), 113.2 (C7'), 118.0 (C1), 124.0 (C3a'), 127.7 (C2'), 129.5 (1C, d, $^4J_{C-F}$=4 Hz, C3"), 130.7 (C3), 132.3 (C7a'), 140.7 (1C, d, $^3J_{C-F}$=8 Hz, C4"), 148.2 (1C, d, $^3J_{C-F}$=15 Hz, C2"), 154.6 (C5'), 162.6 (1C, d, $^1J_{C-F}$=237 Hz, C6"); ESI: 294.1 ([M+H]$^+$), 316.1 ([M+Na]$^+$), 348.1 ([M+Na+MeOH]$^+$); HRESI-MS: m/z 294.1052 (calcd for $C_{17}H_{13}N_3OF$, 294.1043).

EXAMPLE 29

(Z)-2-(5-hydroxy-1H-indol-3-yl)-3-pyridin-3-yl-acrylonitrile

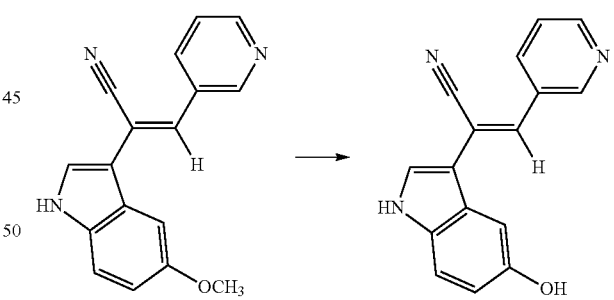

To a mixture of (Z)-2-(5-methoxy-1H-indol-3-yl)-3-pyridin-3-yl-acrylonitrile (175 mg, 0.6 mmol, 1.0 eq.) in anhydrous dichloromethane (2 mL) cooled to −78° C. (dry ice/ethanol bath) was added, under an argon atmosphere, a 1M boron tribromide solution in dichloromethane (2 mL, 2.0 mmol, 3.2 eq.). The reaction mixture was stirred at ambient temperature for 18 hours ant then quenched with ethanol. The solvent was removed under reduced pressure and the residue purified by silica gel flash-column chromatography (eluent: CH$_2$Cl$_2$/MeOH, 95:5 to 93:7) to afford the compound (29) as a yellow powder (150 mg, 91%). TLC: Rf=0.29 (CH$_2$Cl$_2$ 94/MeOH 6); Mp 258° C.; IR $v_{max}$ (cm$^{-1}$): 2218 ($v_{CN}$), 3302 ($v_{N-H}$); $^1$H NMR (DMSO, 300 MHz): δ (ppm): 6.76 (1H, dd, J$_{6'-7'}$=8.8 Hz, J$_{6'-4'}$=2.3 Hz, H6'), 7.30 (1H, d, J$_{7'-6'}$=8.8 Hz, H7'), 7.37 (1H, d, J$_{4'-6'}$=2.3 Hz, H4'), 7.52 (1H, dd, J$_{5''-4''}$=8.0 Hz, J$_{5''-6''}$=4.8 Hz, H5''), 7.64 (1H, s, H3), 7.73 (1H, s, H2'), 8.30 (1H, d, J$_{4''-5''}$=8.0 Hz, H4''), 8.57 (1H, dd, J$_{6''-5''}$=4.7 Hz, J$_{6''-4''}$=1.5 Hz, H6''), 8.94 (1H, d, J$_{2''-4''}$=2.2 Hz, H2''), 9.00 (1H, s, hydroxy H), 11.53 (1H, s, indolic H); $^{13}$C NMR (DMSO, 75.5 MHz): δ (ppm): 103.7 (C4'), 108.3 (C2), 109.7 (C3'), 112.8 (C6'), 112.9 (C7'), 118.0 (C1), 123.7 (C5''), 124.4 (C3a'), 127.2 (C2'), 130.9 (C3''), 131.5 (C3 and C7a'), 134.4 (C4''), 149.4 (C6''), 149.7 (C2''), 152.1 (C5'); ES-MS m/z 262.1 [M+H]$^+$; HRES-MS m/z 262.0985 (calcd for C$_{16}$H$_{12}$N$_3$O, 262.0980).

EXAMPLE 30

(Z)-3-[2-cyano-2-(5-methoxy-1H-indol-3-yl)-vinyl]-benzonitrile

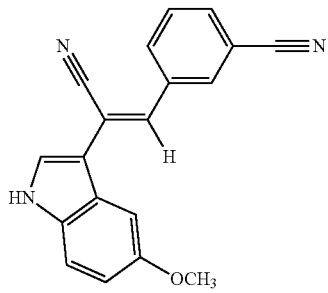 [SMILES: COc1ccc2[nH]cc(/C(C#N)=C/c3cccc(C#N)c3)c2c1]

To a solution of sodium ethanolate [prepared from sodium (30 mg, 1.3 mmol, 1.2 eq.) and anhydrous ethanol (8 mL)] were added, under an argon atmosphere, (5-methoxy-1H-indol-3-yl)-acetonitrile (200 mg, 1.1 mmol, 1.0 eq.) and, after 10 minutes stirring, 3-formyl-benzonitrile (200 mg, 1.5 mmol, 1.4 eq.). The reaction apparatus was protected from light and the mixture stirred at room temperature for 3 days. The solvent was removed under reduced pressure, and the crude purified by silica gel flash-column chromatography (eluent: heptane/CH$_2$Cl$_2$, 50:50 à 20:80). The residue was triturated with ethanol and diethyl ether to the compound (30) as a yellow powder (110 mg, 34%). mp: 149° C.; IR $v_{max}$ (cm$^{-1}$): 2227 ($v_{CN}$), 3338 ($v_{N-H}$); $^1$H NMR (DMSO, 500 MHz) δ (ppm): 3.84 (3H, s, 5'-methoxy), 6.90 (1H, m, H6'), 7.41 (1H, m, H7'), 7.49 (1H, s, H4'), 7.73 (1H, m, H5''), 7.76 (1H, s, H3), 7.79 (1H, s, H2'), 7.88 (1H, m, H6''), 8.24 (1H, m, H''), 8.28 (1H, m, H''), 11.70 (1H, s, indolic H); $^{13}$C NMR (DMSO, 75.5 MHz) δ (ppm): 55.8 (5'-methoxy), 102.2 (C4'), 108.6 and 110.3 (C2 and C3'), 112.0 (C3''), 112.6 (C6'), 113.3 (C7'), 118.0 and 118.6 (C1 and nitrile C), 124.1 (C3a'), 128.1 (C2'), 130.1 (C5''), 132.3 (C6''), 132.4 and 132.5 (C2'', C5'' and C7a'), 133.1 (C3), 136.2 (C1''), 154.8 (C5'); ESI-MS: m/z 322.1 ([M-Na]$^+$); HRESI-MS: m/z 322.0946 (calcd for C$_{19}$H$_{13}$N$_3$ONa, 322.0956).

EXAMPLE 31

(Z)-2-(5-methoxy-1H-indol-3-yl)-3-(4-methyl-pyridin-3-yl)-acrylonitrile

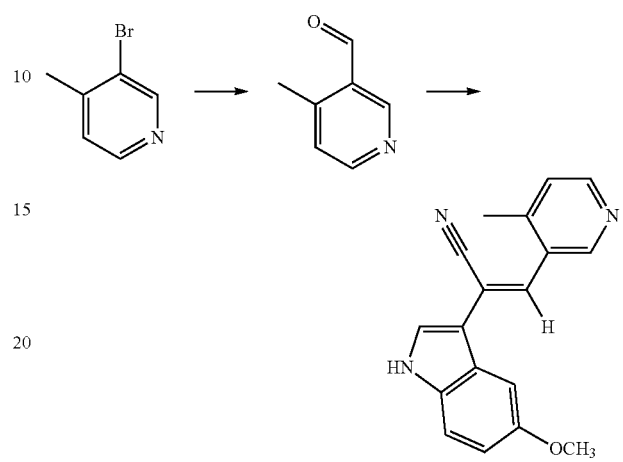

1) Preparation of 4-methyl-pyridine-3-carbaldehyde

A solution of 3-bromo-4-methyl-pyridine (2 g, 11.6 mmol, 1.0 eq.) in anhydrous THF (100 mL) was placed under an argon atmosphere in a three-necked round bottom flask equipped with a low-temperature thermometer. The mixture was cooled to −100° C. in a EtOH/N$_2$(1) bath. To the solution of 3-bromo-4-methyl-pyridine was added a solution of n-BuLi in hexane (7.3 mL, 1.6 M, 11.6 mmol, 1.0 eq.). The resulting mixture was stirred for 10 minutes at 100° C. and the organolithium that formed was trapped with a solution of ethyl formate (0.94 mL, 11.6 mmol, 1.0 eq.) in THF (4 mL). The reaction was stirred again for 30 minutes at 100° C. and quenched with a solution of hydrochloric acid in ether (6 mL, 2M). Then, the cold bath was removed and the mixture stirred at room temperature for 30 minutes. The solution was concentrated under reduced pressure and then, treated with water and saturated aqueous sodium carbonate. The mixture was extracted with dichloromethane, and then the organic layer was dried over MgSO$_4$ and evaporated under reduced pressure to afford 4-methyl-pyridine-3-carbaldehyde as a beige oil (1.3 g, 93%).

2) Preparation of (Z)-2-(5-methoxy-1H-indol-3-yl)-3-(4-methyl-pyridin-3-yl)-acrylonitrile To a suspension of NaH (1.7 g, 72.0 mmol, 6.0 eq.) and (5-methoxy-1H-indol-3-yl)-acetonitrile (2.2 g, 12.0 mmol, 1.0 eq.) in anhydrous DMF (300 mL) and diethyl ether (100 mL) was added, under an argon atmosphere, a solution of 4-methyl-pyridine-3-carbaldehyde (2.8 g, 24.0 mmol, 2.0 eq.) in diethyl ether (50 mL). The reaction apparatus was protected from light and the mixture was stirred at ambient temperature for 3 days, and then treated with an aqueous bicarbonate solution. The mixture was extracted with ethyl acetate and the organic layer was washed with water and brine, and then dried over MgSO$_4$. The solvent was removed under reduced pressure and the residue purified by silica gel flash-column chromatography (eluent: CH$_2$Cl$_2$/EtOH, 99:1 to 97:3). The product impure was triturated with dichloromethane and diethyl ether to afford the compound (31) as a yellow powder (1.5 g, 43%). TLC: Rf=0.28 (CH$_2$Cl$_2$ 96/MeOH 4); mp: 213° C.; IR ν$_{max}$ (cm$^{-1}$): 2213 (ν$_{CN}$); $^1$H NMR (DMSO, 500 MHz) δ (ppm): 2.43 (3H, s, methyl), 3.82 (3H, s, 5'-methoxy), 6.90 (1H, d, J$_{6'-7'}$=8.9 Hz, H6'), 7.37 (1H, m, H5"), 7.41 (1H, d, J$_{7'-6'}$=8.9 Hz, H7'), 7.45 (1H, s, H4'), 7.78 (2H, s, H3 and H2'), 7.91 (1H, s, H4"), 8.48 (1H, m, H6"), 8.84 (1H, s, H2"), 11.65 (1H, s, indolic H); $^{13}$C NMR (DMSO, 75.5 MHz) δ (ppm): 18.9 (C methyl), 55.4 (5'-methoxy), 101.4 (C4'), 109.9 (C2 and C3'), 112.5 (C6'), 113.2 (C7'), 117.8 (C1), 124.0 (C3a'), 125.0 (C5"), 127.6 (C2'), 131.1 (C3"), 131.6 (C3), 132.1 (C7a'), 145.9 (C4"), 147.8 (C2"), 149.3 (C6"), 154.5 (C5'); ESI-MS: m/z 290.1 ([M+H]$^+$); HRESI-MS: m/z 290.12812 (calcd for C$_{18}$H$_{16}$N$_3$O, 290.1293).

EXAMPLE 32

(Z)-3-[2-cyano-2-(5-methoxy-1H-indol-3-yl)-vinyl]-benzamide

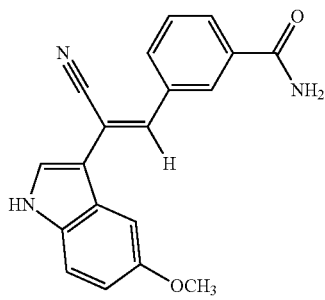 [SMILES: COc1ccc2[nH]cc(/C(C#N)=C/c3cccc(C(N)=O)c3)c2c1]

To a solution of sodium isopropanolate [prepared from sodium (30 mg, 1.3 mmol, 1.2 eq.) and isopropanol (8 mL)] were added, under an argon atmosphere, (5-methoxy-1H-indol-3-yl)-acetonitrile (200 mg, 1.1 mmol, 1.0 eq.) and, after 10 minutes stirring, 3-formyl-benzonitrile (200 mg, 1.5 mmol, 1.4 eq.). The reaction apparatus was protected from light and the mixture stirred heated at reflux for 4 hours. The reaction was allowed to cool to room temperature and then, the solvent was removed under reduced pressure, and the crude purified by silica gel flash-column chromatography (eluent: CH$_2$Cl$_2$/MeOH, 100:0 à 97:3). The residue was triturated with ethanol and diethyl ether to the compound (32) as a yellow powder (80 mg, 24%). TLC: Rf=0.34 (CH$_2$Cl$_2$ 96/MeOH 4); mp: 234° C.; IR ν$_{max}$ (cm$^{-1}$): 1651 (ν$_{C=O}$), 2215 (ν$_{CN}$), 3172 (ν$_{N-H\ amide}$), 3326 (ν$_{N-H\ indole}$); $^1$H NMR (DMSO, 300 MHz) δ (ppm): 3.89 (3H, s, 5'-methoxy), 6.97 (1H, m, H6'), 7.48 (2H, s, H7' and amide H), 7.53 (1H, s, H4'), 7.65 (1H, m, H5"), 7.83 (2H, s, H3 and H2'), 7.95 (1H, m, H4"), 8.12 (2H, m, H6" and amide H), 8.39 (1H, m, H2"), 11.68 (1H, s, indolic H); $^{13}$C NMR (DMSO, 75.5 MHz) δ (ppm): 55.6 (5'-methoxy), 101.8 (C4'), 107.0 and 110.3 (C2 and C3'), 112.3 (C6'), 113.2 (C7'), 118.3 (C1), 124.1 (C3a'), 127.3 (C2'), 127.9 (C4"), 128.3 (C2"), 128.7 (C5"), 130.5 (C6"), 132.3 (C7a'), 134.9 (C1" and C3"), 135.5 (C3), 154.5 (C5'), 167.7 (amide C); ESI-MS: m/z 340.1 ([M+Na]$^+$), 316.1 ([M−H]$^-$); HRESI-MS: m/z 340.1067 (calcd for C$_{19}$H$_{15}$N$_3$O$_2$Na), m/z 316.1117 (calcd for C$_{19}$H$_{14}$N$_3$O$_2$, 316.1086).

EXAMPLE 33

(Z)-3-[2-cyano-2-(5-methoxy-1H-indol-3-yl)-vinyl]-1-methylpyridinium iodide

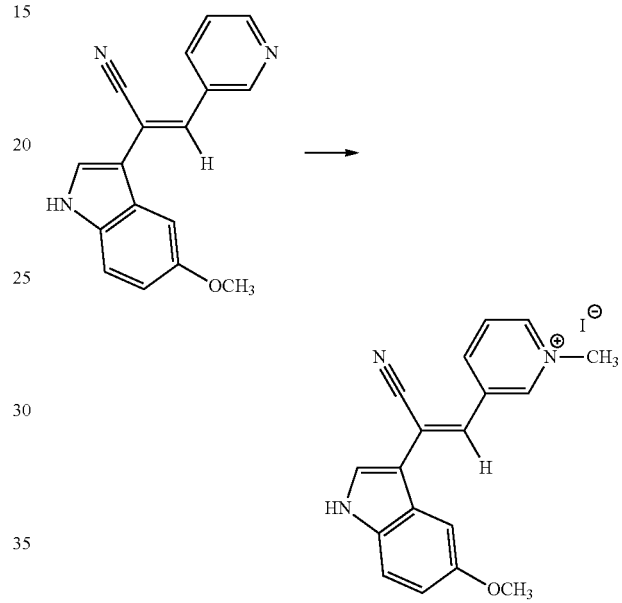

To a solution of (Z)-2-(5-methoxy-1H-indol-3-yl)-3-pyridin-3-yl-acrylonitrile (300 mg, 1.1 mmol, 1.0 eq.) in methanol (10 mL) was added, under an argon atmosphere, methyl iodide (1.4 mL, 21.8 mmol, 20.0 eq.). The reaction mixture was heated at 40° C. A second volume of methyl iodide (1.0 mL, 16.1 mmol, 15.0 eq.) was added after stirring for 3 hours. The reaction was pursued for 3 hours (6 hours overall) at 40° C. and then, allowed to cool to room temperature. The precipitate was filtered and washed with methanol and diethyl ether to afford the compound (33) as a yellow powder (430 mg, 94%). IR ν$_{max}$ (cm$^{-1}$): 2220 (ν$_{CN}$); $^1$H NMR (DMSO, 300 MHz) δ (ppm): 3.85 (3H, s, 5'-methoxy), 4.40 (3H, s, methyl), 6.96 (1H, dd, J$_{6'-7'}$=8.9 Hz, J$_{6'-4'}$=2.3 Hz, H6'), 7.45 (1H, d, J$_{7'-6'}$=8.9 Hz, H7'), 7.53 (1H, d, J$_{4'-6'}$=2.3 Hz, H4'), 7.78 (1H, s, H3), 7.91 (1H, m, H2'), 8.23 (1H, dd, J$_{5''-4''}$=8.1 Hz, J$_{5''-6''}$=6.2 Hz, H5"), 8.95 (1H, d, J$_{6''-5''}$=6.2 Hz, H6"), 9.01 (1H, d, J$_{4''-5''}$=8.1 Hz, H4"), 8.98 (1H, s, H2"), 11.88 (1H, s, indolic H); $^{13}$C NMR (DMSO, 75.5 MHz) δ (ppm): 48.3 (methyl), 55.8 (5'-methoxy), 102.7 (C4'), 110.0 (C3'), 112.4 (C6'), 112.5 (C2, 113.5 (C7'), 117.0 (C1), 123.8 (C3a'), 126.0 (C3), 127.5 (C5"), 129.8 (C2'), 132.5 (C7a'), 134.9 (C3"), 141.8 (C4"), 144.1 (C6"), 145.6 (C2"), 155.0 (C5'); ESI-MS: m/z 290.1 ([M−I$^-$]$^+$); HRESI-MS: m/z 290.1280 (calcd for C$_{18}$H$_{16}$N$_3$O, 290.1293).

EXAMPLE 34

(Z)-2-(2-propyl-6H-oxazolo[4,5-e]indol-8-yl)-3-(pyridin-3-yl)acrylonitrile

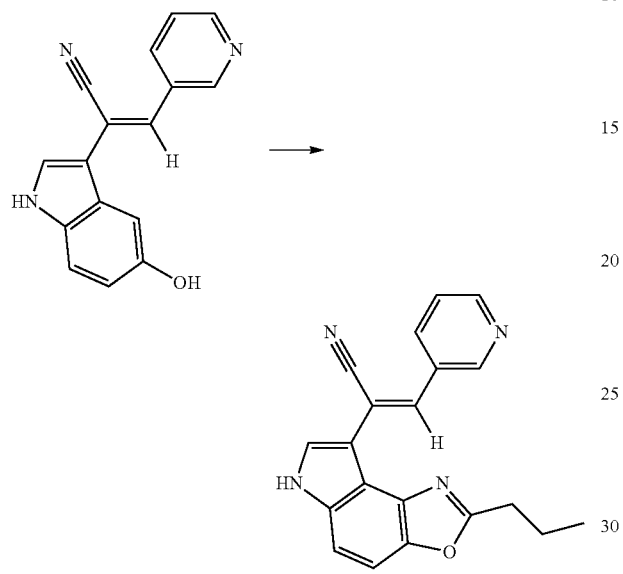

To a solution of (Z)-2-(5-hydroxy-1H-indol-3-yl)-3-pyridin-3-yl-acrylonitrile (50 mg, 0.19 mmol, 1.0 eq.) in anhydrous THF (5 mL) were added, under an argon atmosphere, n-butylamine (38 µL, 0.38 mmol, 2.0 eq.) and then, activated manganese oxide $MnO_2$ (166 mg, 1.91 mmol, 10.0 eq.). The reaction apparatus was stirred at at room temperature for 15 hours. The mixture was filtered through celite, then the solvent was removed under reduced pressure, and the residue purified by silica gel flash-column chromatography (eluent: $CH_2Cl_2$/EtOH, 96/4) to afford the compound (34) as a brown powder (35 mg, 56%). TLC: Rf=0.30 ($CH_2Cl_2$/EtOH, 96/4); IR $v_{max}$ (cm$^{-1}$): 2215 ($v_{CN}$); $^1$H NMR (DMSO, 500 MHz) δ (ppm): 1.05 (3H, t, $J_{11'-10'}$=7.3 Hz, 3H11'), 1.92 (2H, s, $J_{10'-9'}$=$J_{10'-11'}$=7.3 Hz, 2H10'), 3.01 (2H, d, $J_{9'-10'}$=7.3 Hz, 2H9'), 7.50 (1H, d, $J_{5'-4'}$=8.9 Hz, H5'), 7.56 (1H, m, H5"), 7.58 (1H, d, $J_{4'-5'}$=8.9 Hz, H4'), 7.88 (1H, s, H7'), 8.34 (1H, d, $J_{4''-5''}$=7.9 Hz, H4"), 8.60 (1H, dd, $J_{6''-5''}$=4.7 Hz, $J_{6''-4''}$=1.4 Hz, H6"), 8.92 (1H, d, $J_{2''-4''}$=2.1 Hz, H2"), 9.48 (1H, s, H3), 12.08 (1H, s, indolic H); $^{13}$C NMR (DMSO, 75.5 MHz) δ ppm): 13.5 (C11'), 19.6 (C10'), 29.7 (C9'), 106.1 (C4'), 107.5 (C2), 109.7 (C5'), 112.1 (C8'), 114.0 (C8a'), 118.0 (C1), 124.0 (C5"), 128.0 (C7'), 131.2 (C6a'), 132.5 (C8b'), 134.1 (C3 and C4"), 135.2 (C3"), 145.9 (C3a'), 149.6 (C2" and C6"), 164.7 (C2'); ESI-MS: m/z 329.1 ([M+H]$^+$), 351.1 ([M+Na]$^+$); HRESI-MS: m/z 329.1409 (calcd for $C_{20}H_{17}N_4O^+$, 329.1402).

EXAMPLE 35

(Z)-2-(5-methoxy-2-methyl-1H-indol-3-yl)-3-pyridin-3-yl-acrylonitrile

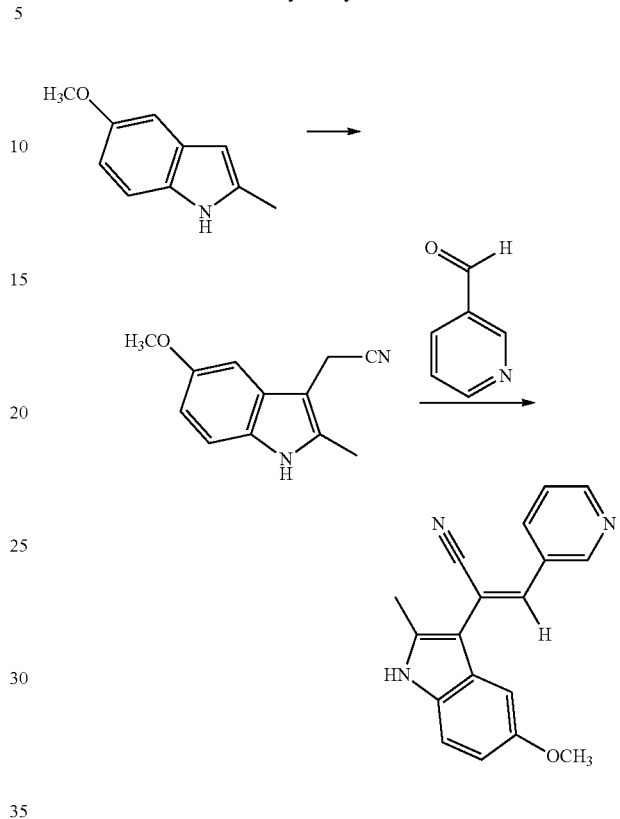

1) Preparation of (5-methoxy-2-methyl-1H-indol-3-yl)-acetonitrile

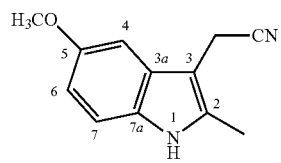

To a solution of 5-methoxy-2-methylindole (1.0 g, 6.2 mmol, 1.0 eq.) in a mixture of acetic acid (2 mL) and water (1 mL) were added, at 0° C., formaldehyde (906 µL, 37% in $H_2O$, 11.2 mmol, 1.8 eq) and dimethylamine (1.54 mL, 40% in $H_2O$, 13.6 mmol, 2.2 eq). The mixture was stirred at room temperature for 2 hours and then, quenched with ice and 5 M aqueous sodium hydroxide. The mixture was extracted with dichloromethane and then, the organic layer was dried over $MgSO_4$ and partially evaporated. To the solution gramine in dichloromethane (20 mL) were added, under an argon atmosphere, anhydrous toluene (40 mL) and methyl iodide (772 µL, 12.4 mmol, 2.0 eq.). The mixture was stirred at room temperature for 12 hours and then, concentrated under reduced pressure. To the residue taken up in anhydrous THF (60 mL) were added, under an argon atmosphere, TMSCN (1.17 mL, 9.3 mmol, 1.5 eq.) and TBAF (18.6 mL, 1M, 18.6 mmol, 3.0 eq.). The mixture was stirred at room temperature for 4 hours and then, concentrated. The crude was taken up in ethyl acetate and the organic layer was washed with a saturated aqueous bicarbonate solution and then dried over MgSO₄. The solvent was removed and the residue purified by silica gel pad filtration (eluent: EtOAc) to afford (5-methoxy-2-methyl-1H-indol-3-yl)-acetonitrile as a yellow solid (0.55 g, 44%).

2) Preparation of (Z)-2-(5-methoxy-2-methyl-1H-indol-3-yl)-3-pyridin-3-yl-acrylonitrile To a solution of sodium methanolate (162 mg, 3.0 mmol, 2.0 eq.) in anhydrous ethanol (20 mL) were added, under an argon atmosphere, (5-methoxy-2-methyl-1H-indol-3-yl)-acetonitrile (300 mg, 1.5 mmol, 1.0 eq.) and, after 30 minutes stirring, pyridine-3-carbaldehyde (352 µL, 3.8 mmol, 2.5 eq.). The reaction apparatus was protected from light and the mixture heated at 50° C. for 12 hours. The reaction was allowed to cool to room temperature and then, the solvent was removed under reduced pressure and the crude taken up in ethyl acetate. The organic layer was washed with water and brine, dried over MgSO₄ and then, evaporated. The residue was purified by silica gel flash-column chromatography (eluent: heptane/EtOAc, 40/60) to afford, after trituration with diethyl ether and dichloromethane, the compound (35) as a yellow solid (250 mg, 58%). IR □$_{max}$ (cm⁻¹): 2212 ($v_{CN}$); ¹H NMR (DMSO, 300 MHz) δ (ppm): 2.54 (3H, s, 2'-methyl), 3.77 (3H, s, 5'-methoxy), 6.78 (1H, dd, $J_{6'-7'}$=8.9 Hz, $J_{6'-4'}$=2.4 Hz, H6'), 7.18 (1H, d, $J_{4'-6'}$=2.4 Hz, H4'), 7.27 (1H, d, $J_{7'-6'}$=8.9 Hz, H7'), 7.50 (1H, s, H3), 7.55 (1H, dd, $J_{5''-4''}$=8.1 Hz, $J_{5''-6''}$=4.8 Hz, H5''), 7.74 (1H, s, H3), 8.35 (1H, d, $J_{4''-5''}$=8.1 Hz, H4''), 8.61 (1H, d, $J_{6''-5''}$=4.8 Hz, H6''), 8.97 (1H, s, H2''), 11.45 (1H, s, indolic H); ¹³C NMR (DMSO, 75.5 MHz) δ (ppm): 12.6 (2'-methyl), 55.3 (5'-methoxy), 100.4 (C4'), 106.1 (C2), 106.9 (C3'), 110.9 (C6'), 111.9 (C7'), 118.0 (C1), 123.7 (C5''), 126.2 (C3a'), 129.9 (C2'), 130.5 (C3''), 134.6 (C3), 136.3 (C7a'), 137.6 (C4''), 149.8 (C6''), 150.0 (C2''), 154.1 (C5'); ESI-MS: m/z 290.1 ([M+H]⁺), 312.1 ([M+Na]⁺); HRESI-MS: m/z 290.1299 (calcd for C₁₈H₁₆N₃O⁺, 290.1293).

EXAMPLE 36

(Z)-3-(pyridin-3-yl)-2-(1H-pyrrolo[2,3-b]pyridin-3-yl)-acrylonitrile

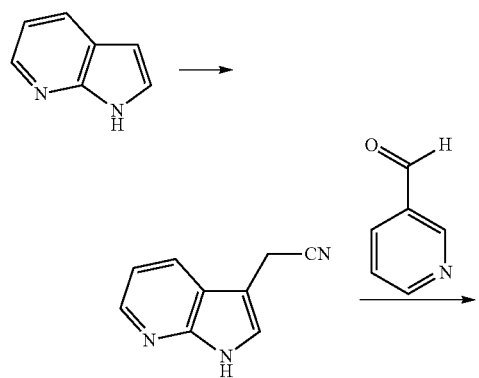

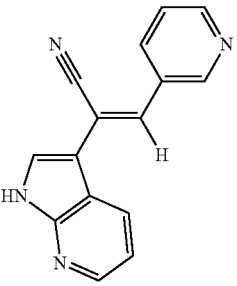

1) Preparation of 2-(1H-pyrrolo[2,3-b]pyridin-3-yl)-acetonitrile

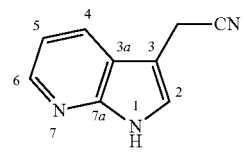

To a solution of 1H-pyrrolo[2,3-b]pyridine (1.5 g, 12.7 mmol, 1.0 eq.) and paraformaldehyde (0.46 g, 15.2 mmol, 1.2 eq.) in isopropanol (20 mL) was added dimethylamine hydrochloride (1.24 g, 15.2 mmol, 1.2 eq). The mixture was stirred at reflux temperature for 20 minutes and then, quenched with ice and 5 M aqueous sodium hydroxide after cooling to room temperature. The mixture was extracted with ethyl acetate and the organic layer was dried over MgSO₄ and evaporated under reduced pressure. The gramine residue was taken up in a mixture of anhydrous dichloromethane (40 mL) and toluene (80 mL) and then, methyl iodide (1.26 mL, 20.3 mmol, 1.6 eq.) was added under an argon atmosphere. The mixture was stirred at room temperature for 12 hours and concentrated. To the residue taken up in anhydrous THF (120 mL) were added, under an argon atmosphere, TMSCN (2.39 mL, 19.1 mmol, 1.5 eq.) and TBAF (38.1 mL, 1M, 38.1 mmol, 3.0 eq.). The mixture was stirred at room temperature for 4 hours and then, concentrated under reduced pressure. The crude was taken up in ethyl acetate and the organic layer was washed with a saturated aqueous sodium bicarbonate solution and then, dried over MgSO₄. The solvent was removed under reduced pressure, and the residue purified by silica gel flash-column chromatography (eluent: heptane/EtOAc, 50:50) to afford 2-(1H-pyrrolo[2,3-b]pyridin-3-yl)-acetonitrile as a white solid (0.56 g, 28%).

2) Preparation of (Z)-3-(pyridin-3-yl)-2-(1H-pyrrolo[2,3-b]pyridin-3-yl)-acrylonitrile To a solution of sodium methanolate (124 mg, 2.3 mmol, 2.0 eq.) in anhydrous ethanol (20 mL) were added, under an argon atmosphere, 2-(1H-pyrrolo[2,3-b]pyridin-3-yl)-acetonitrile (180 mg, 1.2 mmol, 1.0 eq.) and, after 30 minutes stirring, pyridine-3-carbaldehyde (270 µL, 2.9 mmol, 2.5 eq.). The reaction apparatus was protected from light and the mixture heated at 50° C. for 15 hours. The reaction was allowed to cool to room temperature and the solvent was removed under reduced pressure. The crude was taken up in a mixture of water and ethanol, and then filtered to afford the compound (36) as a yellow solid (230 mg, 81%). IR □$_{max}$ (cm$^{-1}$): 2218 ($v_{CN}$); $^1$H NMR (DMSO, 300 MHz) δ (ppm): 7.66 (1H, dd, J$_{5'-4'}$=8.1 Hz, J$_{5'-6'}$=4.8 Hz, H5'), 7.96 (1H, dd, J$_{5''-4''}$=8.1 Hz, J$_{5''-6''}$=4.8 Hz, H5''), 8.28 (1H, s, H3), 8.37 (1H, s, H2'), 8.76 (2H, m, H6' and H4''), 8.95 (1H, d, J$_{4'-5'}$=8.1 Hz, H4'), 8.60 (1H, d, J$_{6''-5''}$=4.7 Hz, H6''), 9.02 (1H, dd, J$_{6''-5''}$=4.8 Hz, J$_{6''-4''}$=1.5 Hz, H6''), 9.41 (1H, d, J$_{2''-4''}$=2.1 Hz, H2''), 12.76 (1H, s, pyrrolic H); $^{13}$C NMR (DMSO, 75.5 MHz) δ (ppm): 108.3 (C2), 110.2 (C3'), 116.9 (C3a'), 117.7 (C5'), 118.5 (C1), 124.6 (C5''), 128.1 (C2'), 129.1 (C4'), 131.4 (C3''), 134.5 (C3), 135.5 (C4''), 145.0 (C6'), 150.0 (C7a'), 150.8 (C6''), 150.9 (C2''); ESI-MS: m/z 247.1 ([M+H]$^+$); HRESI-MS: m/z 247.0984 (calcd for C$_{15}$H$_{11}$N$_4^+$, 247.0984).

EXAMPLE 37

(Z)-2-(5-bromo-1H-indol-3-yl)-3-pyridin-3-yl-acrylonitrile

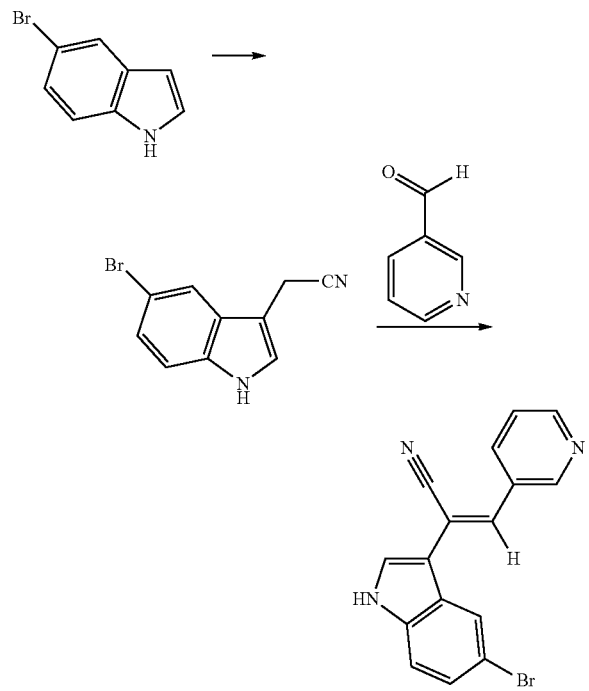

1) Preparation of (5-bromo-1H-indol-3-yl)-acetonitrile

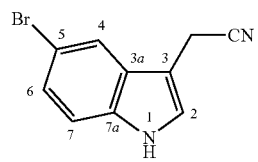

To a solution of 5-bromoindole (3.0 g, 15.3 mmol, 1.0 eq.) in a mixture of acetic acid (8.0 mL) and water (2.0 mL) were added, at 0° C., formaldehyde (1.5 mL, 37% in H$_2$O, 18.4 mmol, 1.2 eq) and dimethylamine (3.0 mL, 40% in H$_2$O, 27.5 mmol, 1.8 eq). The mixture was stirred at room temperature for 4 hours and then, quenched with ice and 5 M aqueous sodium hydroxide. The mixture was extracted with dichloromethane and then, the organic layer was dried over MgSO$_4$ and partially evaporated. To the solution gramine in dichloromethane (50 mL) were added, under an argon atmosphere, anhydrous toluene (100 mL) and methyl iodide (1.49 mL, 24.5 mmol, 1.6 eq.). The mixture was stirred at room temperature for 36 hours and then, the precipitate was filtered and washed with diethyl ether. To the resulting powder were added water (100 mL) and potassium cyanide (2.9 g, 44.5 mmol, 3.0 eq.). The mixture was stirred at reflux temperature for 1 hour and quenched with a saturated aqueous sodium carbonate solution, after cooling to room temperature. The crude product was extracted with ethyl acetate and then, the organic layer was and dried over MgSO$_4$, filtered through a silica gel pad and concentrated under reduced pressure to afford (5-bromo-1H-indol-3-yl)-acetonitrile as a beige solid (2.8 g, 78%).

2) Preparation of (Z)-2-(5-bromo-1H-indol-3-yl)-3-pyridin-3-yl-acrylonitrile

To a solution of sodium methanolate (793 mg, 14.7 mmol, 1.5 eq.) in anhydrous ethanol (200 mL) were added, under an argon atmosphere, (5-bromo-1H-indol-3-yl)-acetonitrile (2.3 g, 9.8 mmol, 1.0 eq.) and, after 30 minutes stirring, pyridine-3-carbaldehyde (1.84 mL, 19.6 mmol, 2.0 eq.). The reaction apparatus was protected from light and the mixture heated at 50° C. for 3 hours. The reaction was allowed to cool to room temperature and then, the solvent was removed under reduced pressure and the crude taken up in ethyl acetate. The organic layer was washed with water and brine, dried over MgSO$_4$ and filtered through a silica gel pad. The solvent was evaporated and the residue was triturated with diethyl ether to afford the compound (37) as a yellow powder (2.2 g, 70%). mp: 232° C.; IR $v_{max}$ (cm$^{-1}$): 2218 ($v_{CN}$); $^1$H NMR (DMSO, 300 MHz) δ (ppm): 7.37 (1H, d, J$_{6'-7'}$=8.9 Hz, J$_{6'-4'}$=2.4 Hz, H6'), 7.48 (1H, d, J$_{7'-6'}$=8.9 Hz, H7'), 7.54 (1H, dd, J$_{5''-4''}$=7.9 Hz, J$_{5''-6''}$=4.9 Hz, H5''), 7.84 (1H, s, H3), 7.91 (1H, s, H2'), 8.25 (1H, d, J$_{4'-6'}$=2.4 Hz, H4'), 8.33 (1H, d, J$_{4''-5''}$=7.9 Hz, H4''), 8.60 (1H, dd, J$_{6''-5''}$=4.9 Hz, J$_{6''-4''}$=1.5 Hz, H6''), 9.00 (1H, d, J$_{2''-4''}$=2.1 Hz, H2''), 11.95 (1H, s, indolic H); $^{13}$C NMR (DMSO, 75.5 MHz) δ (ppm): 107.8 (C2), 110.5 (C3'), 113.9 (C5'), 115.0 (C7'), 118.4 (C1), 122.1 (C4'), 124.1 (C5''), 125.7 (C6' and C3a'), 128.9 (C2'), 131.2 (C3''), 134.3 (C3), 135.3 (C4''), 136.4 (C7a'), 150.2 (C6''), 150.5 (C2''); ESI-MS: m/z 324.1 ([M+H]$^+$); HRESI-MS: m/z 324.0141 (calcd for C$_{16}$H$_{11}^{79}$BrN$_3^+$, 324.0136).

EXAMPLE 38

(Z)-3-(pyridin-3-yl)-2-(5-(3,4,5-trimethoxyphenyl)-1H-indol-3-yl)-acrylonitrile

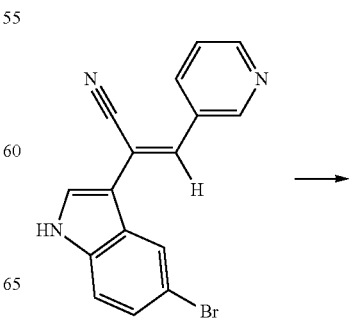

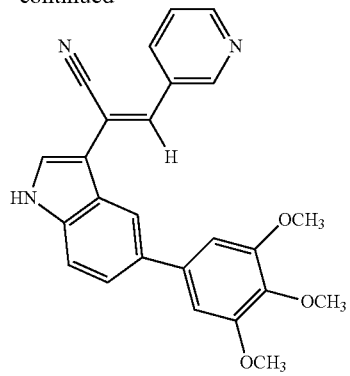

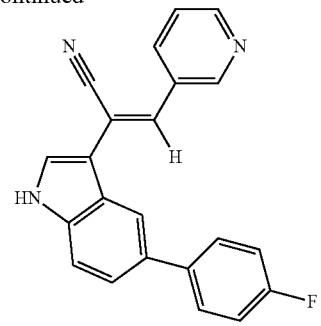

To a solution of (Z)-2-(5-bromo-1H-indol-3-yl)-3-pyridin-3-yl-acrylonitrile (180 mg, 0.56 mmol, 1.0 eq.) in anhydrous and degazed THF (6.0 mL) were added, under an argon atmosphere, $K_3PO_4$ (236 mg, 1.11 mmol, 2.0 eq.), $PdCl_2$(dppf)·$CH_2Cl_2$ (41 mg, 0.056 mmol, 0.1 eq.) and 3,4,5-trimethoxyphenylboronic acid (235 mg, 1.11 mmol, 2.0 eq.). The reaction apparatus was protected from light and the mixture was heated at 50° C. for 16 hours, and then, quenched with a saturated aqueous ammonium chloride solution, after cooling to room temperature. The mixture was extracted with ethyl acetate and the organic layer was washed with water, dried over $MgSO_4$, and then, evaporated under reduced pressure. The residue was purified by silica gel flash-column chromatography (eluent: heptane/AcOEt, 40/60 to 30/70) to afford, after trituration with diethyl ether, the compound (38) as a yellow solid (145 mg, 63%). IR $v_{max}$ (cm$^{-1}$): 2216 ($v_{CN}$), 3307 ($v_{N-H}$); $^1$H NMR (DMSO, 500 MHz) δ (ppm): 3.70 (3H, s, 11'-methoxy), 3.88 (6H, s, 10'- and 12'-methoxy), 6.96 (2H, s, H9' and H13'), 7.55 (3H, m, H6', H7' and H5"), 7.88 (1H, m, H4'), 7.93 (1H, s, H3), 8.24 (1H, s, H2'), 8.35 (1H, d, $J_{4"-5"}$=7.9 Hz, H4"), 8.59 (1H, d, $J_{6"-5"}$=4.9 Hz, H6"), 9.01 (1H, s, H2"), 11.84 (1H, s, indolic H); $^{13}$C NMR (DMSO, 75.5 MHz) δ (ppm): 56.5 (10'- and 12'-methoxy), 60.5 (11'-methoxy), 105.3 (C9' and C13'), 108.4 (C2), 111.4 (C3'), 113.2 (C7'), 118.2 (C2'), 118.6 (C1), 122.9 (C6'), 124.1 (C5"), 124.5 (C3a'), 128.4 (C4'), 131.4 (C3"), 133.6 (C11'), 134.2 (C7a'), 135.2 (C4"), 137.2 (C3), 138.0 (C8'), 150.1 (C6"), 150.5 (C2"), 153.6 (C10' and C12'); ESI-MS: m/z 412.2 ([M+H]$^+$), 434.1 ([M+Na]$^+$); HRESI-MS: m/z 434.1481 (calcd for $C_{25}H_{21}N_3O_3Na^+$, 434.1481).

EXAMPLE 39

(Z)-2-(5-(4-fluorophenyl)-1H-indol-3-yl)-3-(pyridin-3-yl)-acrylonitrile

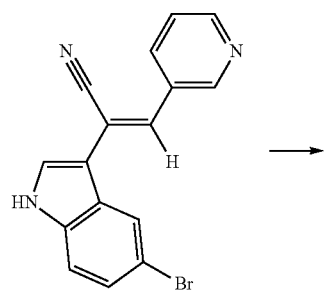

To a solution of (Z)-2-(5-bromo-1H-indol-3-yl)-3-pyridin-3-yl-acrylonitrile (180 mg, 0.56 mmol, 1.0 eq.) in anhydrous and degazed THF (6.0 mL) were added, under an argon atmosphere, $K_3PO_4$ (236 mg, 1.11 mmol, 2.0 eq.), $PdCl_2$(dppf)·$CH_2Cl_2$ (41 mg, 0.056 mmol, 0.1 eq.) and 4-fluorophenylboronic acid (155 mg, 1.11 mmol, 2.0 eq.). The reaction apparatus was protected from light and the mixture was heated at 50° C. for 16 hours, and then, quenched with a saturated aqueous ammonium chloride solution, after cooling to room temperature. The mixture was extracted with ethyl acetate and the organic layer was washed with water, dried over $MgSO_4$, and then, evaporated under reduced pressure. The residue was purified by silica gel flash-column chromatography (eluent: heptane/AcOEt, 50/50 to 30/70) to afford, after trituration with diethyl ether, the compound (39) as an orange solid (175 mg, 92%). IR $v_{max}$ (cm$^{-1}$): 2217 ($v_{CN}$); $^1$H NMR (DMSO, 500 MHz) δ (ppm): 7.29 (2H, t, $J_{10'-9'}$=$J_{12'-13'}$=$J_{10'-F}$=$J_{12'-F}$=8.5 Hz, H10' and H12'), 7.52 (1H, dm, $J_{6'-7'}$=8.9 Hz, H6'), 7.55 (1H, dd, $J_{5"-4"}$=7.9 Hz, $J_{5"-6"}$=4.9 Hz, H5"), 7.59 (1H, d, $J_{7'-6'}$=8.9 Hz, H7'), 7.78 (2H, dd, $J_{9'-10'}$=$J_{13'-12'}$=8.5 Hz et $J_{9'-F}$=$J_{13'-F}$=5.5 Hz, H9' and H13'), 7.89 (1H, m, H4'), 7.91 (1H, s, H3), 8.23 (1H, s, H2'), 8.34 (1H, d, $J_{4"-5"}$=7.9 Hz, H4"), 8.60 (1H, d, $J_{6"-5"}$=4.9 Hz, H6"), 9.01 (1H, s, H2"), 11.86 (1H, s, indolic H); $^{13}$C NMR (DMSO, 75.5 MHz) δ (ppm): 108.4 (C2), 111.4 (C3'), 113.4 (C7'), 116.0 (2C, d, $^2J_{C-F}$=21 Hz, C10' and C12'), 118.1 (C2'), 118.6 (C1), 122.6 (C6'), 124.1 (C5"), 124.7 (C3a'), 128.4 (C4'), 129.4 (2C, d, $^3J_{C-F}$=8 Hz, C9' and C13'), 131.4 (C3"), 132.9 (C7a'), 133.8 (C3), 135.2 (C4"), 137.2 (C5'), 138.4 (C8'), 150.1 (C6"), 150.5 (C2"), 162.0 (1C, d, $^1J_{C-F}$=244 Hz, C4"); ESI-MS: m/z 340.1 ([M+H]$^+$); HRESI-MS: m/z 340.1241 (calcd for $C_{22}H_{15}N_3F$, 340.1250).

EXAMPLE 40

(Z)-2-(5-amino-1H-indol-3-yl)-3-pyridin-3-yl-acrylonitrile

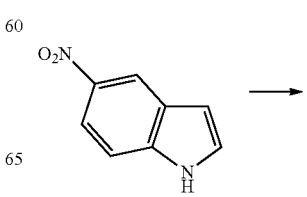

2) Preparation of (7)-2-(5-nitro-1H-indol-3-yl)-3-pyridin-3-yl-acrylonitrile

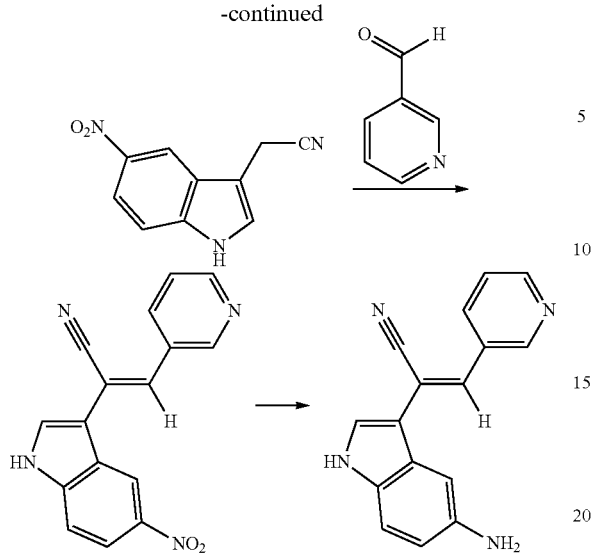

To a solution of sodium methanolate (322 mg, 6.0 mmol, 1.2 eq.) in anhydrous ethanol (60 mL) were added, under an argon atmosphere, 221 (1.0 g, 5.0 mmol, 1.0 eq.) and, after 5 minutes stirring, pyridine-3-carbaldehyde (1.12 mL, 5.0 mmol, 2.4 eq.). The reaction apparatus was protected from light and the mixture heated at 40° C. for 30 minutes, and then quenched with water. The insoluble was filtered and triturated with ethanol and diethyl ether to afford (Z)-2-(5-nitro-1H-indol-3-yl)-3-pyridin-3-yl-acrylonitrile as a yellow solid (1.2 g, 83%).

1) Preparation of (5-nitro-1H-indol-3-yl)-acetonitrile

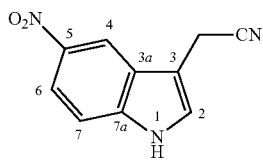 [SMILES: N#CCc1c[nH]c2ccc([N+](=O)[O-])cc12]

To a solution of 5-nitroindole (2.0 g, 12.3 mmol, 1.0 eq.) in acetic acid (8.0 mL) were added, at 0° C., formaldehyde (1.2 mL, 37% in $H_2O$, 14.8 mmol, 1.2 eq) and dimethylamine (2.5 mL, 40% in $H_2O$, 22.2 mmol, 1.8 eq). The mixture was stirred at 55° C. for 90 minutes and then, quenched with ice and 5 M aqueous sodium hydroxide after cooling to room temperature. The mixture was extracted with ethyl acetate and then, the organic layer was dried over $MgSO_4$ and evaporated. To the residue gramine taken up in a solution of ethanol (50 mL) and water (5 mL) were added potassium cyanide (1.6 g, 24.6 mmol, 2.0 eq.) and then, methyl iodide (2.0 mL, 32.0 mmol, 2.6 eq.). The mixture was stirred at room temperature for 18 hours and then, quenched with a saturated aqueous sodium carbonate solution. The mixture was extracted with ethyl acetate and then, the organic layer was and dried over $MgSO_4$, filtered through a silica gel pad and concentrated under reduced pressure to afford, after trituration with diethyl ether, (5-nitro-1H-indol-3-yl)-acetonitrile as an orange solid (1.8 g, 73%).

3) Preparation of (Z)-2-(5-amino-1H-indol-3-yl)-3-pyridin-3-yl-acrylonitrile To a mixture of (Z)-2-(5-nitro-1H-indol-3-yl)-3-pyridin-3-yl-acrylonitrile (370 mg, 1.27 mmol, 1.0 eq.) in ethanol (40 mL) were added zinc powder (667 mg, 10.2 mmol, 8.0 eq.) and then, ammonium chloride (679 mg, 12.7 mmol, 10.0 eq.). The reaction mixture was stirred at room temperature for 30 minutes and filtered through a celite pad. The filtrate was concentrated under reduced pressure and partitioned between water and ethyl acetate. The organic layer was washed with brine, dried over $MgSO_4$ and evaporated. The residue was purified by silica gel flash-column chromatography (eluent: $CH_2Cl_2$/EtOH, 96/4 to 94/6) to afford, after trituration with diethyl ether, the compound (40) as a orange solid (80 mg, 24%). IR $v_{max}$ ($cm^{-1}$): 2216 ($v_{CN}$), 3340 ($v_{N-H}$); $^1$H NMR (DMSO, 500 MHz) δ (ppm): 4.72 (2H, s, aniline H), 6.63 (1H, dd, $J_{6'-7'}$=8.9 Hz, $J_{6'-4'}$=2.4 Hz, H6'), 7.19 (1H, d, $J_{7'-6'}$=8.9 Hz, H7'), 7.22 (1H, d, $J_{4'-6'}$=2.4 Hz, H4'), 7.54 (1H, dd, $H_{5''-4''}$=7.9 Hz, $J_{5''-6''}$=4.8 Hz, H5''), 7.59 (1H, s, H3), 7.61 (1H, s, H2'), 8.29 (1H, d, $J_{4''-5''}$=7.9 Hz, H4''), 8.57 (1H, d, $J_{6''-5''}$=4.8 Hz, H6''), 8.93 (1H, s, H2''), 11.37 (1H, s, indolic H); $^{13}$C NMR (DMSO, 75.5 MHz) δ (ppm): 103.0 (C4'), 109.3 (C2), 109.9 (C3'), 113.2 (C6'), 113.4 (C7'), 118.5 (C1), 124.2 (C5''), 125.1 (C3a'), 127.1 (C2'), 130.9 (C3), 131.1 (C3''), 131.5 (C7a'), 134.7 (C4''), 143.7 (C5'), 149.8 (C6''), 150.2 (C2''); ESI-MS: m/z 261.1 ([M+H]$^+$); HRESI-MS: m/z 261.1153 (calcd for $C_{16}H_{13}N_4^+$, 261.1140).

EXAMPLE 41

(Z)-methyl 3-(1-cyano-2-(pyridin-3-yl)vinyl)-1H-indol-5-ylcarbamate

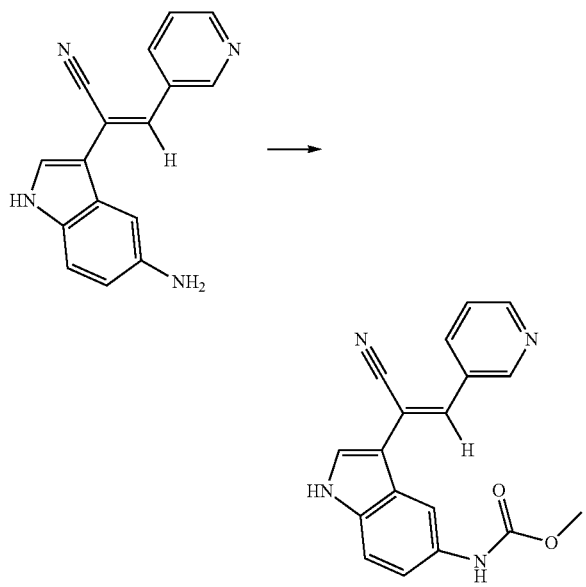

To a solution of (Z)-2-(5-amino-1H-indol-3-yl)-3-pyridin-3-yl-acrylonitrile (20 mg, 0.077 mmol, 1.0 eq.) in anhydrous THF (6 mL) were added as added, under an argon atmosphere, methyl chloroformate (6.6 µL, 0.085 mmol, 1.1 eq.) and then, triethylamine (23.4 µL, 0.17 mmol, 2.2 eq.). The reaction apparatus was protected from light and the mixture was stirred at room temperature for 8 hours, and then quenched with brine. The mixture was extracted with ethyl acetate and the organic layer was dried over MgSO$_4$. The solvent was removed under reduced pressure and the residue was purified by silica gel flash-column chromatography (eluent: CH$_2$Cl$_2$/EtOH, 93/7 to 95/5) to afford the compound (41) as a yellow solid (20 mg, 82%). IR $\nu_{max}$ (cm$^{-1}$): 1232 ($\nu_{C-N}$), 1726 ($\nu_{C=O}$), 2217 ($\nu_{CN}$), 3360 ($\nu_{N-H\ indole}$); $^1$H NMR (DMSO, 500 MHz) δ (ppm): 3.69 (3H, s, methoxy), 7.35 (1H, m, H6), 7.42 (1H, d, J$_{7-6}$=8.9 Hz, H7), 7.56 (1H, dd, J$_{5''-4''}$=7.9 Hz, J$_{5''-6''}$=4.9 Hz, H5''), 7.66 (1H, s, H2'), 7.80 (1H, s, H2), 8.13 (1H, m, H4), 8.31 (1H, d, J$_{4''-5''}$=7.9 Hz, H4''), 8.60 (1H, d, J$_{6''-5''}$=4.9 Hz, H6''), 8.93 (1H, s, H2''), 9.48 (1H, s, carbamate H), 11.70 (1H, s, indolic H); $^{13}$C NMR (DMSO, 75.5 MHz) δ (ppm): 52.0 (methoxy), 108.6 (C1'), 109.5 (C4), 110.6 (C3), 113.0 (C7), 116.3 (C6), 118.3 (nitrile C), 124.1 (C3a), 124.3 (C5''), 128.1 (C2), 131.2 (C3'), 132.8 (C2'), 133.3 (C5), 134.0 (C7a), 134.9 (C4''), 150.2 (C2'' and C6''), 154.9 (carbamate C); ESI-MS: m/z 319.1 ([M+H]$^+$), 341.1 ([M+Na]$^+$); HRESI-MS: m/z 341.1018 (calcd for C$_{18}$H$_{14}$N$_4$O$_2$Na$^+$, 341.1014).

EXAMPLE 42

(Z)-2-(1H-indol-3-yl)-3-(3-nitro-phenyl)-acrylonitrile

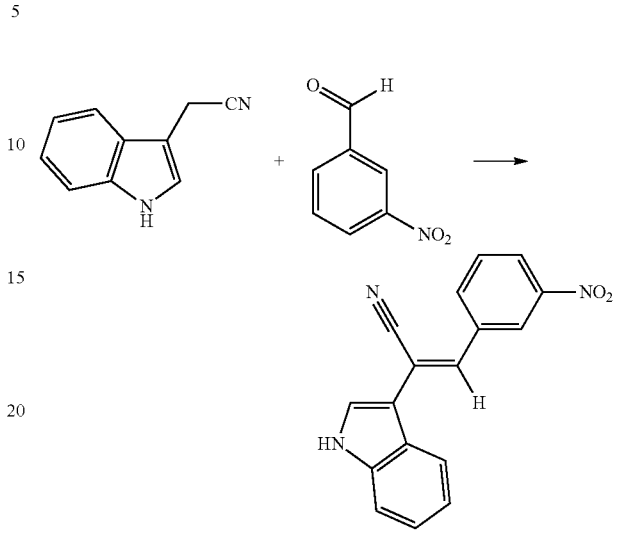

To a solution of sodium ethanolate [prepared from sodium (79 mg, 3.5 mmol, 1.8 eq.) and anhydrous ethanol (5 mL)] were added, under an argon atmosphere, (1H-indol-3-yl)-acetonitrile (300 mg, 1.9 mmol, 1.0 eq.) and, after 10 minutes stirring, 3-nitro-benzaldehyde (522 mg, 3.5 mmol, 1.8 eq.). The reaction apparatus was protected from light and the mixture stirred at room temperature for 3 days. The solvent was removed under reduced pressure, and the crude purified by silica gel flash-column chromatography (eluent: heptane/CH$_2$Cl$_2$, 20/80). The residue was triturated with dichloromethane and heptane to afford the compound (42) as a yellow powder (298 mg, 36%). TLC: Rf=0.40 (CH$_2$Cl$_2$ 100); mp: 203° C.; $^1$H NMR (DMSO, 500 MHz) δ (ppm): 7.21 (1H, t, J$_{5'-6'}$=J$_{5'-4'}$=7.9 Hz, H5'), 7.26 (1H, t, J$_{6'-5'}$=J$_{6'-7'}$=7.9 Hz, H6'), 7.52 (1H, d, J$_{7'-6'}$=7.9 Hz, H7'), 7.81 (1H, t, J$_{5''-4''}$=J$_{5''-6''}$=7.9 Hz, H5''), 7.88 (1H, s, H2'), 7.95 (1H, s, H3), 8.16 (1H, d, J$_{4'-5'}$=7.9 Hz, H4'), 8.26 (1H, d, J$_{4''-5''}$=7.9 Hz, H4''), 8.36 (1H, d, J$_{6''-5''}$=7.9 Hz, H6''), 8.80 (1H, s, H2''), 11.84 (1H, s, indolic H); $^{13}$C NMR (DMSO, 75.5 MHz) δ (ppm): 112.4 (C2), 114.4 (C3'), 116.4 (C7'), 121.8 (C1), 123.7 (C4'), 124.7 (C5'), 126.7 (C6'), 127.0 (C2''), 127.3 (C4''), 127.4 (C3a'), 131.6 (C2'), 134.2 (C5''), 137.0 (C3), 138.2 (C6''), 140.3 (C1''), 141.2 (C7a'), 152.0 (C3''); ESI-MS: m/z 288.1 ([M−H]$^-$); HRESI-MS: m/z 288.0781 (calcd for C$_{17}$H$_{10}$N$_3$O$_2^-$, 288.0773); Anal. Calcd for C$_{17}$H$_{11}$N$_3$O$_2$: C, 70.58; H, 3.83; N, 14.53; O, 11.06. Found: C, 70.44; H, 3.72; N, 14.64.

EXAMPLE 43

(Z)-2-(5-methoxy-1H-indol-3-yl)-3-(3-nitro-phenyl)-acrylonitrile

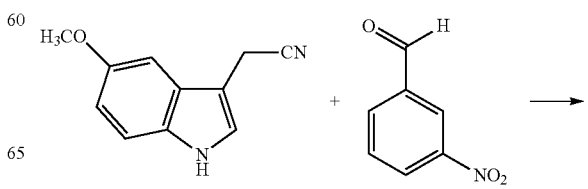

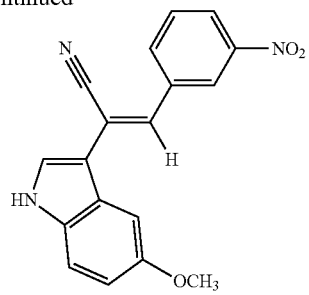

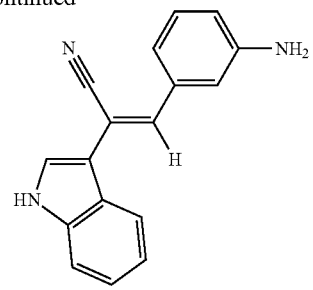

To a solution of sodium ethanolate [prepared from sodium (44 mg, 1.9 mmol, 1.8 eq.) and anhydrous ethanol (4 mL)] were added, under an argon atmosphere, (5-methoxy-1H-indol-3-yl)-acetonitrile (200 mg, 1.1 mmol, 1.0 eq.) and, after 10 minutes stirring, 3-nitrobenzaldehyde (292 mg, 1.9 mmol, 1.8 eq.). The reaction apparatus was protected from light and the mixture stirred at room temperature for 3 days. The solvent was removed under reduced pressure, and the crude purified by silica gel flash-column chromatography (eluent: heptane/CH$_2$Cl$_2$, 30/70 to 0/100). The residue was triturated with ethanol and diethyl ether to afford the compound (43) as a yellow powder (90 mg, 26%). TLC: Rf=0.40 (CH$_2$Cl$_2$ 100); mp: 188° C.; IR $v_{max}$ (cm$^{-1}$): 1342 ($v_{N-O\ sym.}$), 1517 ($v_{N-O\ asym.}$), 2222 ($v_{CN}$), 3334 ($v_{N-H}$); $^1$H NMR (DMSO, 300 MHz) δ (ppm): 3.89 (3H, s, 5'-methoxy), 6.96 (1H, dd, J$_{6'-7'}$=8.9 Hz, J$_{6'-4'}$=2.4 Hz, H6'), 7.47 (1H, d, J$_{7'-6'}$=8.9 Hz, H7'), 7.58 (1H, d, J$_{4'-6'}$=2.4 Hz, H4'), 7.84 (1H, t, J$_{5''-4''}$=J$_{5''-6''}$=8.0 Hz, H5''), 7.87 (1H, s, H2'), 7.91 (1H, s, H3), 8.29 (1H, dd, J$_{4''-5''}$=8.0 Hz, J$_{4''-2''}$=2.0 Hz, H4''), 8.37 (1H, d, J$_{6''-5''}$=8.0 Hz, H6''), 8.82 (1H, s, H2''), 11.75 (1H, s, indolic H); $^{13}$C NMR (DMSO, 75.5 MHz) δ (ppm): 55.6 (5'-methoxy), 102.2 (C4'), 108.6 and 110.1 (C2 and C3'), 112.4 (C6'), 113.2 (C7'), 117.9 (C1), 122.9 (C2''), 123.3 (C4''), 124.0 (C3a'), 128.0 (C2'), 130.2 (C5''), 132.3 (C7a'), 132.8 (C3), 134.4 (C6''), 136.5 (C1''), 148.0 (C3''), 154.6 (C5'); ESI-MS: m/z 318.0 ([M-H]$^-$); HRESI-MS: m/z 318.0875 (calcd for C$_{18}$H$_{12}$N$_3$O$_3^-$, 318.0879); Anal. Calcd for C$_{18}$H$_{13}$N$_3$O$_3$: C, 67.71; H, 4.10; N, 13.16; O, 15.03. Found: C, 67.31; H, 3.93; N, 13.28.

To a solution of (Z)-2-(1H-indol-3-yl)-3-(3-nitro-phenyl)-acrylonitrile (160 mg, 0.5 mmol, 1.0 eq.) in acetic acid (8 mL) was added zinc powder (2.0 g). The reaction apparatus was protected from light and the mixture stirred at room temperature for 40 minutes. The mixture was filtered under celite, the filtrate evaporated under reduced pressure and the residue purified by silica gel flash-column chromatography (eluent: CH$_2$Cl$_2$/MeOH, 100/0 à 96/4). The product impure was solubilized with CH$_2$Cl$_2$ and the organic layer was washed with water and saturated aqueous sodium carbonate, and then, dried over MgSO$_4$ and evaporated under reduced pressure to afford the compound (44) as a yellow powder (102 mg, 74%). TLC: Rf=0.39 (heptane/EtOAc, 40/60); mp: 138° C.; $^1$H NMR (DMSO, 300 MHz) δ (ppm): 5.25 (2H, s, aniline H), 6.64 (1H, d, J$_{4''-5''}$=7.6 Hz, H5''), 7.05 (2H, m, H2'' and H6''), 7.16 (3H, m, H5', H6' and H5''), 7.49 (1H, d, J$_{7'-6'}$=7.8 Hz, H7'), 7.57 (1H, s, H3), 7.76 (1H, s, H2'), 7.98 (1H, d, J$_{4'-5'}$=7.8 Hz, H4'), 11.66 (1H, s, indolic H); $^{13}$C NMR (DMSO, 75.5 MHz) δ (ppm): 104.6 (C2), 110.8 (C3'), 112.4 (C7'), 113.4 (C2''), 115.3 (C4''), 116.3 (C6''), 118.5 (C1), 119.2 (C4'), 120.4 (C5'), 122.3 (C6'), 123.7 (C3a'), 126.1 (C2'), 129.2 (C5''), 135.1 (C1''), 137.1 (C7a'), 138.0 (C3), 148.9 (C3''); ESI-MS: m/z 260.1 ([M+H]$^+$), 282.1 ([M+Na]$^+$); HRESI-MS: m/z 260.1149 (calcd for C$_{17}$H$_{14}$N$_3^+$, 260.1188), m/z 282.0977 (calcd for C$_{17}$H$_{13}$N$_3$Na$^+$, 282.1007).

EXAMPLE 44

(Z)-3-(3-amino-phenyl)-2-(1H-indol-3-yl)-acrylonitrile

EXAMPLE 45

(Z)-3-(3-amino-phenyl)-2-(5-methoxy-1H-indol-3-yl)-acrylonitrile

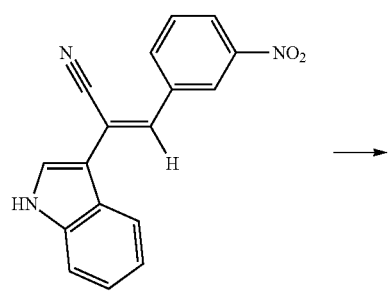

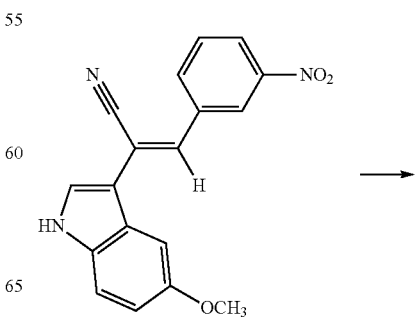

-continued

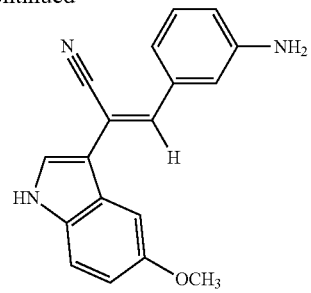

-continued

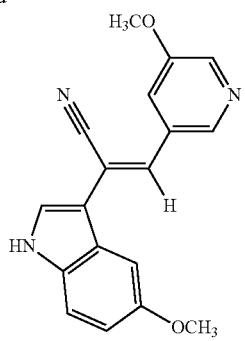

To a solution of (Z)-3-(3-amino-phenyl)-2-(1H-indol-3-yl)-acrylonitrile (90 mg, 0.3 mmol, 1.0 eq.) in acetic acid (8 mL) was added zinc powder (1.1 g). The reaction apparatus was protected from light and the mixture stirred at room temperature for 40 minutes. The mixture was filtered under celite, the filtrate evaporated under reduced pressure and the residue purified by silica gel flash-column chromatography (eluent: $CH_2Cl_2$/MeOH, 100/0 à 94/6). The product impure was solubilized with $CH_2Cl_2$ and the organic layer was washed with water and saturated aqueous sodium carbonate, and then, dried over $MgSO_4$ and evaporated under reduced pressure to afford the compound (45) as a yellow powder (58 mg, 72%). TLC: Rf=0.38 (heptane/EtOAc, 40/60); mp: 124° C.; IR $\nu_{max}$ (cm$^{-1}$): 2213 ($\nu_{CN}$), 3346 and 3403 ($\nu_{N-H}$); $^1$H NMR (DMSO, 300 MHz) δ (ppm): 3.81 (3H, s, 5'-methoxy), 5.25 (2H, s, aniline H), 6.63 (1H, d, $J_{4''-5''}$=8.0 Hz, H4''), 6.88 (1H, dd, $J_{6'-7'}$=8.9 Hz, $J_{6'-4'}$=2.4 Hz, H6'), 7.04 (2H, m, H2'' and H6''), 7.13 (1H, t, $J_{5''-4''}$=$J_{5''-6''}$=8.0 Hz, H5''), 7.39 (1H, d, $J_{7'-6'}$=8.9 Hz, H7'), 7.39 (1H, d, $J_{4'-6'}$=2.4 Hz, H4'), 7.51 (1H, s, H3), 7.70 (1H, m, H2'), 11.52 (1H, s, indolic H); $^{13}$C NMR (DMSO, 75.5 MHz) δ (ppm): 55.4 (5'-methoxy), 101.4 (C4'), 104.8 (C2), 110.5 (C3'), 112.2 (C6'), 113.1 (C7'), 113.5 (C2''), 115.2 (C4''), 116.2 (C6''), 118.5 (C1), 124.1 (C3a'), 126.6 (C2'), 129.2 (C5''), 132.1 (C7a'), 135.1 (C1''), 137.7 (C3), 148.9 (C3''), 154.3 (C5'); ESI-MS: m/z 290.1 ([M+H]$^+$), 312.1 ([M+Na]$^+$); HRESI-MS: m/z 290.1266 (calcd for $C_{18}H_{16}N_3O^+$, 290.1293), m/z 312.1092 (calcd for $C_{18}H_{15}N_3ONa^+$, 312.1113).

To a solution of sodium ethanolate [prepared from sodium (36 mg, 1.3 mmol, 1.2 eq.) in anhydrous ethanol (8 mL)] were added, under an argon atmosphere, (5-methoxy-1H-indol-3-yl)-acetonitrile (200 mg, 1.1 mmol, 1.0 eq.) and, after 10 minutes stirring, 5-methoxy-pyridine-3-carbaldehyde (175 mg, 1.3 mmol, 1.2 eq.). The reaction apparatus was protected from light and the mixture stirred at room temperature for 6 hours. The solvent was removed under reduced pressure and the residue purified by silica gel flash-column chromatography (eluent: $CH_2Cl_2$/MeOH, 99.5/0.5 to 97/3). The product impure was triturated with ethanol and diethyl ether to afford the compound (46) as a yellow powder (215 mg, 66%). TLC: Rf=0.44 ($CH_2Cl_2$/MeOH, 96/4); mp: 162° C.; IR $\nu_{max}$ (cm$^{-1}$): 2212 ($\nu_{CN}$); $^1$H NMR (DMSO, 300 MHz) δ (ppm): 3.83 (3H, s, 5'-methoxy), 3.89 (3H, s, 5''-methoxy), 6.90 (1H, d, $J_{6'-7'}$=8.9 Hz, H6'), 7.40 (1H, d, $J_{7'-6'}$=8.9 Hz, H7'), 7.48 (1H, s, H4'), 7.72 (1H, s, H3), 7.78 (1H, s, H2'), 7.91 (1H, s, H4''), 8.32 (1H, m, H6''), 8.61 (1H, s, H2''), 11.66 (1H, s, indolic H); $^{13}$C NMR (DMSO, 75.5 MHz) δ (ppm): 55.6 (5'- and 5''-methoxy), 102.0 (C4'), 108.4 (C2), 110.1 (C3'), 112.3 (C6'), 113.2 (C7'), 118.1 (C1), 118.7 (C4''), 123.9 (C3a'), 127.7 (C2'), 131.4 (C3''), 131.8 (C3), 132.2 (C7a'), 137.5 (C6''), 142.0 (C2''), 154.5 (C5'), 155.1 (C5''); ESI-MS: m/z 306.1 ([M+H]$^+$); HRESI-MS: m/z 306.1232 (calcd for $C_{18}H_{16}N_3O_2$, 306.1243); Anal. Calcd for $C_{18}H_{15}N_3O_2$, 0.1 $H_2O$: C, 70.39; H, 4.99; N, 13.68; O, 10.94.

EXAMPLE 46

(Z)-2-(5-methoxy-1H-indol-3-yl)-3-(5-methoxy-pyridin-3-yl)-acrylonitrile

EXAMPLE 47

(Z)-3-(4-chloro-pyridin-3-yl)-2-(5-methoxy-1H-indol-3-yl)-acrylonitrile

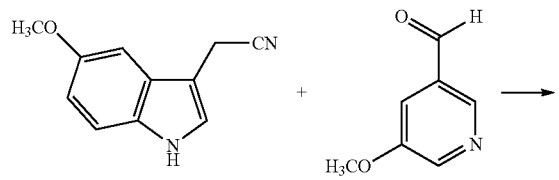

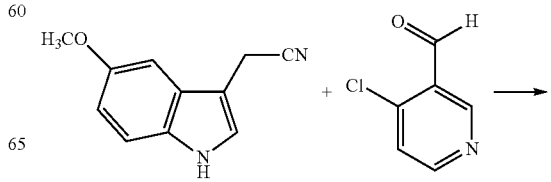

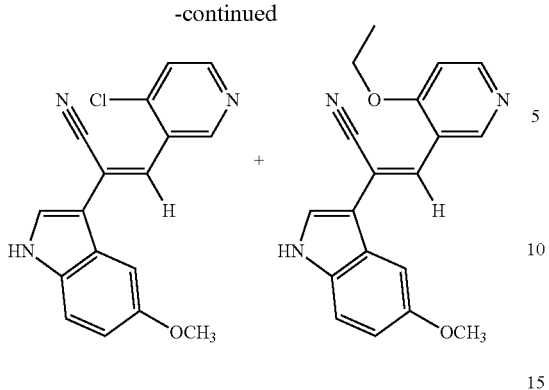

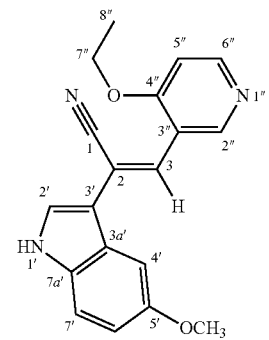

To a solution of sodium methanolate (30 mg, 0.55 mmol, 1.1 eq.) in anhydrous ethanol (10 mL) were added, under an argon atmosphere, (5-methoxy-1H-indol-3-yl)-acetonitrile (93 mg, 0.50 mmol, 1.0 eq.) and, after 10 minutes stirring, 4-chloro-pyridine-3-carbaldehyde (85 mg, 0.60 mmol, 1.2 eq.). The reaction apparatus was protected from light and the mixture heated at reflux for 2 hours. The reaction was allowed to cool to room temperature and then, the solvent was removed under reduced pressure and the crude taken up in ethyl acetate. The organic layer was washed with water, dried over MgSO$_4$ and then, evaporated. The residue was purified by silica gel flash-column chromatography (eluent: CH$_2$Cl$_2$/EtOH, 96/4) to afford two different compounds as described hereafter, after trituration with diethyl ether, (47a) (20 mg, 12%) and (47b) (40 mg, 25%) as yellow powders, namely:

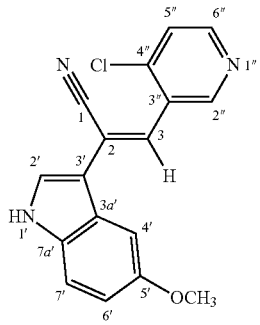

TLC: Rf=0.30 (CH$_2$Cl$_2$/EtOH, 96/4); IR $\nu_{max}$ (cm$^{-1}$): 2218 ($\nu_{CN}$); $^1$H NMR (DMSO, 300 MHz) δ (ppm): 3.82 (3H, s, 5'-methoxy), 6.92 (1H, dd, J$_{6'-7'}$=8.9 Hz, J$_{6'-4'}$=2.1 Hz, H6'), 7.44 (1H, d, J$_{7'-6'}$=8.9 Hz, H7'), 7.45 (1H, s, H4'), 7.73 (1H, s, H3), 7.74 (1H, d, J$_{5''-6''}$=5.2 Hz, H5''), 7.84 (1H, s, H2'), 8.59 (1H, d, J$_{6''-5''}$=5.2 Hz, H6''), 9.06 (1H, s, H2''), 11.76 (1H, s, indolic H); $^{13}$C NMR (DMSO, 75.5 MHz) δ (ppm): 55.9 (5'-methoxy), 101.9 (C4'), 110.2 (C3'), 111.9 (C2), 113.1 (C6'), 113.9 (C7'), 117.7 (C1), 124.4 (C3a'), 125.0 (C5''), 128.7 and 128.9 (C2' and C3), 130.6 (C3''), 132.7 (C7a'), 142.8 (C4''), 149.9 (C2''), 151.1 (C6''), 155.2 (C5'); ESI-MS: m/z 310.1 ([M+H]$^+$), 332.1 ([M+Na]$^+$), 364.1 ([M+Na+MeOH]$^+$); HRESI-MS: m/z 332.0573 (calcd for C$_{17}$H$_{12}$N$_3$ONaCl$^+$, 332.0567), and This last compound however displays no activity and accordingly, is not considered in the scope of the instant invention.

EXAMPLE 48

(Z)-3-(2-fluoropyridin-3-yl)-2-(5-methoxy-1H-indol-3-yl)-acrylonitrile

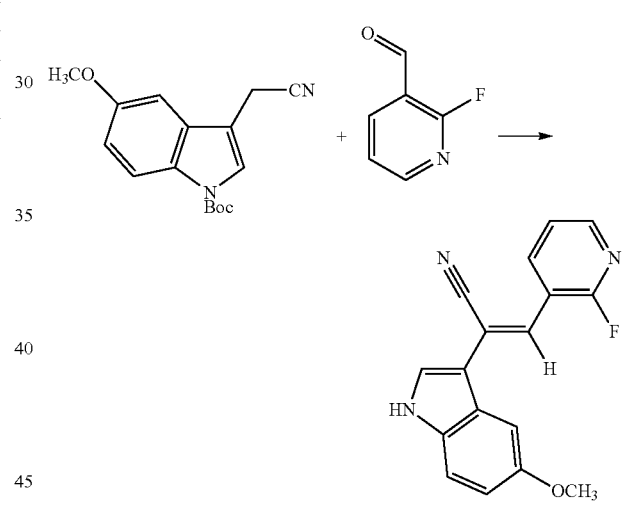

To a solution of tert-butyl 3-(cyanomethyl)-5-methoxy-1H-indol-1-carboxylate (719 mg, 2.51 mmol, 1.0 eq.) in anhydrous THF (30 mL) was added, under an argon atmosphere, NaH (106 mg, 80%, 3.52 mmol, 1.4 eq.). The mixture was stirred at room temperature for 2 hours, and then cooled to 0° C. before the addition of 2-fluoro-pyridine-3-carbaldehyde (440 mg, 3.52 mmol, 1.4 eq.) in anhydrous THF (6 mL). The reaction apparatus was protected from light and the mixture was stirred at 0° C. for 24 hours, at room temperature for 24 hours too and then, quenched with a saturated aqueous ammonium chloride solution. The mixture was stirred again at room temperature for 24 hours and extracted with ethyl acetate. The organic layer was washed with brine and dried over MgSO$_4$. The solvent was removed under reduced pressure, and the residue purified by silica gel flash-column chromatography (eluent: CH$_2$Cl$_2$/EtOH, 98/2) to afford, after trituration with diethyl ether, the compound (48) as a yellow powder (220 mg, 30%). IR $\nu_{max}$ (cm$^{-1}$): 2219 ($\nu_{CN}$), 3228 ($\nu_{N-H}$); $^1$H NMR (DMSO, 300 MHz): δ (ppm): 3.81 (3H, s, 5'-methoxy), 6.91 (1H, dd, J$_{6'-7'}$=8.9 Hz, J$_{6'-4'}$=2.1 Hz, H6'), 7.42 (1H, d, $J_{7'-6'}$=8.9 Hz, H7'), 7.43 (1H, d, $J_{4'-6'}$=2.4 Hz, H4'), 7.53 (1H, m, H5"), 7.64 (1H, s, H3), 7.84 (1H, s, H2'), 8.29 (1H, d, $J_{6''-5''}$=4.5 Hz, H6"), 8.49 (1H, m, H4"), 11.73 (1H, s, indolic H); $^{13}$C NMR (DMSO, 75.5 MHz): δ (ppm): 55.5 (5'-methoxy), 101.5 (C4'), 109.8 (C2), 110.0 (C3'), 112.5 (C6'), 113.3 (C7'), 117.3 (C1), 118.0 (1C, d, $^2J_{C-F}$=28 Hz, C3"), 122.3 (1C, d, $^4J_{C-F}$=4 Hz, C5"), 123.9 (C3a'), 125.8 (C3), 128.1 (C2'), 132.2 (C7a'), 139.4 (1C, d, $^3J_{C-F}$=3 Hz, C4"), 147.5 (1C, d, $^3J_{C-F}$=15 Hz, C6"), 154.7 (C5'), 159.7 (1C, d, $^1J_{C-F}$=270 Hz, C2"); ESI: 294.1 ([M+H]$^+$), 316.1 ([M+Na]$^+$), 348.1 ([M+Na+MeOH]$^+$); HRESI-MS: m/z 316.0861 (calcd for $C_{17}H_{12}N_3OFNa^+$, 316.0862).

EXAMPLE 49

(Z)-3-(6-chloropyridin-3-yl)-2-(5-methoxy-1H-indol-3-yl)-acrylonitrile

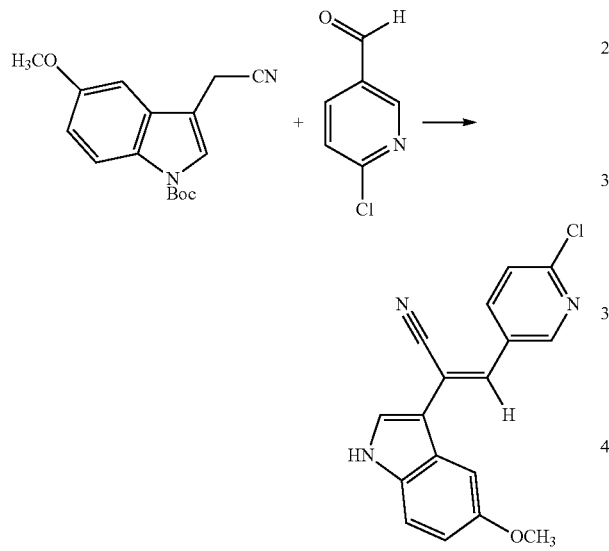

To a solution of tert-butyl 3-(cyanomethyl)-5-methoxy-1H-indol-1-carboxylate (4.9 g, 17 mmol, 1.0 eq.) in anhydrous THF (400 mL) was added, under an argon atmosphere, NaH (930 mg, 80%, 31 mmol, 1.8 eq.). The mixture was stirred at room temperature for 10 minutes, and then cooled to 0° C. before the addition of 6-chloro-pyridine-3-carbaldehyde (3 g, 21 mmol, 1.2 eq.). The reaction apparatus was protected from light and the mixture was stirred at room temperature for 1 hour, and then quenched with a saturated aqueous ammonium chloride solution. The mixture was extracted with ethyl acetate and the organic layer was dried over MgSO$_4$. The solvent was removed under reduced pressure, and the residue purified by silica gel flash-column chromatography (eluent: CH$_2$Cl$_2$/EtOH, 99/1) to afford, after trituration with diethyl ether, the compound (49) as a yellow powder (3.8 g, 72%). TLC: Rf=0.40 (CH$_2$Cl$_2$/EtOH, 96/4); mp: 184° C.; IR $\nu_{max}$ (cm$^{-1}$): 2208 ($\nu_{CN}$); $^1$H NMR (DMSO, 300 MHz) δ (ppm): 3.83 (3H, s, 5'-methoxy), 6.90 (1H, dd, $J_{6'-7'}$=8.9 Hz, $J_{6'-4'}$=2.1 Hz, H6'), 7.40 (1H, d, $J_{7'-6'}$=8.9 Hz, H7'), 7.49 (1H, d, $J_{4'-6'}$=2.4 Hz, H4'), 7.67 (1H, d, $J_{5''-4''}$=8.5 Hz, H5"), 7.73 (1H, s, H3), 7.79 (1H, s, H2'), 8.37 (1H, dd, $J_{4''-5''}$=8.5 Hz, $J_{4''-2''}$=2.4 Hz, H4"), 8.81 (1H, d, $J_{2''-4''}$=2.4 Hz, H2"), 11.70 (1H, s, indolic H); $^{13}$C NMR (DMSO, 75.5 MHz) δ (ppm): 55.6 (5'-methoxy), 102.0 (C4'), 108.2 (C2), 110.1 (C3'), 112.4 (C6'), 113.2 (C7'), 117.8 (C1), 123.9 (C3a'), 124.2 (C5"), 128.0 (C2'), 130.3 (C3), 130.4 (C3"), 132.3 (C7a'), 137.9 (C4"), 149.8 (C6"), 150.2 (C2"), 154.6 (C5'); ESI-MS: 310.1 ([M+H]$^+$), 334.1 ([M+Na]$^+$); HRESI-MS: m/z 310.0733 (calcd for $C_{17}H_{13}N_3O^{35}Cl^+$, 310.0747).

EXAMPLE 50

(Z)-2-(5-methoxy-1H-indol-3-yl)-3-thiophen-3-yl-acrylonitrile

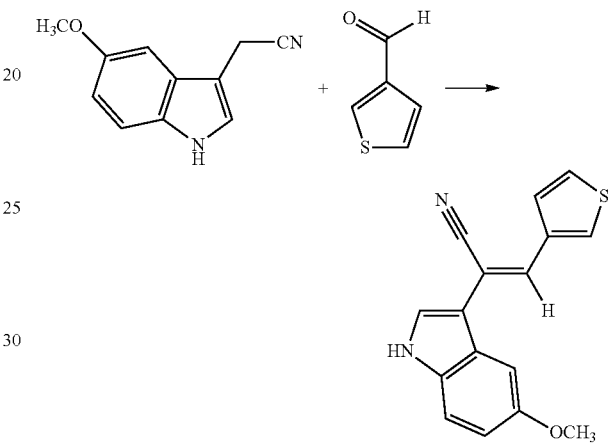

To a solution of sodium methanolate (204 mg, 3.8 mmol, 1.4 eq.) in anhydrous ethanol (30 mL) were added, under an argon atmosphere, (5-methoxy-1H-indol-3-yl)-acetonitrile (500 mg, 2.7 mmol, 1.0 eq.) and, after 30 minutes stirring, thiophen-3-carbaldehyde (235 µL, 2.7 mmol, 1.0 eq.). The reaction apparatus was protected from light and the mixture heated at 50° C. for 18 hours. The reaction was allowed to cool to room temperature and then, the solvent was removed under reduced pressure and the crude taken up in ethyl acetate. The organic layer was washed with water and brine, dried over MgSO$_4$ and then, evaporated. The residue was purified by silica gel flash-column chromatography (eluent: CH$_2$Cl$_2$) to afford, after trituration with heptane and diethyl ether, the compound (50) as a beige solid (310 mg, 41%). IR $\nu_{max}$ (cm$^{-1}$): 2212 ($\nu_{CN}$), 3340 ($\nu_{N-H}$); $^1$H NMR (DMSO, 300 MHz) δ (ppm): 3.82 (3H, s, 5'-methoxy), 6.88 (1H, dd, $J_{6'-7'}$=8.9 Hz, $J_{6'-4'}$=2.4 Hz, H6'), 7.38 (1H, d, $J_{7'-6'}$=8.9 Hz, H7'), 7.42 (1H, d, $J_{4'-6'}$=2.4 Hz, H4'), 7.69 (1H, d, $J_{4''-5''}$=5.1 Hz, H4"), 7.70 (1H, m, H3), 7.72 (1H, m, H2'), 7.79 (1H, dd, $J_{5''-4''}$=5.1 Hz, $J_{5''-2''}$=1.3 Hz, H5"), 8.10 (1H, m, H2"), 11.54 (1H, s, indolic H); $^{13}$C NMR (DMSO, 75.5 MHz) δ (ppm): 55.5 (5'-methoxy), 101.7 (C4'), 103.8 (C2), 109.9 (C3'), 112.1 (C6'), 113.0 (C7'), 118.1 (C1), 124.0 (C3a'), 126.5 (C4" and C5"), 127.3 (C2'), 128.0 (C2"), 130.6 (C3), 132.2 (C7a'), 136.6 (C3"), 154.3 (C5'); ESI-MS: m/z 281.1 ([M+H]$^+$), 303.1 ([M+Na]$^+$); HRESI-MS: m/z 303.0568 (calcd for $C_{16}H_{12}N_2ONaS^+$, 303.0568).

EXAMPLE 51

(Z)-2-(5-methoxy-1H-indol-3-yl)-3-(1-methyl-1H-pyrazol-3-yl)-acrylonitrile

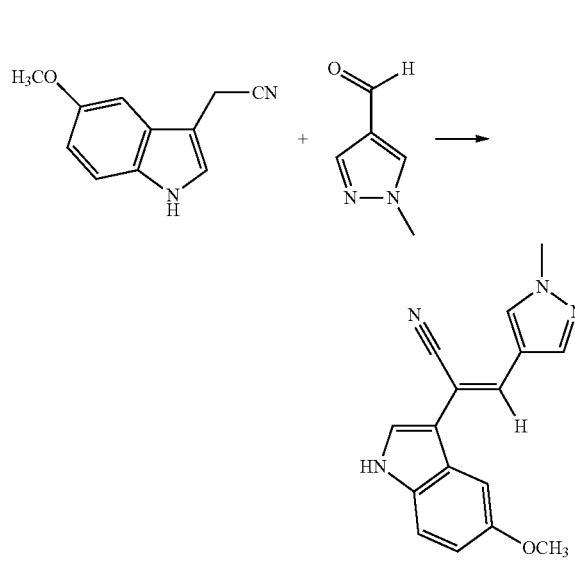

EXAMPLE 52

(Z)-3-(6-methoxy-pyridin-3-yl)-2-(5-methoxy-1H-indol-3-yl)-acrylonitrile

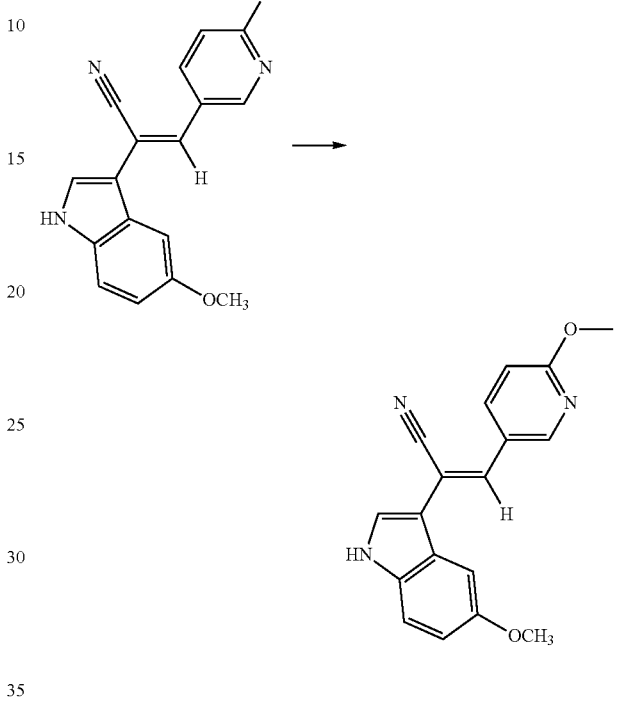

To a solution of sodium methanolate (204 mg, 3.8 mmol, 1.4 eq.) in anhydrous ethanol (30 mL) were added, under an argon atmosphere, (5-methoxy-1H-indol-3-yl)-acetonitrile (500 mg, 2.7 mmol, 1.0 eq.) and, after 30 minutes stirring, 1-methyl-1H-pyrazole-4-carbaldehyde (326 mg, 3.0 mmol, 1.1 eq.). The reaction apparatus was protected from light and the mixture heated at 50° C. for 18 hours. The reaction was allowed to cool to room temperature and then, the solvent was removed under reduced pressure and the crude taken up in ethyl acetate. The organic layer was washed with water and brine, dried over MgSO$_4$ and then, evaporated. The residue was purified by silica gel flash-column chromatography (eluent: CH$_2$Cl$_2$/EtOH, 99/1 to 98/2) to afford, after trituration with diethyl ether, the compound (51) as a beige powder (640 mg, 85%). mp: 178° C.; $^1$H NMR (DMSO, 300 MHz) δ (ppm): 3.81 (3H, s, 5'-methoxy), 3.92 (3H, s, N-methyl), 6.90 (1H, dd, J$_{6'-7'}$=8.7 Hz, J$_{6'-4'}$=2.3 Hz, H6'), 7.37 (1H, d, J$_{7'-6'}$=8.7 Hz, H7'), 7.38 (1H, m, H4'), 7.55 (1H, s, H3), 7.61 (1H, s, H2'), 8.00 (1H, s, H3''), 8.24 (1H, s, H5''), 11.43 (1H, s, indolic H); $^{13}$C NMR (DMSO, 75.5 MHz) δ (ppm): 38.8 (N-methyl), 55.6 (5'-methoxy), 101.5 (C2), 101.5 (C4'), 109.8 (C3'), 111.9 (C6'), 112.9 (C7'), 117.4 (C4''), 119.3 (C1), 124.0 (C3a'), 125.6 (C2'), 128.5 (C3), 131.0 (C5''), 132.1 (C7a'), 138.8 (C3''), 154.1 (C5'); MS: ESI-MS: m/z 264.1 ([M+H]$^+$), 286.1 ([M+Na]$^+$); HRESI-MS: m/z 301.1060 (calcd for C$_{16}$H$_{14}$N$_4$ONa$^+$, 301.1065); Anal. Calcd for C$_{19}$H$_{14}$N$_4$O, 0.1 H$_2$O: C, 68.61; H, 5.11; N, 20.00; O, 6.55. Found: C, 68.73; H, 5.33; N, 19.69.

To a mixture of (Z)-3-(6-chloropyridin-3-yl)-2-(5-methoxy-1H-indol-3-yl)-acrylonitrile (300 mg, 0.97 mmol, 1.0 eq.) in anhydrous DMSO (5 mL) and methanol (5 mL) was added NaH (232 mg, 80%, 7.75 mmol, 8 eq.). The reaction apparatus was protected from light and the mixture heated at 90° C. for 3 days. The reaction was allowed to cool to room temperature and then, the solvent was partially removed under reduced pressure and the crude taken up in ethyl acetate. The organic layer was washed with water, dried over MgSO$_4$, filtered through a silica gel pad and then, evaporated. The residue was triturated with diethyl ether to afford the compound (52) as a yellow solid (250 mg, 85%). IR ν$_{max}$ (cm$^{-1}$): 2213 (ν$_{CN}$), 3322 (ν$_{N-H}$); $^1$H NMR (DMSO, 300 MHz) δ (ppm): 3.82 (3H, s, 5'-methoxy), 3.92 (3H, s, H7''), 6.89 (1H, dd, J$_{6'-7'}$=8.9 Hz, J$_{6'-4'}$=2.1 Hz, H6'), 6.99 (1H, d, J$_{5''-4''}$=8.7 Hz, H5''), 7.39 (1H, d, J$_{7'-6'}$=8.9 Hz, H7'), 7.45 (1H, d, J$_{4'-6'}$=2.1 Hz, H4'), 7.67 (1H, s, H3), 7.73 (1H, s, H2'), 8.32 (1H, dd, J$_{4''-5''}$=8.7 Hz, J$_{4''-2''}$=2.4 Hz, H4''), 8.62 (1H, d, J$_{2''-4''}$=2.4 Hz, H2''), 11.58 (1H, s, indolic H); $^{13}$C NMR (DMSO, 75.5 MHz) δ (ppm): 54.0 (C7''), 56.0 (5'-methoxy), 102.2 (C4'), 105.6 (C2), 110.7 (C3'), 111.2 (C5''), 112.7 (C6'), 113.6 (C7'), 119.0 (C1), 124.5 (C3a'), 125.1 (C3''), 127.3 (C2'), 132.6 (C7a'), 133.3 (C3), 138.1 (C4''), 148.8 (C2''), 154.9 (C5'), 164.1 (C6''); ESI-MS: m/z 306.1 ([M+H]$^+$), 328.1 ([M+Na]$^+$); HRESI-MS: m/z 328.1063 (calcd for C$_{18}$H$_{15}$N$_3$O$_2$Na$^+$, 328.1062).

EXAMPLE 53

(Z)-2-(5-methoxy-1H-indol-3-yl)-3-(6-methylpyridin-3-yl)-acrylonitrile

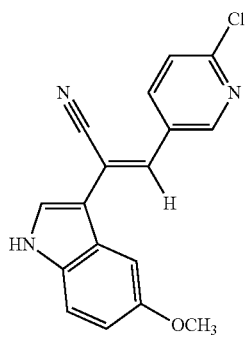  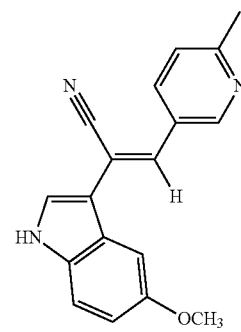

To a mixture of (Z)-3-(6-chloropyridin-3-yl)-2-(5-methoxy-1H-indol-3-yl)-acrylonitrile (200 mg, 0.64 mmol, 1.0 eq.) and Pd(PPh$_3$)$_4$ (37 mg, 0.03 mmol, 0.05 eq.) in anhydrous and degazed THF (10 mL) was added, under an argon atmosphere, a solution of AlMe$_3$ in hexane (640 µL, 2.0 M, 1.28 mmol, 2.0 eq.). The reaction apparatus was protected from light and the mixture was heated at 60° C. for 14 hours, and then, quenched with a saturated aqueous Rochelle salt solution, after cooling to room temperature. The mixture was extracted with ethyl acetate and the organic layer was washed with water, dried over MgSO$_4$, filtered through a silica gel pad and then, evaporated under reduced pressure. The residue was triturated with diethyl ether to afford the compound (53) as a yellow solid (170 mg, 92%). IR $\nu_{max}$ (cm$^{-1}$): 2206 ($\nu_{CN}$); $^1$H NMR (DMSO, 300 MHz) δ (ppm): 2.53 (3H, s, H7″), 3.83 (3H, s, 5′-methoxy), 6.89 (1H, dd, J$_{6'-7'}$=8.7 Hz, J$_{6'-4'}$=2.1 Hz, H6′), 7.40 (2H, d, J$_{7'-6'}$=8.7 Hz, J$_{5''-4''}$=8.7 Hz, H7′ and H5″), 7.46 (1H, d, J$_{4'-6'}$=2.1 Hz, H4′), 7.71 (1H, s, H3), 7.76 (1H, s, H2′), 8.23 (1H, dd, J$_{4''-5''}$=8.7 Hz, J$_{4''-2''}$=2.3 Hz, H4″), 8.85 (1H, d, J$_{2''-4''}$=2.4 Hz, H2″), 11.63 (1H, s, indolic H); $^{13}$C NMR (DMSO, 75.5 MHz) δ (ppm): 24.8 (C7″), 56.4 (5′-methoxy), 102.7 (C4′), 107.9 (C2), 111.1 (C3′), 113.2 (C6′), 114.0 (C7′), 119.1 (C1), 123.9 (C5″), 124.9 (C3a′), 128.2 (C2′), 128.9 (C3″), 133.1 (C7a′), 133.5 (C3), 135.6 (C4″), 150.3 (C2″), 155.3 (C5′), 159.3 (C6″); ESI-MS: m/z 290.1 ([M+H]$^+$); HRESI-MS: m/z 290.1295 (calcd for C$_{18}$H$_{16}$N$_3$O$^+$, 290.1293).

EXAMPLE 54

(Z)-5-[2-cyano-2-(5-methoxy-1H-indol-3-yl)-vinyl]-picolinonitrile

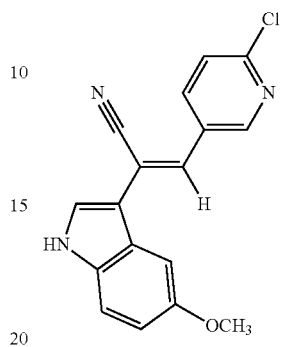 

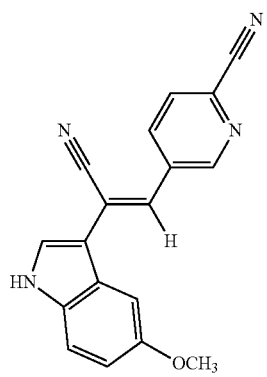

To a solution of (Z)-3-(6-chloropyridin-3-yl)-2-(5-methoxy-1H-indol-3-yl)-acrylonitrile (300 mg, 0.97 mmol, 1.0 eq.) in anhydrous NMP (4.0 mL) were added, under an argon atmosphere, Zn(CN)$_2$ (182 mg, 1.55 mmol, 1.6 eq.) and Pd(PPh$_3$)$_4$ (56 mg, 0.05 mmol, 0.05 eq.). The reaction apparatus was protected from light and the mixture was heated at 100° C. for 8 hours, and then, quenched with a saturated aqueous sodium bicarbonate solution, after cooling to room temperature. The mixture was extracted with ethyl acetate and the organic layer was washed with water, dried over MgSO$_4$, filtered through a silica gel pad and then, evaporated under reduced pressure. The residue was triturated with diethyl ether to afford the compound (54) as an orange powder (280 mg, 96%). mp: 221° C.; IR $\nu_{max}$ (cm$^{-1}$): 2216 and 2233 ($\nu_{CN}$); $^1$H NMR (DMSO, 300 MHz) δ (ppm): 3.83 (3H, s, 5-methoxy), 6.91 (1H, dd, J$_{6'-7'}$=8.9 Hz, J$_{6'-4'}$=2.1 Hz, H6′), 7.41 (1H, d, J$_{7'-6'}$=8.9 Hz, H7′), 7.52 (1H, d, J$_{4'-6'}$=2.1 Hz, H4′), 7.77 (1H, s, H1″), 7.85 (1H, s, H2′), 8.14 (1H, d, J$_{3-4}$=8.1 Hz, H3), 8.51 (1H, dd, J$_{4-3}$=8.1 Hz, J$_{4-6}$=2.1 Hz, H4), 9.11 (1H, d, J$_{6-4}$=2.1 Hz, H6), 11.80 (1H, s, indolic H); $^{13}$C NMR (DMSO, 75.5 MHz) δ (ppm): 55.6 (5′-methoxy), 102.3 (C4′), 110.3 (C2″), 111.0 (C3′), 112.5 (C6′), 113.3 (C7′), 117.5 (nitrile C), 123.9 (C3a′), 128.8 (C3), 128.9 (C2′), 129.1 (C1″), 131.1 (C2), 132.4 (C7a′), 134.6 (C5), 135.5 (C4), 151.3 (C6), 154.8 (C5′); ESI-MS: m/z 301.1 ([M+H]$^+$); HRESI-MS: m/z 301.1096 (calcd for C$_{18}$H$_{13}$N$_4$O$^+$, 301.1089).

EXAMPLE 55

(Z)-3-[2-cyano-2-(5-hydroxy-1H-indol-3-yl)-vinyl]-benzonitrile

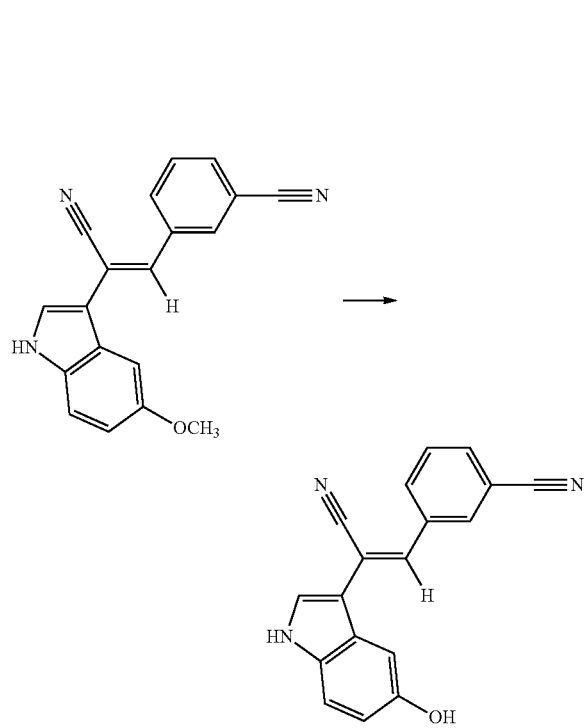

To a mixture of 54(Z)-3-[2-cyano-2-(5-methoxy-1H-indol-3-yl)-vinyl]-benzonitrile (300 mg, 1.0 mmol, 1.0 eq.) in anhydrous dichloromethane (4 mL) cooled to −78° C. was added, under an argon atmosphere, a 1M boron tribromide solution in dichloromethane (3 mL, 3.0 mmol, 3.0 eq.). The reaction mixture was stirred at ambient temperature for 18 hours ant then quenched with ethanol. The mixture was extracted with ethyl acetate and the organic layer was washed with water, dried over MgSO$_4$, filtered through a silica gel pad and then, evaporated under reduced pressure. The residue was triturated with diethyl ether to afford the compound (55) as an orange powder (260 mg, 91%). IR $v_{max}$ (cm$^{-1}$): 2213 and 2227 ($v_{CN}$), 3292 ($v_{N-H}$), 3390 ($v_{O-H}$); $^1$H NMR (DMSO, 500 MHz) δ (ppm): 6.77 (1H, dd, J$_{6'-7'}$=8.9 Hz, J$_{6'-4'}$=2.4 Hz, H6'), 7.30 (1H, d, J$_{7'-6'}$=8.9 Hz, H7'), 7.37 (1H, d, J$_{4'-6'}$=2.4 Hz, H4'), 7.65 (1H, s, H3), 7.71 (1H, m, H5"), 7.73 (1H, s, H2'), 7.86 (1H, d, J$_{6"-5"}$=7.6 Hz, H6"), 8.20 (1H, d, J$_{4"-6"}$=7.6 Hz, H4"), 8.25 (1H, s, H2"), 11.55 (1H, s, indolic H); $^{13}$C NMR (DMSO, 75.5 MHz) δ (ppm): 104.3 (C4'), 109.0 (C2), 110.1 (C3'), 112.8 (C6'), 112.4 (C3"), 113.3 (C6'), 113.4 (C7'), 118.4 and 118.9 (C1 and C nitrile), 124.9 (C3a'), 128.0 (C2'), 130.5 (C4"), 132.0 (C7a'), 132.5, 132.8 and 132.9 (C2", C5" and C3), 136.6 (C1"), 152.6 (C5'); ESI-MS: m/z 308.1 ([M+Na]$^+$); HRESI-MS: m/z 308.0789 (calcd for C$_{18}$H$_{11}$N$_3$ONa$^+$, 308.0800).

EXAMPLE 56

(Z)-2-(1H-indol-3-yl)-3-pyridin-3-yl-acrylamide

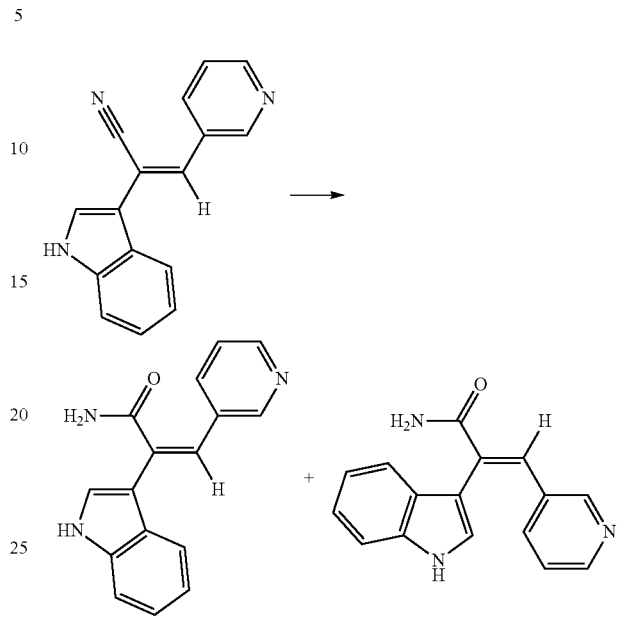

To a solution of (Z)-2-(1H-indol-3-yl)-3-pyridin-3-yl-acrylonitrile (600 mg, 2.4 mmol, 1.0 eq.) in tertiobutanol (20 mL) was added pulverized potassium hydroxide (2.24 g, 40 mmol, 16.7 eq). The reaction apparatus was protected from light and the mixture heated at reflux for 8 hours. The reaction was allowed to cool to room temperature and then, the solvent was partially removed under reduced pressure and the crude solubilized in ethyl acetate. The organic layer was washed with water and saturated aqueous ammonium chloride, and then dried over MgSO$_4$ and evaporated under reduced pressure. The residue was purified by silica gel flash-column chromatography (eluent: CH$_2$Cl$_2$/MeOH, 97/3 to 91/9) to afford the compound (56) as a yellow crystalline powder (407 mg, 64%).

TLC: Rf=0.32 (CH$_2$Cl$_2$/MeOH, 90/10); mp: 96° C.; IR $v_{max}$ (cm$^{-1}$): 1650 ($v_{C=O}$), 3158 ($v_{N-H}$); $^1$H NMR (DMSO, 500 MHz) δ (ppm): 6.96 (1H, s, H3), 7.13 (1H, t, J$_{5'-4'}$=J$_{5'-6'}$=7.9 Hz, H5'), 7.19 (1H, t, J$_{6'-5'}$=J$_{6'-7'}$=7.9 Hz, H6'), 7.37 (1H, dd, J$_{5"-4"}$=7.9 Hz, J$_{5"-6"}$=4.9 Hz, H5"), 7.46 (1H, d, J$_{7'-6'}$=7.9 Hz, H7'), 7.57 (1H, s, amide H), 7.90 (1H, s, amide H), 7.96 (1H, d, J$_{4"-5"}$=7.9 Hz, H4"), 7.99 (1H, d, J$_{4'-5'}$=7.9 Hz, H4'), 8.41 (1H, d, J$_{6"-5"}$=4.9 Hz, H6"), 8.76 (1H, s, H2"), 11.46 (1H, s, indolic H); $^{13}$C NMR (DMSO, 75.5 MHz) δ (ppm): 112.2 (C7'), 113.0 (C3'), 117.0 (C3), 120.0 (C5'), 120.2 (C4'), 121.9 (C6'), 123.4 (C5"), 124.5 (C3a'), 126.0 (C2'), 132.8 (C3"), 134.2 (C4"), 136.7 (C2), 137.1 (C7a'), 147.3 (C6"), 149.3 (C2"), 171.3 (amide C); ESI-MS: m/z 264.1 ([M+H]$^+$), 286.1 ([M+Na]$^+$); HRESI-MS: m/z 264.1134 (calcd for $C_{16}H_{14}N_3O^+$, 264.1137).

The remaining fractions were combined, concentrated under reduced pressure and the residue was triturated with diethyl ether to afford the hereafter compound as a yellow powder (66 mg, 10%).

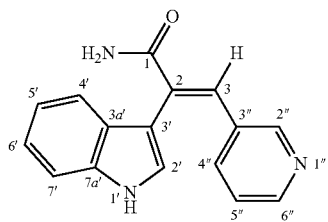 [SMILES: NC(=O)/C(=C/c1cccnc1)c1c[nH]c2ccccc12]

This last compound however displays no activity and accordingly, is not considered in the scope of the instant invention.

EXAMPLE 57

(E)-3-(2-pyridin-3-yl-vinyl)-1H-indole

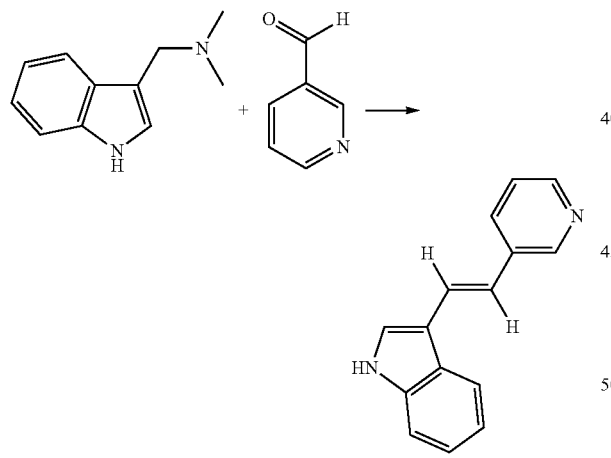

To a solution of gramine (174 mg, 1.0 mmol, 1.0 eq.) in anhydrous acetonitrile (3 mL) were added, under an argon atmosphere, pyridine-3-carbaldehyde (94 μl, 1.0 mmol, 1.0 eq.) and tributylphosphine (375 μL, 1.5 mmol, 1.5 eq.). The reaction mixture was heated in a sealed tube at reflux temperature for 26 hours. The reaction was allowed to cool to room temperature and then, the solvent was removed under reduced pressure and the residue purified by silica gel flash-column chromatography (eluent: heptane/EtOAc, 60/40 to 40/60). The product impure was triturated with ethanol and diethyl ether to afford the compound (57) as yellow crystals (180 mg, 82%). TLC: Rf=0.18 (heptane/EtOAc, 50/50); mp: 190° C.; $^1$H RMN (DMSO, 500 MHz): δ (ppm): 7.11 (1H, d, $J_{2-1}$=16.5 Hz, H2), 7.13 (1H, m, H5'), 7.18 (1H, m, H4'), 7.36 (1H, m, H5"), 7.43 (1H, d, $J_{7'-6'}$=7.6 Hz, H7'), 7.56 (1H, d, $J_{1-2}$=16.5 Hz, H1), 7.68 (1H, s, H2'), 8.01 (1H, m, H4"), 8.04 (1H, d, $J_{4'-5'}$=7.6 Hz, H4'), 8.37 (1H, m, H6"), 8.76 (1H, s, H2"), 11.39 (1H, s, indolic H); $^{13}$C NMR (DMSO, 75.5 MHz) δ (ppm): 112.0 (C7'), 113.5 (C3'), 119.4 (C2), 119.8 and 119.9 (C4' and C5'), 121.9 (C6'), 123.7 (C5"), 124.7 (C1), 125.1 (C3a'), 126.7 (C2'), 131.4 (C4"), 134.3 (C3"), 137.1 (C7a'), 147.0 (C6"), 147.5 (C2"); ESI-MS: m/z 221.1 ([M+H]$^+$); HRESI-MS: m/z 221.1076 (calcd for $C_{15}H_{13}N_2^+$, 221.1079); Anal. Calcd for $C_{15}H_{13}N_2$, 0.1 $H_2O$: C, 81.13; H, 5.54; N, 12.61. Found: C, 81.07; H, 5.48; N, 12.47.

EXAMPLE 58

(E)-5-methoxy-3-(1-(pyridin-3-yl)but-1-en-3-yn-2-yl)-1H-indole

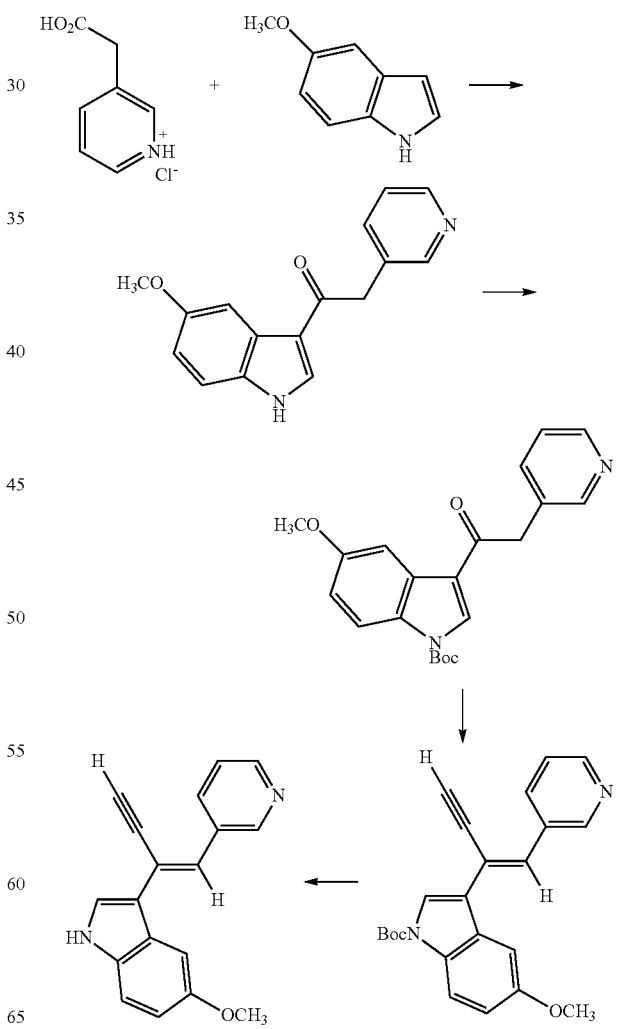

1) Preparation of 1-(5-methoxy-1H-indol-3-yl)-2-pyridin-3-yl-ethanone

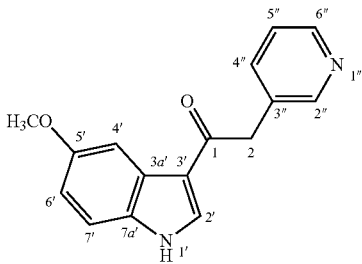 [SMILES: COc1ccc2[nH]cc(C(=O)Cc3cccnc3)c2c1]

A mixture of 3-pyridylacetic hydrochloride reduced in powder (2.36 g, 13.6 mmol, 1.0 eq.) in acetic anhydride was heated in a sealed tube at 85° C. for 60 minutes and then, 5-methoxyindole (2 g, 13.6 mmol, 1.0 eq.) was added. The whole was heated at 85° C. for 20 minutes and then, 105° C. for 30 minutes. The reaction was allowed to cool to room temperature and then ethyl acetate and water were added. The pH was adjusted to 7 with saturated aqueous sodium carbonate. The aqueous layer was extracted with ethyl acetate and then, the organic layer was dried over MgSO$_4$. The solvent was removed under reduced pressure and the residue purified by silica gel flash-column chromatography (eluent: CH$_2$Cl$_2$/EtOH, 96/4 to 94/6). The product impure was triturated with ethanol and diethyl ether to afford 1-(5-methoxy-1H-indol-3-yl)-2-pyridin-3-yl-ethanone as a beige powder (1.74 g, 48%).

2) Preparation of tert-butyl 5-methoxy-3-(2-(pyridin-3-yl)acetyl)-1H-indol-1-carboxylate

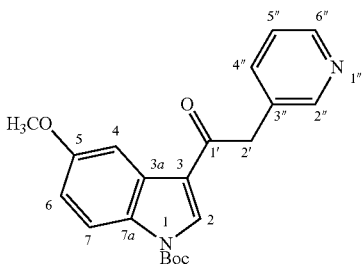 [SMILES: COc1ccc2c(c1)c(C(=O)Cc1cccnc1)cn2C(=O)OC(C)(C)C]

To a solution of 1-(5-methoxy-1H-indol-3-yl)-2-pyridin-3-yl-ethanone (1.00 g, 3.8 mmol, 1.0 eq.) and (Boc)$_2$O (1.20 mL, 5.6 mmol, 1.5 eq.) in anhydrous dichloromethane (70 mL) was added, under an argon atmosphere, DMAP (17 mg, 0.14 mmol, 0.04 eq.). The mixture was stirred at room temperature for 1 hour. The solvent was removed under reduced pressure, and the residue purified by silica gel flash-column chromatography (eluent: EtOAc/EtOH, 100/0 to 90/10) to afford, after trituration with diethyl ether, tert-butyl 5-methoxy-3-(2-(pyridin-3-yl)acetyl)-1H-indol-1-carboxylate as a white powder (1.28 g, 93%).

3) Preparation of (E)-tert-butyl 5-methoxy-3-(1-(pyridin-3-yl)but-1-en-3-yn-2-yl)-1H-indole-1-carboxylate

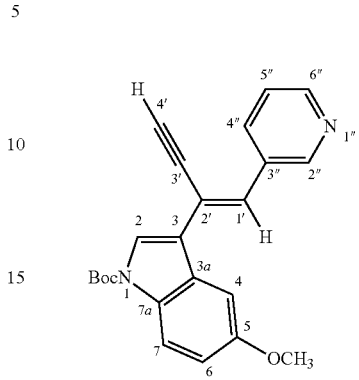

To a solution of trimethylsilylacetylene (5.5 mL, 39.3 mmol, 12.0 eq.) in anhydrous and degazed THF (240 mL) was added, under an argon atmosphere and at −78° C., a solution of n-BuLi in hexane (24.6 mL, 1.6 M, 39.3 mmol, 12.0 eq.). The resulting mixture was stirred for 20 minutes at −78° C. and then, at room temperature. Ketone tert-butyl 5-methoxy-3-(2-(pyridin-3-yl)acetyl)-1H-indol-1-carboxylate (1.2 g, 3.3 mmol, 1.0 eq.) was added little by little and then, the reaction was stirred at room temperature for 1 hour. The mixture was cooled to 0° C., quenched with a saturated aqueous ammonium chloride solution and extracted with ethyl acetate. The organic layer was dried over MgSO$_4$, evaporated under reduced pressure and the crude product was separated from the ketone reactant by silica gel flash-column chromatography (eluent: heptane/EtOAc, 60/40). To the alcohol residue taken up in toluene (150 mL) was added KHSO$_4$ (2.7 g, 19.6 mmol) and the mixture was heated at 70° C. for 40 hours and quenched with a saturated aqueous sodium bicarbonate solution, after cooling to room temperature. The mixture was extracted with ethyl acetate and the organic layer was dried over MgSO$_4$ and evaporated. The crude was taken up in ethanol (50 mL), K$_2$CO$_3$ (0.43 g, 3.1 mmol) was added, and the reaction mixture stirred at room temperature for 3 hours. The solvent was removed and the residue taken up in ethyl acetate. The organic layer washed with water, dried over MgSO$_4$, filtered through a silica gel pad and then, evaporated under reduced pressure to afford, after trituration with diethyl ether, (E)-tert-butyl 5-methoxy-3-(1-(pyridin-3-yl)but-1-en-3-yn-2-yl)-1H-indole-1-carboxylate as a beige solid (790 mg, 64%).

4) Preparation of (E)-5-methoxy-3-(1-(pyridin-3-yl)but-1-en-3-yn-2-yl)-1H-indole To a mixture of (E)-tert-butyl 5-methoxy-3-(1-(pyridin-3-yl)but-1-en-3-yn-2-yl)-1H-indole-1-carboxylate (270 mg, 0.72 mmol, 1.0 eq.) in ethanol (40 mL) were added K$_2$CO$_3$ (1.2 g, 8.6 mmol, 12.0 eq.) and sodium methanolate (232 mg, 4.3 mmol, 6.0 eq.), and then, the reaction was stirred at room temperature for 3 days. The solvent was removed and the residue taken up in ethyl acetate. The organic layer washed with water, dried over MgSO$_4$, filtered through a silica gel pad and then, evaporated under reduced pressure to afford, after trituration with diethyl ether, the compound (58) as a yellowish powder (180 mg, 91%). mp: 136° C.; IR $v_{max}$ (cm$^{-1}$): 2089 ($v_{CC\ alcyne}$); $^1$H RMN (DMSO, 300 MHz) δ (ppm): 3.81 (3H, s, 5-methoxy), 4.64 (1H, s, H4'), 6.84 (1H, dd, J$_{6-7}$=8.9 Hz, $J_{6-4}$=2.3 Hz, H6), 7.29 (1H, s, H1'), 7.35 (1H, d, $J_{7-6}$=8.9 Hz, H7), 7.42 (1H, dd, $J_{5''-4'}$=7.3 Hz, $J_{5''-6''}$=4.5 Hz, H5''), 7.49 (1H, d, $J_{4-6}$=2.3 Hz, H4), 7.67 (1H, s, H2), 8.46 (2H, m, H4'' and H6''), 9.03 (1H, s, H2''), 11.37 (1H, s, indolic H); $^{13}$C NMR (DMSO, 75.5 MHz) δ (ppm): 55.4 (5-methoxy), 82.5 (C3'), 86.7 (C4'), 102.2 (C4), 111.7 (C6), 112.8 (C7), 114.2 (C2'), 117.7 (C3), 123.2 (C5''), 124.4 (C3a), 126.4 (C1'), 127.0 (C2), 132.2 (C7a), 132.7 (C3''), 134.3 (C4''), 147.9 (C6''), 149.8 (C2''), 154.0 (C5); ESI-MS: m/z 275.1 ([M+H]$^+$); HRESI-MS: m/z 275.1176 (calcd for $C_{18}H_{15}N_2O^+$, 275.1184).

EXAMPLE 59

5-methoxy-3-(1-(pyridin-3-yl)prop-1-en-2-yl)-1H-indole

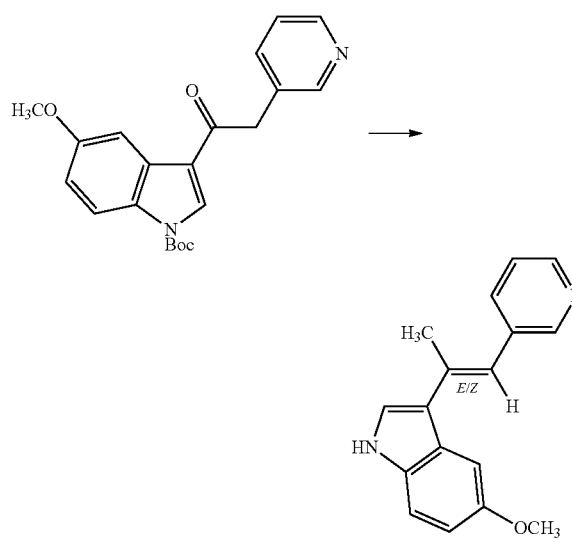

To a solution of MeLi in diethyl ether (5.1 mL, 1.6 M, 8.2 mmol, 6.0 eq.) and anhydrous and degazed THF (70 mL) was added, under an argon atmosphere and at 10° C., ketone tert-butyl 5-methoxy-3-(2-(pyridin-3-yl)acetyl)-1H-indol-1-carboxylate (1.2 g, 3.3 mmol, 1.0 eq.). The reaction mixture was stirred at 10° C. for 15 minutes and then, cooled to 0° C. and quenched with a saturated aqueous ammonium chloride solution. The mixture was extracted with ethyl acetate and the organic layer was dried over MgSO$_4$ and evaporated under reduced pressure. To the alcohol residue taken up in toluene (70 mL) was added KHSO$_4$ (1.1 g, 8.2 mmol) and the mixture was heated at 70° C. for 18 hours and quenched with a saturated aqueous sodium bicarbonate solution, after cooling to room temperature. The mixture was extracted with ethyl acetate and the organic layer was dried over MgSO$_4$ and evaporated. The residue was purified by silica gel flash-column chromatography (eluent: CH$_2$Cl$_2$/EtOH, 99/1 to 97/3) to afford the two diastereoisomers represented herein only by the compound (59), namely the major one (E), as a yellow mering (200 mg, 56%, E/Z ratio: 80/20). TLC: Rf=0.30 (CH$_2$Cl$_2$/EtOH, 96/4); IR $v_{max}$ (cm$^{-1}$): 2925 ($v_{C-H\ aliphatic}$); $^1$H RMN (DMSO, 500 MHz) δ isomere E (ppm): 2.29 (3H, s, 3H3'), 3.80 (3H, s, 5-methoxy), 6.82 (1H, dd, $J_{6-7}$=8.9 Hz, $J_{6-4}$=2.3 Hz, H6), 6.93 (1H, s, H1'), 7.33 (1H, d, $J_{7-6}$=8.9 Hz, H7), 7.39 (2H, m, H4 et H5''), 7.59 (1H, s, H2), 7.82 (1H, d, $J_{4''-5''}$=7.9 Hz, H4''), 8.40 (1H, d, $J_{6''-5''}$=4.6 Hz, H6''), 8.63 (1H, s, H2''), 11.21 (1H, s, indolic H); $^{13}$C NMR (DMSO, 75.5 MHz) δ isomere E (ppm): 18.5 (C3'), 55.9 (5-methoxy), 103.0 (C4), 111.8 (C6), 113.1 (C7), 118.1 (C3), 119.2 (C1'), 123.7 (C5''), 125.3 (C3a), 126.1 (C2), 132.7 (C7a), 134.8 (C3''), 135.1 (C2'), 136.2 (C4''), 146.8 (C6''), 150.4 (C2''), 154.4 (C5); ESI-MS: m/z 265.2 ([M+H]$^+$); HRESI-MS: m/z 265.1340 (calcd for $C_{17}H_{17}N_2O^+$, 265.1341).

EXAMPLE 60

(Z)-2-(5-methoxy-1H-indol-3-yl)-3-(pyridin-3-yl)-but-2-enenitrile

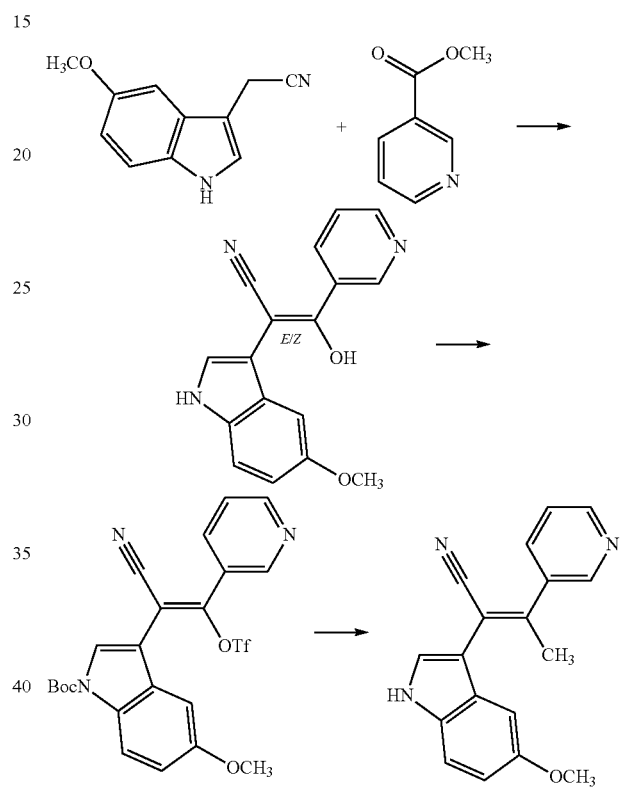

1) Preparation of 3-hydroxy-2-(5-methoxy-1H-indol-3-yl)-3-(pyridin-3-yl)acrylonitrile

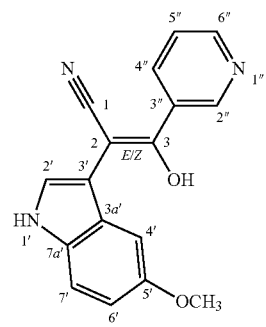

To a suspension of NaH (780 mg, 80%, 26 mmol, 1.6 eq.) in anhydrous THF (50 mL) were added, under an argon atmosphere, (5-methoxy-1H-indol-3-yl)-acetonitrile (3 g, 16 mmol, 1.0 eq.) and, after 30 minutes stirring at room temperature, methyl nicotinate (2.9 g, 21 mmol, 1.3 eq.). The reaction mixture was heated in a sealed tube at 60° C. for 13 hours. The reaction was allowed to cool to room temperature and then, treated with a saturated aqueous ammonium chloride solution. The mixture was extracted with ethyl acetate and the organic layer was washed with water and brine, and then dried over $MgSO_4$. The solvent was removed under reduced pressure, and the residue purified by silica gel flash-column chromatography (eluent: $CH_2Cl_2$/EtOH, 96/4 to 95/5) to afford 3-hydroxy-2-(5-methoxy-1H-indol-3-yl)-3-(pyridin-3-yl) acrylonitrile as orange specks (2.5 g, 53%, E/Z ratio: 85/15).

2) Preparation of (E)-tert-butyl-3-(1-cyano-2-(pyridin-3-yl)-2-trifluoromethylsulfonyloxy)vinyl)-5-methoxy-1H-indole-1-carboxylate

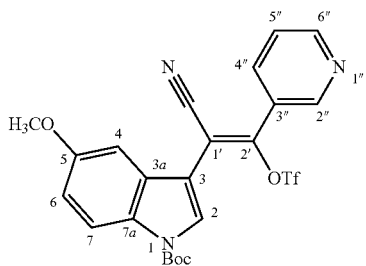 [SMILES: COc1ccc2c(c1)c(/C(C#N)=C(\OS(=O)(=O)C(F)(F)F)c1cccnc1)cn2C(=O)OC(C)(C)C]

To a solution of (E/Z)-3-hydroxy-2-(5-methoxy-1H-indol-3-yl)-3-(pyridin-3-yl)acrylonitrile as orange specks (4.5 g, 15.4 mmol, 1.0 eq.) in anhydrous NMP (160 mL) maintained at 0° C. were added, under an argon atmosphere, phenyltriflimide (5.5 g, 15.4 mmol, 1.0 eq.) and $K_2CO_3$ (2.1 g, 15.4 mmol, 1.0 eq.). The reaction apparatus was protected from light and the mixture was stirred at 0° C. for 20 minutes, and then diluted with cold ethyl acetate. The organic layer was washed with water, brine, dried over $MgSO_4$ and filtered through a silica gel pad. To triflate in ethyl acetate were added, under an argon atmosphere and at 0° C., $(Boc)_2O$ (3.6 mL, 16.9 mmol, 1.1 eq.) and DMAP (0.18 g, 1.5 mmol, 0.1 eq.). The mixture was stirred at 0° C. for 40 minutes, and then quenched with a saturated aqueous bicarbonate solution. The organic layer was washed with water and brine, dried over $MgSO_4$ and then, evaporated under reduced pressure. The residue was purified by silica gel flash-column chromatography (eluent: heptane/AcOEt, 70/30) to afford (E)-tert-butyl-3-(1-cyano-2-(pyridin-3-yl)-2-trifluoromethylsulfonyloxy) vinyl)-5-methoxy-1H-indole-1-carboxylate as an orange solid (6.1 g, 76%).

3) Preparation of (Z)-2-(5-methoxy-1H-indol-3-yl)-3-(pyridin-3-yl)-but-2-enenitrile To a mixture of $Pd(PPh_3)_4$ (44 mg, 0.04 mmol, 0.05 eq.) and (E)-tert-butyl-3-(1-cyano-2-(pyridin-3-yl)-2-trifluoromethylsulfonyloxy)vinyl)-5-methoxy-1H-indole-1-carboxylate (400 mg, 0.76 mmol, 1.0 eq.) in anhydrous and degazed THF (12.0 mL) was added, under an argon atmosphere, a solution of $AlMe_3$ in hexane (760 µL, 2.0 M, 1.52 mmol, 2.0 eq.). The reaction apparatus was protected from light and the mixture was heated at 50° C. for 8 hours, and then, quenched with a saturated aqueous Rochelle salt solution, after cooling to room temperature. The mixture was extracted with ethyl acetate and the organic layer was washed with water, dried over $MgSO_4$, filtered through a silica gel pad and then, evaporated under reduced pressure. The residue was taken up in a mixture of dichloromethane (20.0 mL) and TFA (5.0 mL), and then the reaction mixture was stirred at room temperature for 2 hours and quenched with a 1M aqueous sodium hydroxide solution. The mixture was extracted with ethyl acetate and then, the organic layer was washed with water, dried over $MgSO_4$ and evaporated under reduced pressure. The residue was purified by silica gel flash-column chromatography (eluent: heptane/AcOEt, 60/40 to 30/70) to afford, after trituration with diethyl ether, the compound (60) as a yellow solid (120 mg, 55%). IR $v_{max}$ ($cm^{-1}$): 2213 ($v_{CN}$); $^1$H NMR (DMSO, 300 MHz) δ (ppm): 2.32 (3H, s, 4-méthyl), 3.78 (3H, s, 5'-methoxy), 6.86 (1H, dd, $J_{6'-7'}$=8.9 Hz, $J_{6'-4'}$=2.3 Hz, H6'), 7.10 (1H, d, $J_{4'-6'}$=2.3 Hz, H4'), 7.39 (1H, d, $J_{7'-6'}$=8.9 Hz, H7'), 7.54 (1H, dd, $J_{5''-4''}$=7.9 Hz, $J_{5''-6''}$=4.7 Hz, H5''), 7.62 (1H, m, H2'), 8.06 (1H, d, $J_{4''-5''}$=7.9 Hz, H4''), 8.65 (1H, d, $J_{6''-5''}$=4.7 Hz, H6''), 8.85 (1H, d, $J_{2''-4''}$=1.8 Hz, H2''), 11.52 (1H, s, indolic H); $^{13}$C NMR (DMSO, 75.5 MHz) δ (ppm): 22.7 (C4), 55.9 (5'-methoxy), 101.3 (C4'), 106.2 (C2), 108.0 (C3'), 112.6 (C6'), 113.4 (C7'), 119.4 (C1), 123.9 (C5''), 126.2 (C3a'), 127.7 (C2'), 131.4 (C3''), 136.0 (C4''), 137.3 (C7a'), 148.8 (C6''), 150.2 (C2''), 150.9 (C3), 154.4 (C5'); ESI-MS: m/z 290.1 ([M+H]$^+$), 312.1 ([M+Na]$^+$); HRESI-MS: m/z 312.1125 (calcd for $C_{18}H_{15}N_3ONa^+$, 312.1113).

EXAMPLE 61

(Z)-(1H-indol-3-yl)-(pyridin-3-ylimino)-acetonitrile

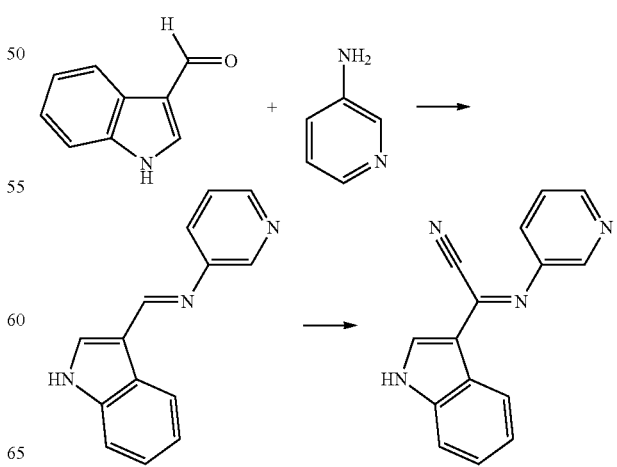

1) Preparation of (Z)-(1H-indol-3-ylmethylene)-pyridin-3-amine

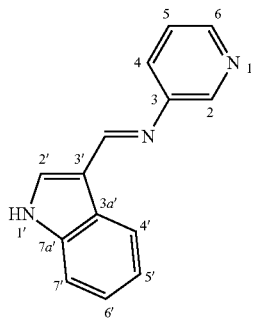

A mixture of indole-3-carbaldehyde (1 g, 6.9 mmol, 1.0 eq.) and pyridin-3-ylamine (843 mg, 9.0 mmol, 1.3 eq.) in anhydrous dichloromethane (15 mL) was heated in a sealed tube at reflux temperature for 36 hours. The reaction was allowed to cool to room temperature and then, the insoluble was filtered, washed with dichloromethane and diethyl ether to afford (Z)-(1H-indol-3-ylmethylene)-pyridin-3-amine as a beige powder (1.5 g, Rdt: 98%).

2) Preparation of (Z)-(1H-indol-3-yl)-(pyridin-3-ylimino)-acetonitrile

To a solution of (Z)-(1H-indol-3-ylmethylene)-pyridin-3-amine (400 mg, 1.8 mmol, 1.0 eq.) in anhydrous DMSO (30 mL) was added sodium cyanide (266 mg, 5.4 mmol, 3.0 eq.). The whole was stirred at room temperature for 4 hours under an argon atmosphere, and then under air bubbling for 40 hours. The mixture was poured into water and extracted with ethyl acetate. The combined organic layers were washed with aqueous bicarbonate solution, and then dried over $MgSO_4$. The solvent was removed under reduced pressure and the residue was triturated with ethanol and diethyl ether to afford the compound (61) as a yellow powder (290 mg, 65%). IR $v_{max}$ (cm$^{-1}$): 1573 ($v_{C=N}$), 2213 ($v_{CN}$); $^1$H NMR (DMSO, 300 MHz): δ (ppm): 7.26 (1H, t, $J_{5'-6'}$=$J_{5'-4'}$=7.9 Hz, H5'), 7.33 (1H, t, $J_{6'-5'}$=$J_{6'-7'}$=7.9 Hz, H6'), 7.51 (1H, dd, $J_{5''-4''}$=8.0 Hz, $J_{5''-6''}$=4.7 Hz, H5''), 7.56 (1H, d, $J_{7'-6'}$=7.9 Hz, H7'), 7.66 (1H, d, $J_{4''-5''}$=8.0 Hz, H4''), 8.27 (1H, d, $J_{4'-5'}$=7.9 Hz, H4'), 8.30 (1H, s, H2'), 8.45 (1H, d, $J_{2''-4''}$=2.4 Hz, H2''), 8.48 (1H, d, $J_{6''-5''}$=4.7 Hz, H6''), 12.35 (1H, s, indolic H); $^{13}$C NMR (DMSO, 75.5 MHz) δ (ppm): 111.1 (C3'), 112.7 (C7'), 113.6 (C1), 121.7 (C4'), 122.3 (C5'), 123.8 (C5''), 124.1 (C6'), 128.0 (C4''), 135.2 (C2'), 136.2 (C2), 137.5 (C7a'), 141.7 (C2''), 146.3 (C3''), 146.7 (C6''); ESI-MS: m/z 247.1 ([M+H]$^+$); HRESI-MS: m/z 247.0972 (calcd for $C_{15}H_{10}N_4^+$, 247.0984); Anal. Calcd for $C_{15}H_{10}N_4$, 0.1 $H_2O$: C, 72.63; H, 4.14; N, 22.58. Found: C, 72.14; H, 4.11; N, 22.32.

EXAMPLE 62

Some compounds of the previous examples have been the subject of tests which have demonstrated their specific relevance as inhibitor substances against MKLP-2.

Materials and Methods a—Materials.

BL21(DE3) competent cells were bought from Novagen. His-trap columns FF (1 ml) and the Superose 12 column were purchased from GE Healthcare. Amicon Ultra concentrators were from Millipore. The QickChange silent mutagenesis kit was obtained from Stratagene. Taxol, nocodazol, dihydrocytochalasin B, SYBR GREEN I, and the primary monoclonal mouse antitubulin antibody were purchased from Sigma. Low melting point agarose was obtained from Invitrogen. NcoI and XhoI restriction enzymes were bought from NEB Biolabs. DMEM was obtained from Life Technologies, Rockville, Md.

b—Cloning.

Expression clones for MKLP-$2_{1-519}$ (coding for residues 1 to 519) were obtained as follows: first, the XhoI restriction site in the MKLP-2 cDNA was eliminated by silent mutagenesis using forward (5'-c agc aag ttg act cgC gtg ttc caa ggt ttc-3') and reverse (5'-gaa acc ttg gaa cac Gcg agt caa ctt gct g-3') primers. Subsequently, XhoI could not restrict positive clones. Second, a fragment coding for the first N-terminal 519 residues was synthesized by PCR with the following forward (5'-ta ggc tgc cct gcc gCc ATG Gcg caa ggg atc ctt t-3') and reverse (5'-ttc ctt gat gaa cga ctC GaG gga tgg gaa tcc cag-3') primers. The synthesized PCR product and the vector pETM-20 (N-terminal fusion protein with Trx, TEV-restriction site, his-tag) were digested using NcoI and XhoI restriction enzymes and gel purified. After ligation and transformation the resulting clones were tested for the presence of an insert of the correct size using the restriction enzymes mentioned above. Positive clones were expressed in 3 ml cultures and tested for protein expression using western blots. All clones expressing soluble MKLP-2 were verified by DNA sequencing.

c—Expression and Purification of MKLP-2 Constructs.

For protein expression the MKLP-2 expression plasmid was transformed into competent BL21(DE3) *E. coli* host cells. A colony of transformed bacteria was transferred into 5-20 ml of LB-medium with appropriate antibiotics and pre-cultured overnight at 37° C. The bacterial culture was transferred into 1 l of 2×YT medium (supplemented with appropriate antibiotics) and grown at 37° C. until an $OD_{600}$ 0.6-1.0 was obtained. Cells were induced with 0.5 mM IPTG and grown at 20° C. for 20-24 h. Bacteria were harvested by centrifugation, frozen in liquid nitrogen, and stored at −80° C. All subsequent purification steps were carried out at 4° C. Cells were resuspended in 20 ml resuspension buffer (20 mM PIPES, pH 7.3, 200 mM NaCl, 2 mM $MgCl_2$, 1 mM Na-EGTA, 10 mM imidazole, 0.2 mg/ml DNAse, 0.5 mg/ml lysozyme, and 1 mM PMSF), incubated for 30 minutes, disrupted three-times by sonication for 1 minute, and centrifuged for 60 minutes at 19000 rpm (Beckmann rotor JA-20, at 4° C.). The supernatant was loaded onto a 1 ml Ni-charged His-trap FF column previously equilibrated in buffer A (20 mM PIPES, pH 7.3, 200 mM NaCl, 2 mM $MgCl_2$, 1 mM Na-EGTA, 10 mM imidazole). After washing with buffer A (50 column volumes), the column was extensively washed with buffer B (20 mM PIPES, pH 7.3, 200 mM NaCl, 2 mM $MgCl_2$, 1 mM Na-EGTA, 20 mM imidazole). The protein was eluted with 20 column volumes of buffer C (20 mM PIPES, pH 7.3, 200 mM NaCl, 2 mM $MgCl_2$, 1 mM Na-EGTA, 250 mM imidazole) and collected in fractions of 1 ml. The fractions containing MKLP-2 were concentrated using Amicon Ultra concentrators to about 10 mg/ml and loaded onto a Superose 12 column equilibrated with buffer D (20 mM PIPES, pH 7.3, 200 mM NaCl, 2 mM $MgCl_2$, 1 mM β-mercaptoethanol). Purified protein was collected in fractions of 0.5 ml, analysed by SDS-PAGE, concentrated to 6-10 mg/ml as described above, aliquoted, frozen in liquid nitrogen and stored at −80° C. The purified protein was verified by N-terminal sequencing and mass spectrometry analysis.

Microtubules (MT) Polymerisation and Polymerisation Assays

Tubulin was purified from bovine brain (Asnes et al., *Anal. Biochem.* 98, 64-73 (1979)), aliquoted at 12 mg/ml, frozen in liquid nitrogen, and stored at −80° C.

For the MT-activated ATPase activity of MKLP-2, we used MTs (50 µM) prepared as follows: 50 µl tubulin (12 mg/ml) were mixed with 70 µl PEM (100 mM PIPES, pH 6.9, 1 mM Na-EGTA, and 1 mM $MgCl_2$), warmed to 37° C. and polymerised overnight at 37° C. in the presence of 10 µM taxol and 0.1% $NaN_3$.

Measurement of ATPase Rates

All experiments were performed at room temperature using a 96-well Sunrise photometer (Tecan, Maennedorf, Switzerland) at a final volume of 100 µl per well.

Steady-state ATPase rates were measured using the pyruvate kinase/lactate dehydrogenase-linked assay in buffer A25A (25 mM potassium ACES, pH 6.9, 2 mM $MgAc_2$, 2 mM Na-EGTA, 0.1 mM Na-EDTA, 1 mM β-mercaptoethanol [31]) supplemented with 1 mM MgATP; 2 mM PEP; 0.25 mM NADH; 3-10 µg/ml pyruvate kinase; 3 µg/ml lactate dehydrogenase and 8 µM taxol.

In the presence of taxol-stabilized MTs, 45-80 nM Trx-MKLP-$2_{1-519}$ was used for the assay.

In the absence of MTs, the basal ATPase activity was measured using 3-5 µM Trx-MKLP-$2_{1-519}$ for either the coupled- or the CytoPhos assay (Funk et al., *Anal. Biochem.* 329, 68-76 (2004).

For optimal inhibitor solubility, the assays (as well as control assays in the absence of inhibitor) were carried out in the presence of up to 5% DMSO. The data were analyzed using Kaleidagraph 3.0 (Synergy Software, Reading, Pa.) and Microsoft Excel to obtain the kinetic variables.

Inhibitor Screening

Inhibitor screening of Trx-MKLP-$2_{1-519}$ was performed as previously described for Eg5 (Kozielski et al., *Methods in Molecular Medicine* 137, 189-207 (2007); Debonis, S., et al. *Mol. Cancer Ther.* 3, 1079-1090 (2004)).

In short, to perform the screening buffer A25A was aliquoted into a 96-well µclear plate. The small molecules (3 µl) were added to a final concentration of 0.033 mg/ml. The first (A 1-H1) column of each 96-well plate was used for negative control (the activity of MKLP-2 in the absence of any inhibitor).

The assays were performed in the presence of 2.2% DMSO. After adding 4 µl MKLP-2 (at 3-4 mg/ml) to all 96 wells, the solutions were mixed and the absorbance at 340 nm was measured for 2 to 10 min, taking measurements every 6 sec for each well. Data were imported into Microsoft Excel and treated automatically.

Molecules, for which the measured ATPase activity was reduced by more than three times the SD of the mean of the uninhibited ATPase activity for each plate (eight data points) were considered as potential inhibitors of ATPase activity and aliquoted into two new 96-well plates (174 molecules).

As a secondary screen, we measured the basal ATPase activity of MKLP-2 in the presence of the inhibitors from the primary screen (50 µM) using the CytoPhos assay (Funk et al., *Anal. Biochem.* 329, 68-76 (2004).

Determination of $IC_{50}$ Values $IC_{50}$ values for the inhibition of the basal and MT-stimulated ATPase activity of Trx-MKLP-$2_{1-519}$ were determined by measuring the ATPase activity (without or in the presence of 2 µM MTs) in the presence of increasing inhibitor concentrations between 0 and 200 µM.

When necessary, the inhibitor concentrations were adapted depending on the initial $IC_{50}$ value. Experiments were performed in triplicate and averaged data points are shown with error bars±SD. $IC_{50}$ values were determined by fitting the experimental data to equation:

$$v/v_0 = 100 - (A \times ([I]/[I] + IC_{50}))$$

where v is the reaction velocity at different concentrations of the MKLP-2 inhibitor, $v_0$ represents the control velocity in the absence of inhibitor, A is the amplitude, [I] is the concentration of the inhibitor, and $IC_{50}$ represents the median inhibitory concentration.

Determination of Efficiency of Some Compounds of the Invention Against KB (Human Epidermoid Carcinoma) Cells KB (human epidermoid carcinoma) cells were grown in Dulbecco's Modified Eagle's Medium supplemented with 25 mM glucose, 10% (v/v) fetal calf serum, 100 UI penicillin, 100 µg/mL streptomycin and 1.5 µg/mL fungizone and kept under 5% CO2 at 37° C.

96 well plates were seeded with about 500 KB cells per well in 200 µL medium.

24 hours later, some compounds among those considered in examples, dissolved in DMSO, were added for 72 hours at a final concentration ($10^{-5}$M) in a fixed volume of DMSO (1% final concentration). Controls received an equal volume of DMSO.

40 µL MTS reagent (Promega, Madison, Wis.) per well were added. After 2 hours, the inhibition percentage was calculated by measuring the optical density difference at 490 nm between control and samples.

The results regarding the inhibition efficiency for some compounds considered in examples above-cited against the inhibition of the basal ATPase activity of Trx-MKLP-$2_{1-159}$ are illustrated in Table 2 hereafter.

TABLE 2

| Réf | Molécule | RabK6 basal IC50 X (µM) |
|---|---|---|
| 4 | [structure] | 0 < X < 5 |
| 29 | [structure] | 0 < X < 5 |

TABLE 2-continued
| Réf | Molécule | RabK6 basal IC50 X (μM) |
|---|---|---|
| 30 | 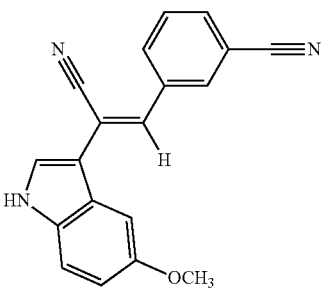 [SMILES: COc1ccc2[nH]cc(/C(C#N)=C/c3cccc(C#N)c3)c2c1] | 0 < X < 5 |
| 25 | 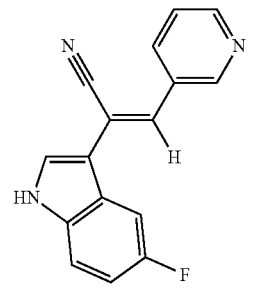 [SMILES: N#C/C(=C\c1cccnc1)c1c[nH]c2ccc(F)cc12] | 0 < X < 5 |
| 23 | 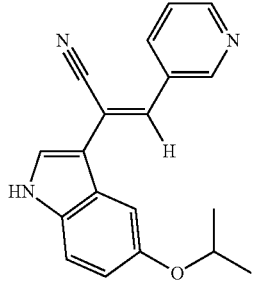 [SMILES: CC(C)Oc1ccc2[nH]cc(/C(C#N)=C/c3cccnc3)c2c1] | 0 < X < 5 |
| 22 | 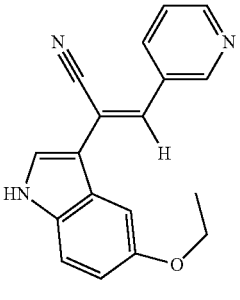 [SMILES: CCOc1ccc2[nH]cc(/C(C#N)=C/c3cccnc3)c2c1] | 0 < X < 5 |
| 28 | 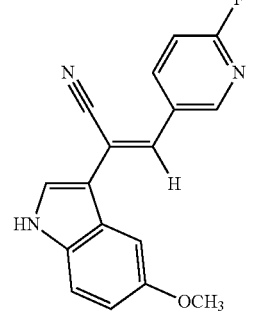 | 0 < X < 5 |
| 31 | 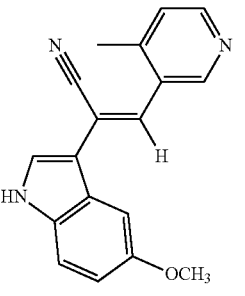 [SMILES: COc1ccc2[nH]cc(/C(C#N)=C/c3cnccc3C)c2c1] | 0 < X < 5 |
| 24 | 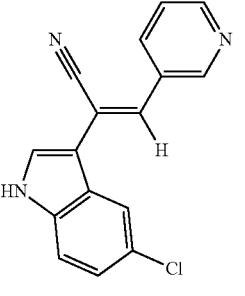 [SMILES: N#C/C(=C\c1cccnc1)c1c[nH]c2ccc(Cl)cc12] | 0 < X < 5 |
| 20 | 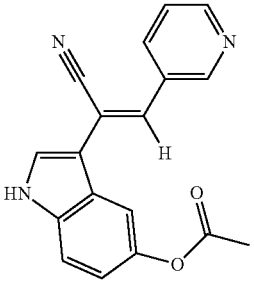 [SMILES: CC(=O)Oc1ccc2[nH]cc(/C(C#N)=C/c3cccnc3)c2c1] | 0 < X < 5 |
| 26 | 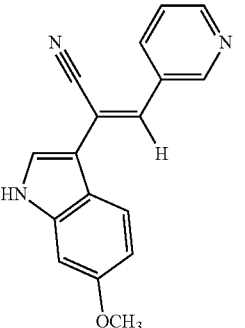 | 5 < X < 10 |
| 16 | 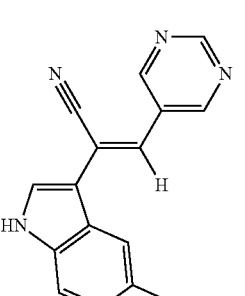 | 5 < X < 10 |

TABLE 2-continued
| Réf | Molécule | RabK6 basal IC50 X (μM) |
|---|---|---|
| 21 | 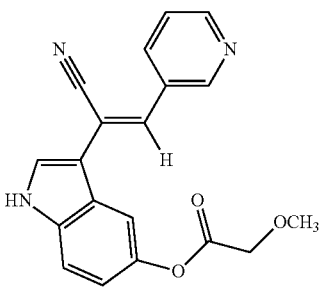 [SMILES: COCC(=O)Oc1ccc2[nH]cc(/C(C#N)=C/c3cccnc3)c2c1] | 5 < X < 10 |
| 1 | 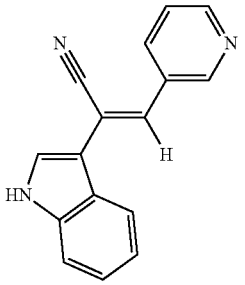 [SMILES: N#C/C(=C\c1cccnc1)c1c[nH]c2ccccc12] | 0 < X < 5 |
| 27 | 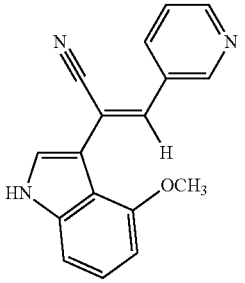 [SMILES: COc1cccc2[nH]cc(/C(C#N)=C/c3cccnc3)c12] | 10 < X < 20 |
| 15 | 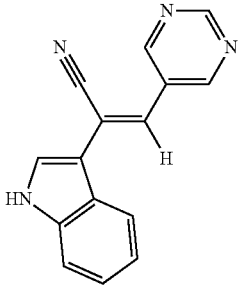 [SMILES: N#C/C(=C\c1cncnc1)c1c[nH]c2ccccc12] | 10 < X < 20 |
| 8 | 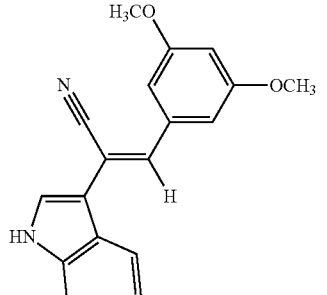 | 0 < X < 5 |
TABLE 2-continued
| Réf | Molécule | RabK6 basal IC50 X (μM) |
|---|---|---|
| 14 | 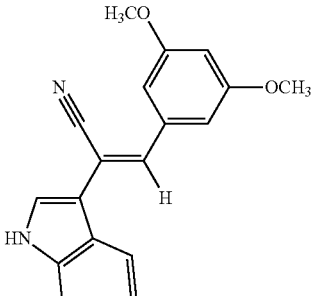 | 5 < X < 10 |
| 32 | 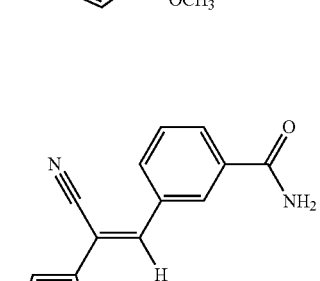 | 10 < X < 20 |
| 5 | 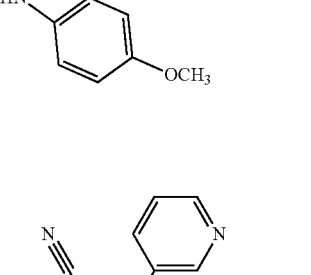 | X > 5 |
| 33 | 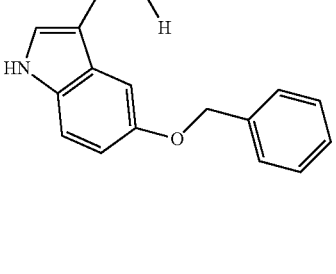 | 10 < X < 20 |

TABLE 2-continued

| Réf | Molécule | RabK6 basal IC50 X (µM) |
|---|---|---|
| 13 | [4-chlorophenyl vinyl nitrile with 1H-indol-3-yl] | 10 < X < 20 |
| 18 | [pyridin-3-yl methyl nitrile with 5-methoxy-1H-indol-3-yl] | 20 < X < 50 |
| 11 | [benzo[1,3]dioxol-5-yl vinyl nitrile with 1H-indol-3-yl] | 10 < X < 20 |
| 19 | [pyridin-3-yl vinyl with 1H-indol-3-yl, nitrile] | 20 < X < 50 |
| 12 | [4-fluorophenyl vinyl nitrile with 1H-indol-3-yl] | 20 < X < 50 |
| 6 | [pyridin-2-yl vinyl nitrile with 5-methoxy-1H-indol-3-yl] | 10 < X < 20 |
| 10 | [3-chlorophenyl vinyl nitrile with 1H-indol-3-yl] | 10 < X < 20 |
| 7 | [3,5-dimethoxy-4-hydroxyphenyl vinyl nitrile with 5-methoxy-1H-indol-3-yl] | 20 < X < 50 |
| 9 | [phenyl vinyl nitrile with 1H-indol-3-yl] | 20 < X < 50 |
| 17 | [pyridin-3-yl methyl nitrile with 1H-indol-3-yl] | X > 50 |

TABLE 2-continued

| Réf | Molécule | RabK6 basal IC50 X (μM) |
|---|---|---|
| 3 | (indole + CN + pyridin-2-yl) | X > 50 |
| 2 | (indole + CN + pyridin-3-yl) | 20 < X < 50 |
| 34 | (pyrrolo-oxazole propyl + CN + pyridin-3-yl) | X > 50 |
| 35 | (2-methyl-5-methoxyindole + CN + pyridin-3-yl) | X > 50 |
| 36 | (7-azaindole + CN + pyridin-3-yl) | 10 < X < 20 |
| 37 | (5-bromoindole + CN + pyridin-3-yl) | 10 < X < 20 |
| 38 | (5-(3,4,5-trimethoxyphenyl)indole + CN + pyridin-3-yl) | 5 < X < 10 |
| 39 | (5-(4-fluorophenyl)indole + CN + pyridin-3-yl) | 10 < X < 20 |
| 40 | (5-aminoindole + CN + pyridin-3-yl) | 0 < X < 5 |

TABLE 2-continued
| Réf | Molécule | RabK6 basal IC50 X (µM) |
|---|---|---|
| 41 | 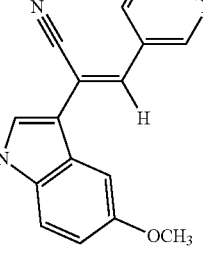 | 0 < X < 5 |
| 42 | | X > 50 |
| 43 | | X > 50 |
| 44 | | X > 50 |
| 45 | | X > 50 |
| 46 | | 10 < X < 20 |
| 47 | | 5 < X < 10 |
| 48 | | 0 < X < 5 |
| 49 | | 5 < X < 10 |
| 50 | | X > 50 |

TABLE 2-continued
| Réf | Molécule | RabK6 basal IC50 X (µM) |
|---|---|---|
| 51 | | X > 50 |
| 52 | | 10 < X < 20 |
| 53 | | 0 < X < 5 |
| 54 | | 5 < X < 10 |
| 55 | | 0 < X < 5 |
| 56 | | X > 50 |
| 57 | | 5 < X < 10 |
| 58 | | 50 X < 10 |
| 59 | | 0 < X < 5 |
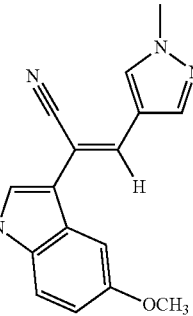
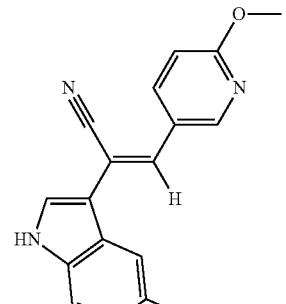
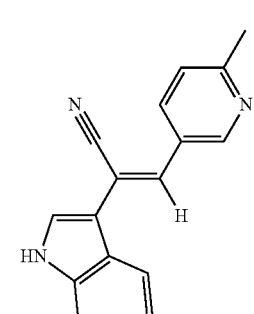
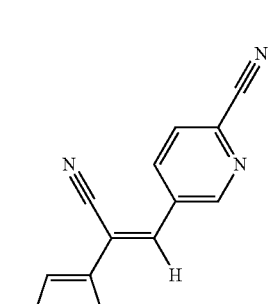

TABLE 2-continued

| Réf | Molécule | RabK6 basal IC50 X (μM) |
|---|---|---|
| 60 | (structure: indole with OCH3, connected to C=C(CN) and CH3, pyridine) | 0 < X < 5 |
| 61 | (structure: indole connected to C=C(CN), pyridine, N) | 0 < X < 5 |

It has also been shown that some of the compounds tested regarding the polymerisation of the microtubules (MTs) do not perturb the MKLP-2-MT interactions.

Accordingly, they may consider as having no significant effect of compounds on the polymerization of microtubules. In addition, Human epidermoid carcinoma cells have been treated with several compounds among those considered in examples above-cited. A particular cytotoxicity effect has been observed.

As discussed above, the present invention provides novel compounds having antitumor and anti-cell proliferative activity, and thus, said compounds are useful for the treatment of cancer.

The present invention is also related to a method for treating, preventing or avoiding cancer or solid tumour in a patient, comprising at least one step consisting in administering to said patient an effective amount of a compound of formula (I), (II), (III), (IV), (V) and/or such as illustrated in examples 1 to 61 according to the present invention.

The present invention is also related to the use of a compound of anyone of formula (I), (II), (III), (IV), (V) and/or such as illustrated in examples 1 to 61 or one of its pharmaceutically acceptable salts according to the present invention for the manufacture of a pharmaceutical composition intended for the treatment of cancer, and in particular of bladder cancer, breast cancer, ovarian cancer, pancreatic cancer, and gastric cancer, cervical cancer, colon cancer, endometrial cancer, head and neck cancer, lung cancer, melanoma, multiple myeloma, leukemia (e.g. myeloid, lymphocytic, myelocytic and lymphoblastic leukemias), non-hodgkin's lymphoma, prostate cancer, rectal cancer, and malignant melanomas.

The present invention is also related to a compound of anyone of formula (I), (II), (III), (IV), (V) and/or such as illustrated in examples 1 to 61 or one of its pharmaceutically acceptable salts according to the present invention for use as a medicament and more particularly for the treatment and/or the prevention of cancer or solid tumors.

The present invention is also directed to pharmaceutical compositions wherein these compositions comprise any one of the compounds as described herein, and optionally comprise a pharmaceutically acceptable carrier.

In certain preferred embodiments, these compositions optionally further comprise one or more additional therapeutic agents. In certain other embodiments, the additional therapeutic agent is an anticancer agent, as discussed in more detail herein. It will also be appreciated that certain of the compounds of present invention can exist in free form for treatment, or where appropriate, as a pharmaceutically acceptable derivative thereof.

According to the present invention, a pharmaceutically acceptable derivative includes, but is not limited to, pharmaceutically acceptable salts, esters, salts of such esters, or any other adduct or derivative which upon administration to a patient in need is capable of providing, directly or indirectly, a compound as otherwise described herein, or a metabolite or residue thereof, e.g., a prodrug.

"Pharmaceutically acceptable carrier", such as above-cited, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Fifteenth Edition, E. W. Martin (Mack Publishing Co., Easton, Pa., 1975) discloses various carriers used in formulating pharmaceutical compositions and known techniques for the preparation thereof. Except insofar as any conventional carrier medium is incompatible with the antiviral compounds of the invention, such as by producing any undesirable biological effect or otherwise interacting in a deleterious manner with any other component(s) of the pharmaceutical composition, its use is contemplated to be within the scope of this invention. Some examples of materials which can serve as pharmaceutically acceptable carriers include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

A compound according to the invention is preferably formulated in dosage unit form for ease of administration and uniformity of dosage. The expression "dosage unit form" as used herein refers to a physically discrete unit of anticancer agent appropriate for the patient to be treated. It will be understood, however, that the total daily usage of the compounds and compositions of the present invention will be decided by the attending physician within the scope of sound medical judgment. The specific therapeutically effective dose level for any particular patient or organism will depend upon a variety of factors including the disorder being treated and the severity of the disorder; the activity of the specific compound employed; the specific composition employed; the age, body weight, general health, sex and diet of the patient;

the time of administration, route of administration, and rate of excretion of the specific compound employed; the duration of the treatment; drugs used in combination or coincidental with the specific compound employed; and like factors well known in the medical arts.

Furthermore, after formulation with an appropriate pharmaceutically acceptable carrier in a desired dosage, the pharmaceutical compositions according to the invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated.

The active compounds can also be in micro-encapsulated form, eventually with one or more excipients as noted above.

It will also be appreciated that the compounds and pharmaceutical compositions of the present invention can be employed in combination therapies, that is, the compounds and pharmaceutical compositions can be administered concurrently with, prior to, or subsequent to, one or more other desired therapeutics or medical procedures.

The invention claimed is:
1. A compound of formula (IV):

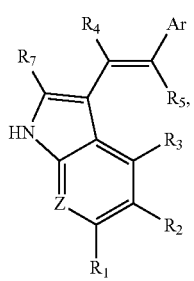

(IV)

wherein:
Z represents a CH unit;
$R_4$ and $R_5$ are different from one another, and
$R_4$ represents a hydrogen atom, a nitrile, an ethyne, a $(C_1-C_5)$alkyl or a carboxamide group, and
$R_5$ represents a hydrogen atom, a $(C_1-C_5)$alkyl, a nitrile or a carboxamide group;
$R_7$ represents a hydrogen atom or a $(C_1-C_5)$alkyl group;
$R_1$, $R_2$ and $R_3$ independently represent a hydrogen atom, a halogen, a hydroxyl, an amine, or a radical $(C_1-C_5)$ alkoxy, phenyl, benzyloxy, acetate, methylcarbamate, $(C_1-C_{10})$alkoxyacetate, said radical optionally substituted by at least one halogen or a $(C_1-C_{10})$alkoxy group;
$R_2$ and $R_3$ optionally form a condensed heterocycle, optionally substituted by a $(C_1-C_5)$alkyl group;
Ar represents an aromatic radical selected from the group consisting of:

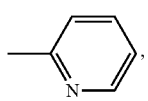

(B")

provided that when Ar is (B") and $R_1$, $R_3$, $R_5$ and $R_7$ represent a hydrogen atom and $R_4$ represents a nitrile group, then $R_2$ is not a hydrogen atom;

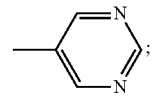

(C")

such that the compound of formula (IV) is not (Z)-2-(1H-indol-3-yl)-3-pyridin-3-yl-acrylonitrile,
and pharmaceutically acceptable salts thereof.
2. A compound selected from the group consisting of:
(Z)-2-(5-methoxy-1H-indol-3-yl)-3-pyridin-3-yl-acrylonitrile;
(Z)-2-(5-ethoxy-1H-indol-3-yl)-3-pyridin-3-yl-acrylonitrile;
(Z)-2-(5-isopropoxy-1H-indol-3-yl)-3-pyridin-3-yl-acrylonitrile;
(Z)-2-(5-chloro-1H-indol-3-yl)-3-pyridin-3-yl-acrylonitrile;
(Z)-2-(5-fluoro-1H-indol-3-yl)-3-pyridin-3-yl-acrylonitrile;
(Z)-2-(4-methoxy-1H-indol-3-yl)-3-pyridin-3-yl-acrylonitrile;
(Z)-3-(6-fluoropyridin-3-yl)-2-(5-methoxy-1H-indol-3-yl)-acrylonitrile;
(Z)-2-(6-methoxy-1H-indol-3-yl)-3-pyridin-3-yl-acrylonitrile;
(Z)-2-(1H-indol-3-yl)-3-pyrimidin-5-yl-acrylonitrile;
(Z)-2-(5-methoxy-1H-indol-3-yl)-3-pyrimidin-5-yl-acrylonitrile;
(Z)-3-(1-cyano-2-(pyridin-3-yl)vinyl)-1H-indol-5-yl-acetate;
(Z)-3-(1-cyano-2-(pyridin-3-yl)vinyl)-1H-indol-5-yl 2-methoxyacetate;
(Z)-2-(5-benzyloxy-1H-indol-3-yl)-3-pyridin-3-yl-acrylonitrile;
(Z)-3-(3,5-dimethoxy-phenyl)-2-(5-methoxy-1H-indol-3-yl)-acrylonitrile;
(Z)-3-(3,5-dimethoxy-phenyl)-2-(1H-indol-3-yl)-acrylonitrile;
(Z)-3-(4-chloro-phenyl)-2-(1H-indol-3-yl)-acrylonitrile;
(Z)-2-(5-methoxy-1H-indol-3-yl)-3-pyridin-3-yl-propionitrile;
(Z)-3-(1H-indol-3-yl)-2-pyridin-3-yl-acrylonitrile;
(Z)-2-(5-methoxy-1H-indol-3-yl)-3-pyridin-2-yl-acrylonitrile;
(Z)-3-(3-chloro-phenyl)-2-(1H-indol-3-yl)-acrylonitrile;
(Z)-3-(4-hydroxy-3,5-dimethoxy-phenyl)-2-(5-methoxy-1H-indol-3-yl)-acrylonitrile;
(Z)-2-(5-hydroxy-1H-indol-3-yl)-3-pyridin-3-yl-acrylonitrile;
(Z)-3-[2-cyano-2-(5-methoxy-1H-indol-3-yl)-vinyl]-benzonitrile;
(Z)-2-(5-methoxy-1H-indol-3-yl)-3-(4-methyl-pyridin-3-yl)-acrylonitrile;
(Z)-3-[2-cyano-2-(5-methoxy-1H-indol-3-yl)-vinyl]-benzamide;
(Z)-3-[2-cyano-2-(5-methoxy-1H-indol-3-yl)-vinyl]-1-methylpyridinium iodide;
(Z)-2-(2-propyl-6H-oxazolo[4,5-e]indol-8-yl)-3-(pyridin-3-yl)acrylonitrile;
(Z)-2-(5-methoxy-2-methyl-1H-indol-3-yl)-3-pyridin-3-yl-acrylonitrile;
(Z)-3-(pyridin-3-yl)-2-(1H-pyrrolo[2,3-b]pyridin-3-yl)-acrylonitrile;
(Z)-2-(5-bromo-1H-indol-3-yl)-3-pyridin-3-yl-acrylonitrile;

(Z)-3-(pyridin-3-yl)-2-(5-(3,4,5-trimethoxyphenyl)-1H-indol-3-yl)-acrylonitrile;
(Z)-2-(5-(4-fluorophenyl)-1H-indol-3-yl)-3-(pyridin-3-yl)-acrylonitrile;
(Z)-2-(5-amino-1H-indol-3-yl)-3-pyridin-3-yl-acrylonitrile;
(Z)-methyl 3-(1-cyano-2-(pyridin-3-yl)vinyl)-1H-indol-5-ylcarbamate;
(Z)-2-(1H-indol-3-yl)-3-(3-nitro-phenyl)-acrylonitrile;
(Z)-2-(5-methoxy-1H-indol-3-yl)-3-(3-nitro-phenyl)-acrylonitrile;
(Z)-3-(3-amino-phenyl)-2-(1H-indol-3-yl)-acrylonitrile;
(Z)-3-(3-amino-phenyl)-2-(5-methoxy-1H-indol-3-yl)-acrylonitrile;
(Z)-2-(5-methoxy-1H-indol-3-yl)-3-(5-methoxy-pyridin-3-yl)-acrylonitrile;
(Z)-3-(4-chloro-pyridin-3-yl)-2-(5-methoxy-1H-indol-3-yl)-acrylonitrile;
(Z)-3-(2-fluoropyridin-3-yl)-2-(5-methoxy-1H-indol-3-yl)-acrylonitrile;
(Z)-3-(6-chloropyridin-3-yl)-2-(5-methoxy-1H-indol-3-yl)-acrylonitrile;
(Z)-2-(5-methoxy-1H-indol-3-yl)-3-thiophen-3-yl-acrylonitrile;
(Z)-2-(5-methoxy-1H-indol-3-yl)-3-(1-methyl-1H-pyrazol-3-yl)-acrylonitrile;
(Z)-3-(6-methoxy-pyridin-3-yl)-2-(5-methoxy-1H-indol-3-yl)-acrylonitrile;
(Z)-2-(5-methoxy-1H-indol-3-yl)-3-(6-methylpyridin-3-yl)-acrylonitrile;
(Z)-5-[2-cyano-2-(5-methoxy-1H-indol-3-yl)-vinyl]-picolinonitrile;
(Z)-3-[2-cyano-2-(5-hydroxy-1H-indol-3-yl)-vinyl]-benzonitrile;
(Z)-2-(1H-indol-3-yl)-3-pyridin-3-yl-acrylamide;
(E)-5-methoxy-3-(1-(pyridin-3-yl)but-1-en-3-yn-2-yl)-1H-indole;
5-methoxy-3-(1-(pyridin-3-yl)prop-1-en-2-yl)-1H-indole;
(Z)-2-(5-methoxy-1H-indol-3-yl)-3-(pyridin-3-yl)-but-2-enenitrile; and
(Z)-(1H-indol-3-yl)-(pyridin-3-ylimino)-acetonitrile,
and pharmaceutically acceptable salts thereof.

3. The compound according to claim 2 selected from the group consisting of:
(Z)-2-(5-methoxy-1H-indol-3-yl)-3-pyridin-3-yl-acrylonitrile;
(Z)-2-(5-ethoxy-1H-indol-3-yl)-3-pyridin-3-yl-acrylonitrile;
(Z)-2-(5-isopropoxy-1H-indol-3-yl)-3-pyridin-3-yl-acrylonitrile;
(Z)-2-(5-chloro-1H-indol-3-yl)-3-pyridin-3-yl-acrylonitrile;
(Z)-2-(5-fluoro-1H-indol-3-yl)-3-pyridin-3-yl-acrylonitrile;
(Z)-2-(4-methoxy-1H-indol-3-yl)-3-pyridin-3-yl-acrylonitrile;
(Z)-3-(6-fluoropyridin-3-yl)-2-(5-methoxy-1H-indol-3-yl)-acrylonitrile;
(Z)-2-(6-methoxy-1H-indol-3-yl)-3-pyridin-3-yl-acrylonitrile;
(Z)-2-(1H-indol-3-yl)-3-pyrimidin-5-yl-acrylonitrile;
(Z)-2-(5-methoxy-1H-indol-3-yl)-3-pyrimidin-5-yl-acrylonitrile;
(Z)-3-(1-cyano-2-(pyridin-3-yl)vinyl)-1H-indol-5-yl-acetate;
(Z)-3-(1-cyano-2-(pyridin-3-yl)vinyl)-1H-indol-5-yl 2-methoxyacetate;
(Z)-2-(5-hydroxy-1H-indol-3-yl)-3-pyridin-3-yl-acrylonitrile;
(Z)-3-[2-cyano-2-(5-methoxy-1H-indol-3-yl)-vinyl]-benzonitrile;
(Z)-2-(5-methoxy-1H-indol-3-yl)-3-(4-methyl-pyridin-3-yl)-acrylonitrile;
(Z)-3-(pyridin-3-yl)-2-(5-(3,4,5-trimethoxyphenyl)-1H-indol-3-yl)-acrylonitrile
(Z)-methyl 3-(1-cyano-2-(pyridin-3-yl)vinyl)-1H-indol-5-ylcarbamate;
(Z)-3-(4-chloro-pyridin-3-yl)-2-(5-methoxy-1H-indol-3-yl)-acrylonitrile;
(Z)-2-(5-methoxy-1H-indol-3-yl)-3-(6-methylpyridin-3-yl)-acrylonitrile;
(Z)-3-[2-cyano-2-(5-hydroxy-1H-indol-3-yl)-vinyl]-benzonitrile;
5-methoxy-3-(1-(pyridin-3-yl)prop-1-en-2-yl)-1H-indole; and
(Z)-(1H-indol-3-yl)-(pyridin-3-ylimino)-acetonitrile,
and pharmaceutically acceptable salts thereof.

4. The compound according to any one of claims 1 to 3, which is suitable for use as a medicament.

5. A pharmaceutical composition, comprising as an active ingredient a compound according to anyone of claims 1 to 3.

6. The compound of claim 1, wherein $R_2$ and $R_3$ form a benzoxazole optionally substituted by a $(C_1-C_5)$alkyl group.

* * * * *